United States Patent
Hong et al.

(10) Patent No.: US 10,196,365 B2
(45) Date of Patent: Feb. 5, 2019

(54) QUINAZOLINE DERIVATIVE, PREPARATION METHOD THEREFOR, AND PHARMACEUTICAL COMPOSITION AND APPLICATION THEREOF

(71) Applicant: ARROMAX PHARMATECH CO., LTD., Suzhou, Jiangsu (CN)

(72) Inventors: Jian Hong, Suzhou (CN); Xin Xu, Suzhou (CN); Xiaoyong Le, Suzhou (CN); Zonghua Zhang, Suzhou (CN)

(73) Assignee: ARROMAX PHARMATECH CO., LTD., Suzhou, Jiangsu (CN)

( * ) Notice: Subject to any disclaimer, the term of this patent is extended or adjusted under 35 U.S.C. 154(b) by 0 days.

(21) Appl. No.: 15/504,187

(22) PCT Filed: Aug. 15, 2014

(86) PCT No.: PCT/CN2014/084472
§ 371 (c)(1),
(2) Date: Apr. 24, 2017

(87) PCT Pub. No.: WO2016/023217
PCT Pub. Date: Feb. 18, 2016

(65) Prior Publication Data
US 2017/0247339 A1  Aug. 31, 2017

(51) Int. Cl.
*C07D 239/94* (2006.01)
*A61K 31/517* (2006.01)
*C07D 401/12* (2006.01)

(52) U.S. Cl.
CPC .......... *C07D 239/94* (2013.01); *A61K 31/517* (2013.01); *C07D 401/12* (2013.01)

(58) Field of Classification Search
CPC .................................................. C07D 239/94
See application file for complete search history.

(56) References Cited

U.S. PATENT DOCUMENTS

| 5,760,041 A | 6/1998 | Wissner et al. |
| 2014/0206687 A1 | 7/2014 | Xia et al. |

FOREIGN PATENT DOCUMENTS

| CN | 1161330 A | 10/1997 |
| WO | WO-97-38983 A1 | 10/1997 |
| WO | 2007055514 A1 | 5/2007 |
| WO | 2010151710 A2 | 12/2010 |
| WO | WO-2012136099 A1 | 10/2012 |
| WO | 2013053206 A1 | 4/2013 |
| WO | 2014177038 A1 | 11/2014 |

OTHER PUBLICATIONS

Pinedo et al. (2000).*
McMahon et al (2000).*
Jan. 6, 2017, International Preliminary Report on Patentability Chapter II issued in International Patent Application No. PCT/CN2014/084472 (in English).
Mar. 20, 2017, First Chinese Office Action issued in Chinese Patent Application No. 201480003627.0.
Jun. 7, 2017, ESR issued in European Patent Application No. 14899810.7.
Anja Michalczyk, et al, "Structural insights into how irreversible inhibitors can overcome drug resistance in EGFR", Bioorganic & Medicinal Chemistry, 2008, 16, pp. 3482-3488.
Yongjun Mao, et al, "Design, synthesis and biological evaluation of novel pyrimidine, 3-cyanopyridine and m-amino-N-phenylbenzamide based monocyclic EGFR tyrosine kinase inhibitors" Bioorganic & Medicinal Chemistry, 2013, 21, pp. 3090-3104.
Hai Feng Chen, "Computational Study of the Binding Mode of Epidermal Growth Factor Receptor Kinase Inhibitors"—Chemical Biology& Drug Design, Blackwell Publishing TD., Oxford, GB, vol. 71, No. 5, May 1, 2008, pp. 434-446.

* cited by examiner

*Primary Examiner* — Paul V Ward
(74) *Attorney, Agent, or Firm* — Harness, Dickey & Pierce, P.L.C.

(57) ABSTRACT

Disclosed are a quinazoline derivative, a preparation method therefor, and a pharmaceutical composition and an application thereof. The present invention provides a compound represented by general formula I, a stereoisomer thereof and a pharmaceutical acceptable salt or a solvate thereof. The quinazoline derivative of the present invention has a unique chemical structure, is characterized by irreversibly inhibiting EGFR tyrosine kinase, has high biological activity, apparently improves the inhibiting effect on the EGFR tyrosine kinase, has quite strong tumor inhibiting effect on tumor cells and a transplantation tumor pathological model of animal tumors, and has good market developing prospects.

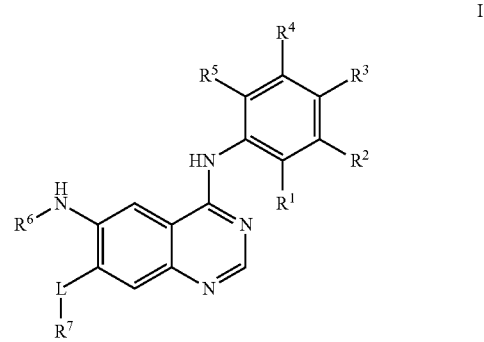

13 Claims, No Drawings

QUINAZOLINE DERIVATIVE, PREPARATION METHOD THEREFOR, AND PHARMACEUTICAL COMPOSITION AND APPLICATION THEREOF

CROSS-REFERENCE TO RELATED APPLICATIONS

This application is a National Stage of International Application No. PCT/CN2014/084472, filed Aug. 15, 2014 and published in Chinese as WO 2016/023217 A1 on Feb. 18, 2016. The entire disclosures of the above application are incorporate by reference herein.

FIELD OF INVENTION

The present invention relates to a quinazoline derivative, a preparation method therefor, and a pharmaceutical composition and an application thereof.

PRIOR ARTS

As the first major lethal disease in the world, tumor is a serious threat to human life and health. According to the World Health Organization (WHO) statistics, nearly 7 million patients die of tumors each year worldwide, of which lung cancer is a disease with highest morbidity and mortality in tumors for men, while breast cancer and lung cancer for women. The morbidity and mortality of tumors are directly related to the changes of living environments and living habits, effects of adverse environments and some unfavorable factors. Throughout the world, the rising trend of the morbidity and mortality for various tumors are obvious in recent years, these tumors include lung cancer, liver cancer, colorectal cancer, breast cancer and the like, of which the largest increase is in lung cancer and breast cancer. Based on the above reasons, there is an urgent need for effective antitumor drugs in clinical practice, therefore the antitumor drugs market has broad prospects for development.

Chemotherapy, surgery and radiotherapy are three main treatment methods for tumors in the past. Traditional chemotherapy mainly employs cytotoxic drugs, and it inhibits the tumor growth through non-selectively killing tumor cells and normal cells, thus it will inevitably damage human normal cells while killing tumor cells, so as to induce adverse drug reactions. Nowadays with the deepening of the research on cells signal transduction pathway, it has become the key field of the innovative drug R&D to search for a new generation of antitumor drugs for tumor specific molecular targets, global scientists are aggressively using this approach to develop new targeted antitumor drugs. Compared with the cytotoxic antitumor drug treatment, cell signal transduction inhibitors can selectively alter the specific pathway and signaling of tumor survival and proliferation, thereby promoting apoptosis, rather than killing cancer cells through non-selective cytotoxic effects, so the cell signal transduction inhibitors have the characteristics of higher selectivity and lower toxicity, and are known as the "Cancer treatment missile". To date there have been many kinds of targeted signal transduction inhibitors applied in clinical tumors treatment, most of which are mainly tyrosine kinase inhibitors as antitumor drugs.

Epidermal growth factor receptor (EGFR) is a multifunctional glycoprotein widely distributed in cytomembranes of human tissue, and an oncogene homolog of the avian erythroblastic leukemia viral (v-erb-B), which belongs to protein tyrosine kinase. The family members of EGFR include EGFR, HER-2, HER-3, HER-4; among them the EGFR subfamily (ErbB and HER) plays a very important role in many processes of regulating cell proliferation and survival. After binding to ligands, EGFR activates the tyrosine kinase activity itself by forming a dimer with the homotypic or heterotypic (HER family subtype) followed by combing with ATP, the dimerization leads to tyrosine residues phosphorylation in the catalytic domain of the receptor, and as the binding site for subsequent signal molecule, affects the key signal transmission on the signal pathways, thus regulates the cell cycle and apoptosis. The clinical studies showed that EGFR and so on in epithelial derived tumors, such as non-small cell lung cancer, breast cancer, colorectal cancer, ovarian cancer, prostate cancer, esophageal cancer, pancreatic cancer and other various tumors, have situations of mutations abnormal activation and overexpression.

Currently marketed drugs include the first generation selective EGFR tyrosine kinase inhibitor gefitinib (Iressa, ZD1839), erlotinib (Tarceva, OSI-774), and the second generation EGFR/HER2 dual inhibitor lapatinib (Tykerb, GW572016). All the above three drugs are reversible EGFR tyrosine kinase inhibitors. A study found that related tumors initially produce a good therapeutic response to these drugs, but after a few months of the treatment the disease progression would appear, resulting in drug resistance, and affecting treatment effects. Drug resistance of marketed drugs such as gefitinib and erlotinib in the clinical treatment of advanced non-small cell lung cancer was reported in the literature (Bioorganic & Medicinal 2008 Chemistry, 163482-3488).

The focus of R&D begins to transfer to the third generation irreversible inhibitors for EGFR targets, in order to solve the problem of drug resistance caused by the kinases mutation. Unlike the first two generations EGFR reversible inhibitors, the EGFR irreversible inhibitors bind to the ATP binding sites with chemical bonds, which are more tightly and closely, and can reduce drug resistance. Afatinib (Gilotrif, BIBW-2992) approved by FDA in 2013, neratinib (HKI-272) and dacomitinib (PF-00299804) in clinical phase III are belong to the third generation irreversible inhibitors.

The literature WO97/38983 disclosed a class of irreversible EGFR tyrosine kinase inhibitors, which introduce a Michael addition reaction receptor at 6-position of quinazoline to give a Michael addition with —SH of cysteine (Cys773) on the active center pocket wall of the EGFR tyrosine kinase. But the compounds disclosed in WO97/3898 have certain inhibitory activity to EGFR tyrosine kinase, and have disadvantages of lower activity of the animal in vivo pathological model, larger amount of dosage, longer administration period, and obvious side effects. Although small molecule kinase inhibitors have opened up a new field of tumor therapy with their targeting advantage, the problem of drug resistance and safety are still challenges for the future research and development of anti-cancer drugs. Therefore, it's of profound significance to develop more efficient and safer kinase inhibitors, in-depth understand the mechanism of drug action and play its anti-tumor effect, for the ultimate victory over the human cancer.

CONTENT OF THE PRESENT INVENTION

The technical problem to be solved in the present invention is for overcoming the defects of lower activity, longer administration time of the EGFR tyrosine kinase inhibitors available, and to which the tyrosine kinase has certain resistance, so as to provide a quinazoline derivative, a preparation method therefor, a pharmaceutical composition and an application thereof, the quinazoline derivative in the present invention has high activity, and has good market developing prospects.

The present invention provides a compound represented by general formula I, a stereoisomer thereof and a pharmaceutical acceptable salt or a solvate thereof,

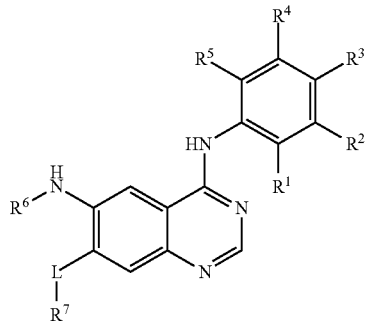

I wherein, each of $R^1$, $R^2$, $R^3$, $R^4$ and $R^5$ independently represents a hydrogen, a halogen (e.g., a fluorine, a chlorine, a bromine or an iodine, preferably a fluorine or a chlorine), a substituted or unsubstituted $C_1$-$C_6$ alkoxy (the "substituted or unsubstituted $C_1$-$C_6$ alkoxy" may be a "substituted or unsubstituted methoxy", a "substituted or unsubstituted ethoxy", a "substituted or unsubstituted propoxy", a "substituted or unsubstituted iso-propoxy", a "substituted or unsubstituted butoxy", a "substituted or unsubstituted iso-butoxy", a "substituted or unsubstituted tert-butoxy"; the "substituted methoxy" is preferably

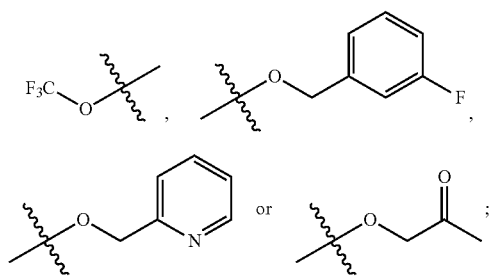

the "substituted ethoxy" is preferably

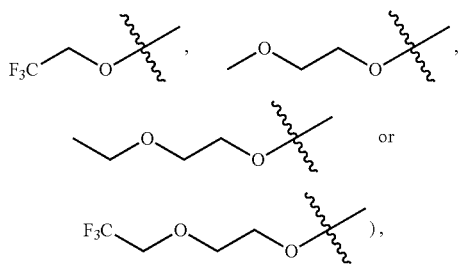

a $C_2$-$C_6$ alkynyl (e.g,

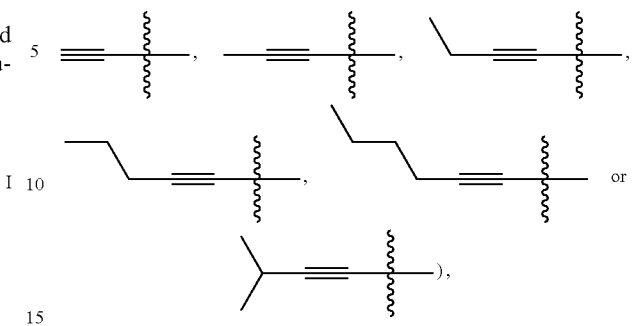

a "substituted or unsubstituted $C_1$-$C_6$ alkylamino" (the "substituted or unsubstituted $C_1$-$C_6$ alkylamino" e.g., a "substituted or unsubstituted methylamino", a "substituted or unsubstituted ethylamino", a "substituted or unsubstituted propylamino", a "substituted or unsubstituted iso-propylamino", a "substituted or unsubstituted butylamino", a "substituted or unsubstituted iso-butylamino", a "substituted or unsubstituted tert-butylamino"; the "substituted ethylamino" is preferably

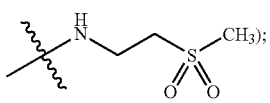

the "substituted" in the "substituted or unsubstituted $C_1$-$C_6$ alkoxy" and the "substituted or unsubstituted $C_1$-$C_6$ alkylamino" is being substituted by one or more substituents which may be the same or different, each substituent being independently selected from the group consisting of a halogen (e.g., a fluorine, a chlorine, a bromine or an iodine, preferably a fluorine or a chlorine), a substituted or unsubstituted $C_5$-$C_{10}$ aryl (e.g., a "substituted or unsubstituted phenyl", the "substituted phenyl" is preferably 2-fluorophenyl), a "$C_2$-$C_{10}$ heteroaryl containing 1 to 3 of heteroatoms, and in which the heteroatom is an oxygen, a sulfur or a nitrogen" (preferably a "$C_4$-$C_6$ heteroaryl containing 1 to 2 of heteroatoms, and in which the heteroatom is a nitrogen", the "$C_4$-$C_6$ heteroaryl containing 1 to 2 of heteroatoms, and in which the heteroatom is a nitrogen" e.g., pyridyl), a $C_1$-$C_6$ alkyloxy (e.g., a methoxy, an ethoxy, a propoxy, an iso-propoxy, or a tert-butoxy),

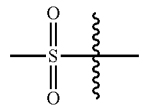 [SMILES: *S(C)(=O)=O]

and a $C_1$-$C_6$ carbonyl (e.g.,

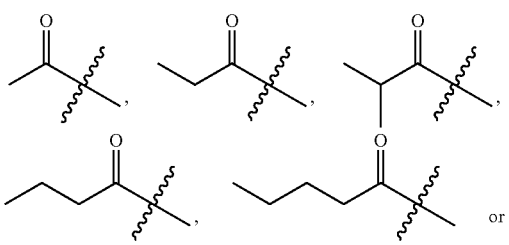

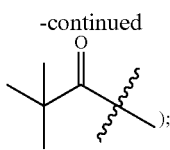

the "substituted" in the "substituted or unsubstituted C₅-C₁₀ aryl" is being substituted by one or more substituents which may be the same or different, each substituent being independently selected from the group consisting of a fluorine, a chlorine, and a bromine;

R⁶ represents

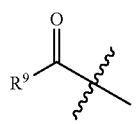

(preferably

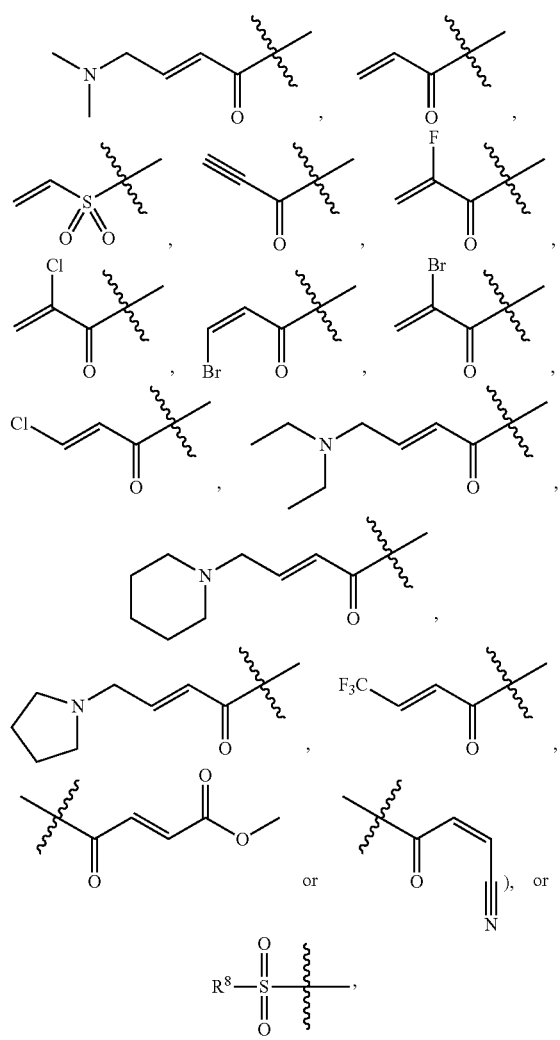

), or

R⁸—S(=O)₂— each of R⁸ and R⁹ independently represents a "substituted or unsubstituted C₂-C₆ alkenyl" or a "substituted or unsubstituted C₂-C₆ alkynyl", the "substituted" in the "substituted or unsubstituted C₂-C₆ alkenyl" and the "substituted or unsubstituted C₂-C₆ alkynyl" is being substituted by one or more substituents which may be the same or different, each substituent being independently selected from the group consisting of a halogen (e.g., a fluorine, a chlorine, a bromine or an iodine, preferably a fluorine or a chlorine), a cyano, a substituted or unsubstituted C₁-C₆ alkyl (the "substituted or unsubstituted C₁-C₆ alkyl" is preferably a trifluoromethyl or an aminomethyl) and a ester group; the "substituted" in the "substituted or unsubstituted C₁-C₆ alkyl" is being substituted by one or more substituents which may be the same or different, each substituent being independently selected from the group consisting of an amino, a halogen (a fluorine, a chlorine, a bromine or an iodine), a C₁-C₆ alkylamino and a C₂-C₆ cycloalkylamino;

L represent a covalent bond, O, S or

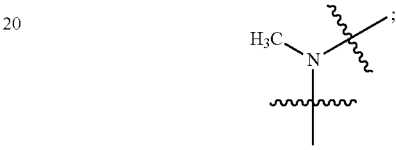

R⁷ represents a substituted or unsubstituted C₁-C₆ alkyl (the "substituted or unsubstituted C₁-C₆ alkyl" is preferably a "substituted or unsubstituted ethyl", a "substituted or unsubstituted propyl", a "substituted or unsubstituted iso-propyl", a "substituted or unsubstituted butyl", a "substituted or unsubstituted iso-butyl", a "substituted or unsubstituted tert-butyl"; the "substituted ethyl" is preferably

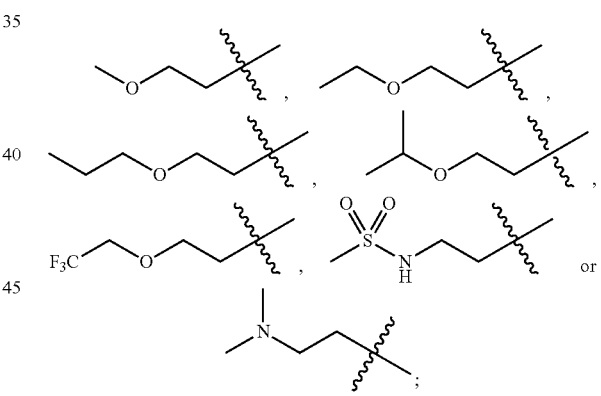

the "substituted propyl" is preferably

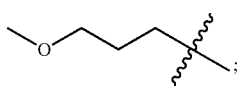 [SMILES: *CCCOC]

the "substituted iso-propyl" is preferably

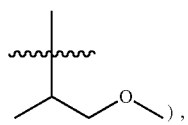

), the "substituted" in the "substituted or unsubstituted $C_1$-$C_6$ alkyl" is being substituted by one or more substituents which may be the same or different, each substituent being independently selected from the group consisting of a $C_1$-$C_6$ alkyoxy (a methoxy, an ethoxy, a propoxy, an iso-propoxy, a butoxy, an iso-butoxy or a tert-butoxy), a "halogen substituted $C_1$-$C_6$ alkyoxy" (the "halogen" in the "halogen substituted $C_1$-$C_6$ alkyoxy" may be a fluorine, a chlorine, or a bromine, the "$C_1$-$C_6$ alkyoxy" in the "halogen substituted $C_1$-$C_6$ alkyoxy" may be a methoxy, an ethoxy, a propoxy, an iso-propoxy, a butoxy, an iso-butoxy or a tert-butoxy; a fluorinated ethoxy is preferably a trifluoroethoxy),

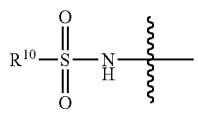

(preferably

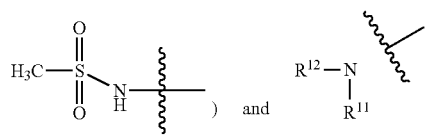

(preferably

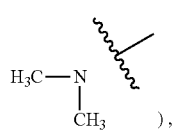

each of $R^{10}$, $R^{11}$ and $R^{12}$ independently represents a $C_1$-$C_6$ alkyl (e.g., a methyl, an ethyl, a propyl, an iso-propyl, a butyl, an iso-butyl or a tert-butyl).

In the present invention, in the compound represented by general formula I, more preferably $R^1$ represents a hydrogen; more preferably $R^2$ represents a hydrogen, a fluorine, a chlorine or a $C_2$-$C_6$ alkynyl (e.g.,

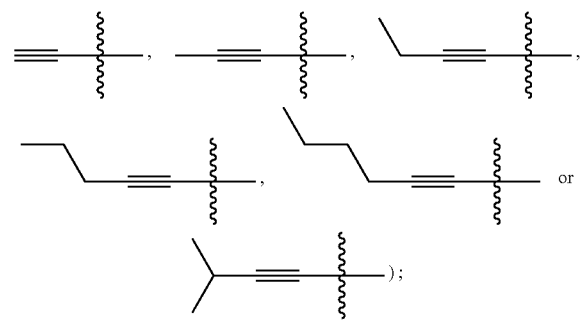

more preferably $R^3$ represents a hydrogen, a fluorine, a chlorine,

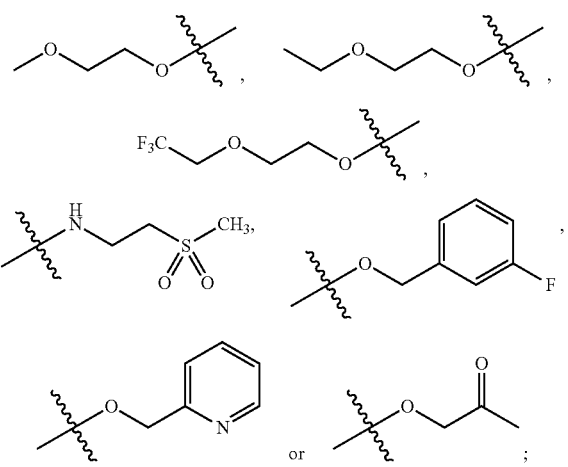

more preferably $R^4$ represents a hydrogen, a fluorine or a chlorine;

more preferably $R^5$ represents a hydrogen;

more preferably $R^6$ represents

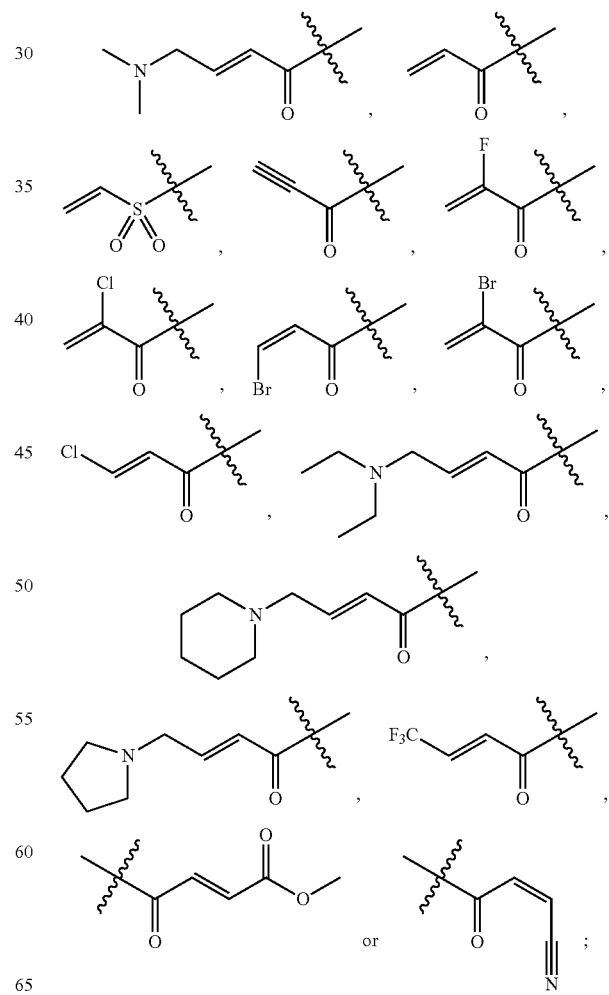

more preferably R⁷ represents
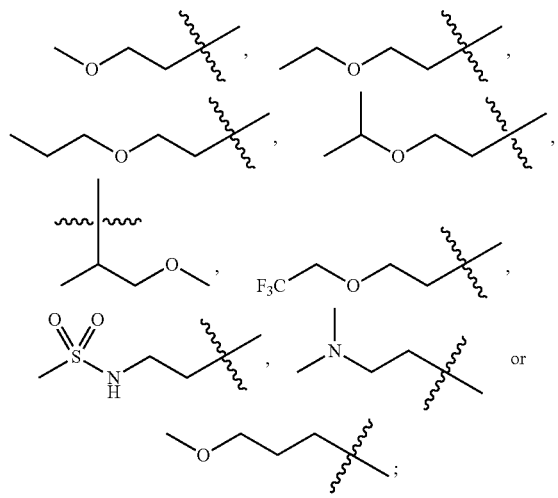
more preferably L represents O, S or
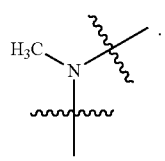
In the present invention, more preferably the compound represented by general formula I is selected from the group consisting of
I-1
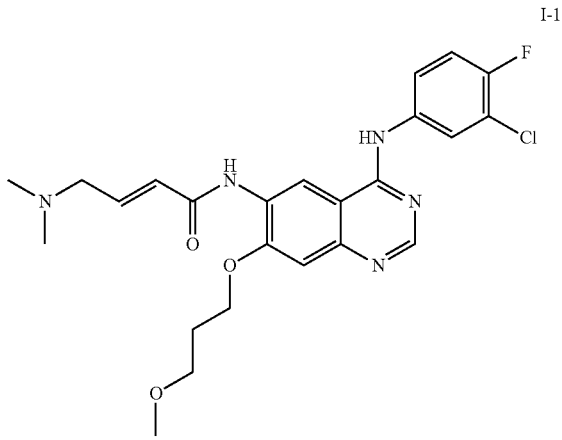
I-2
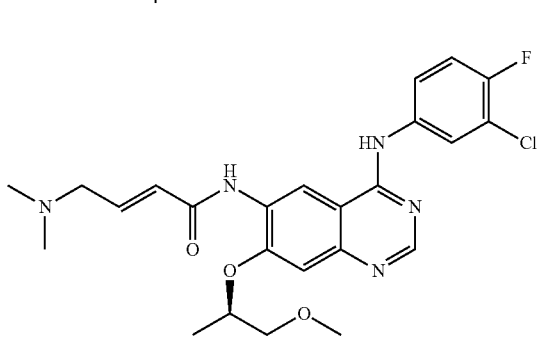
I-3
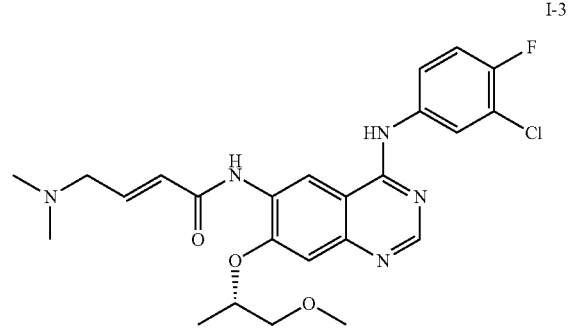
I-4
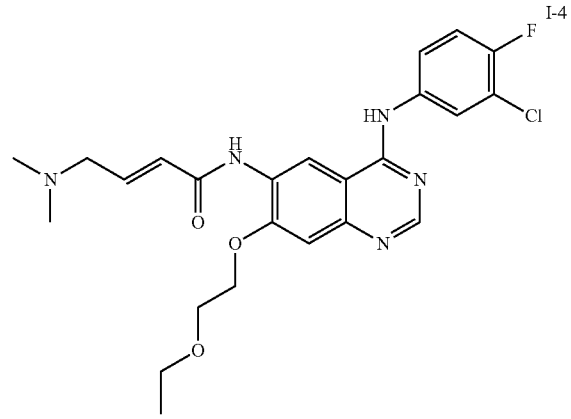
I-5
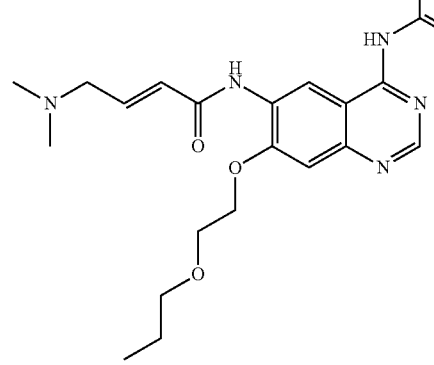
I-6
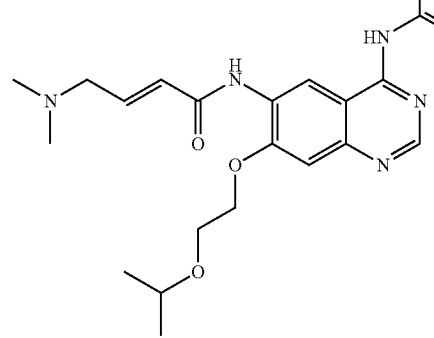

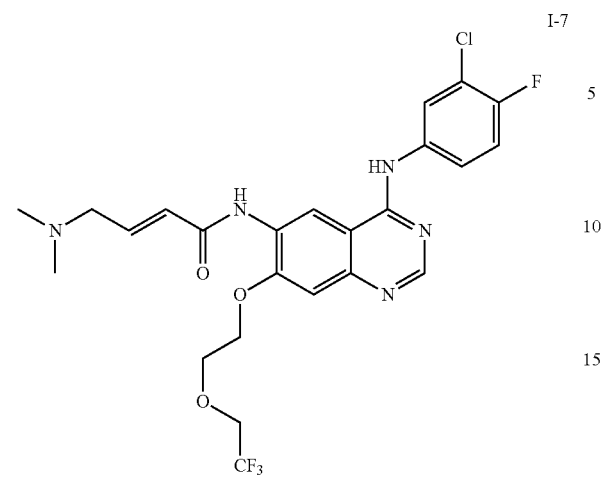
I-7
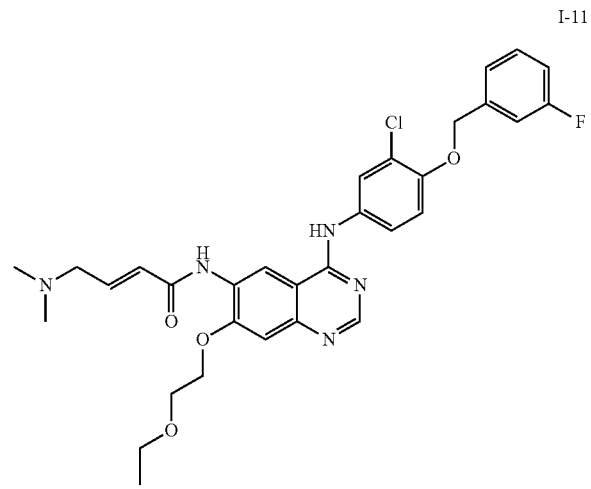
I-11
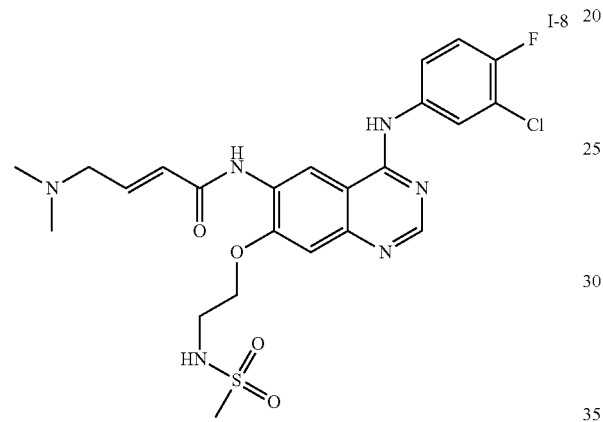
I-8
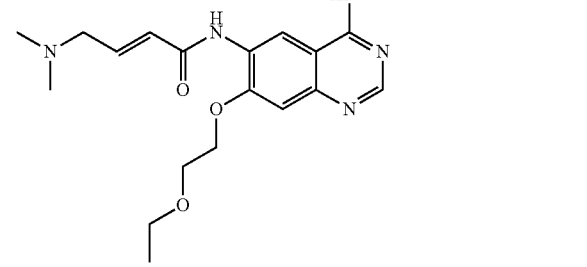
I-12
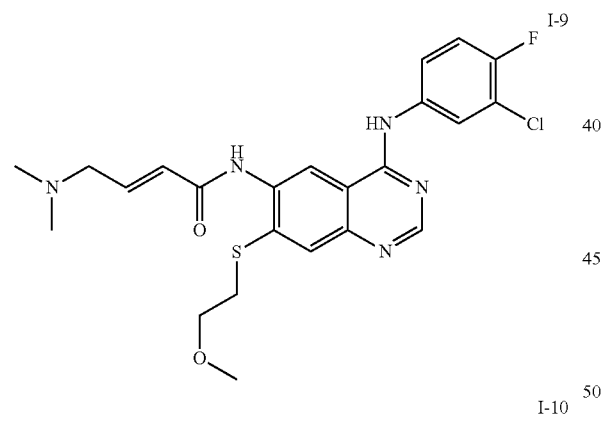
I-9
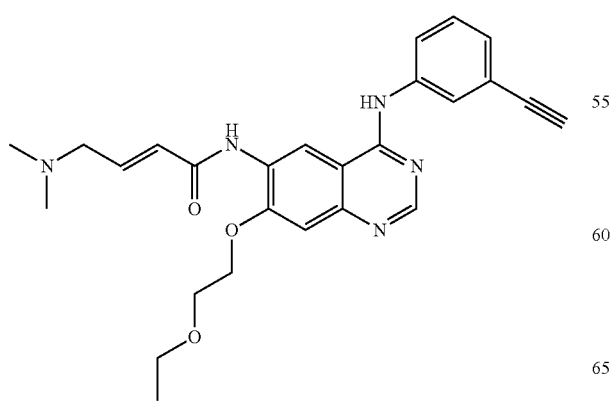
I-10
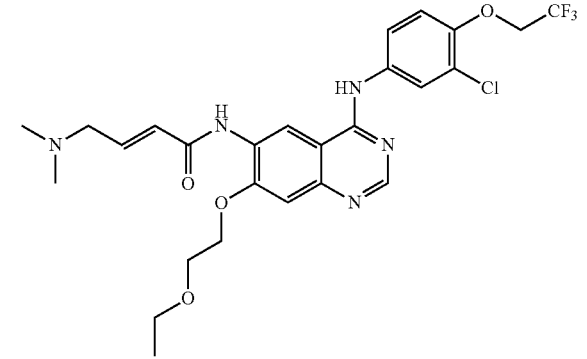
I-13

-continued
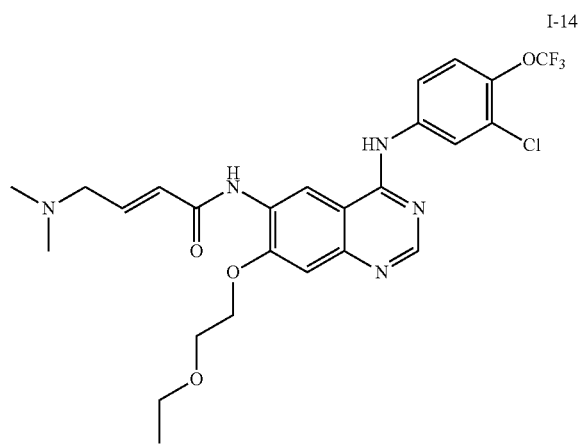
I-14
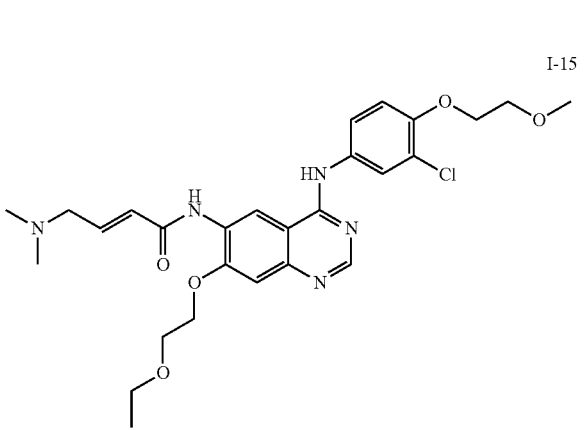
I-15
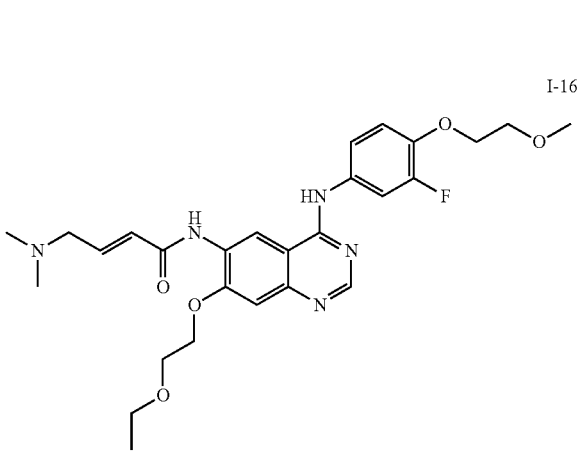
I-16
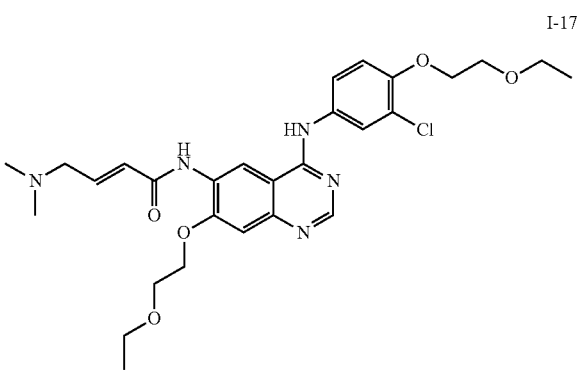
I-17
-continued
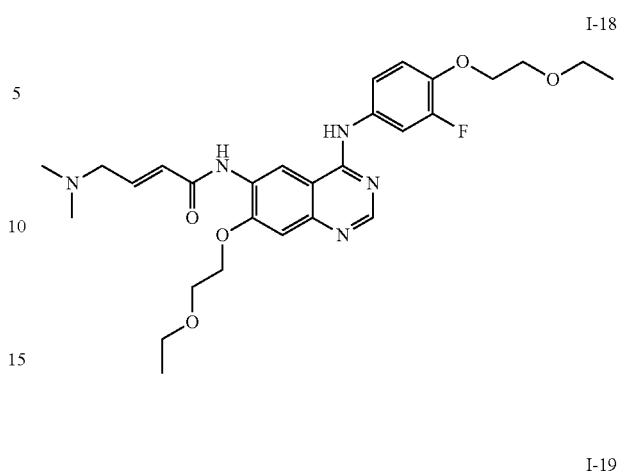
I-18
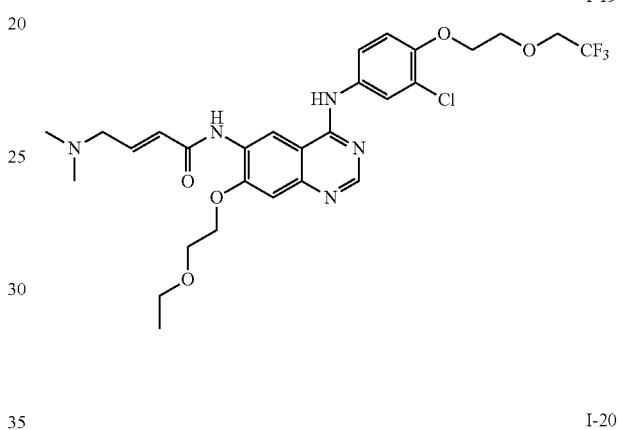
I-19
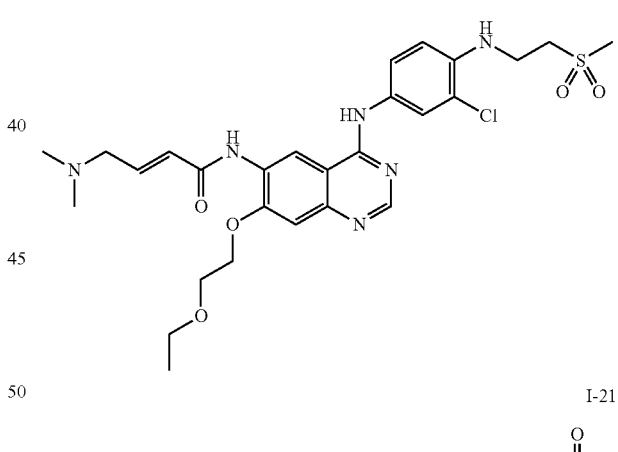
I-20
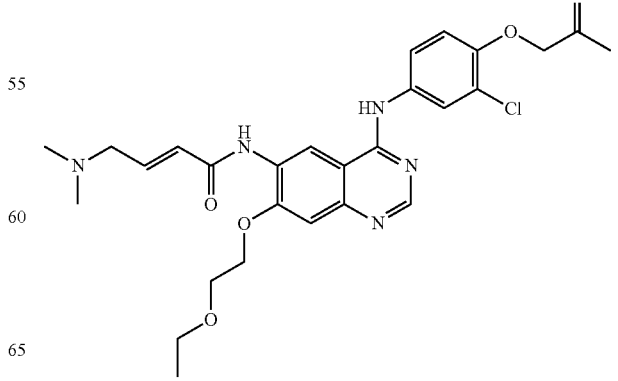
I-21

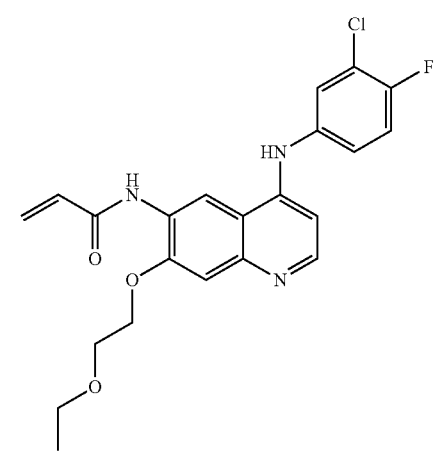
I-22
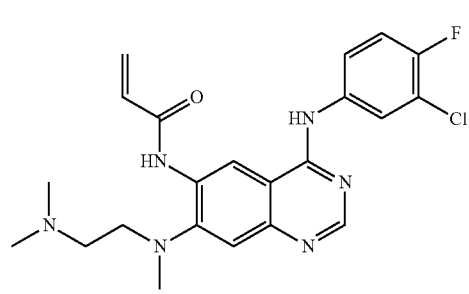
I-23
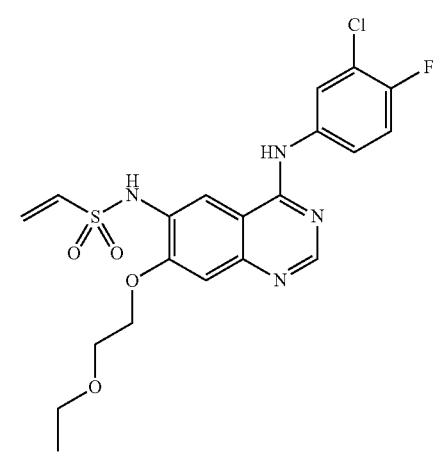
I-24
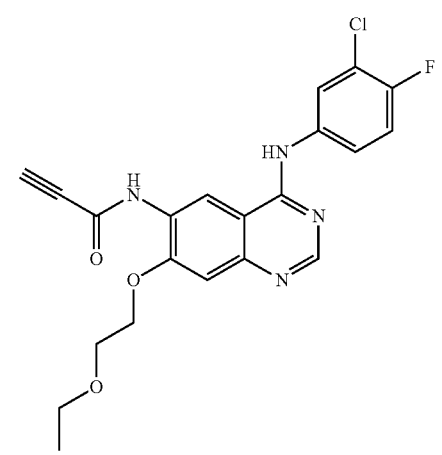
I-25
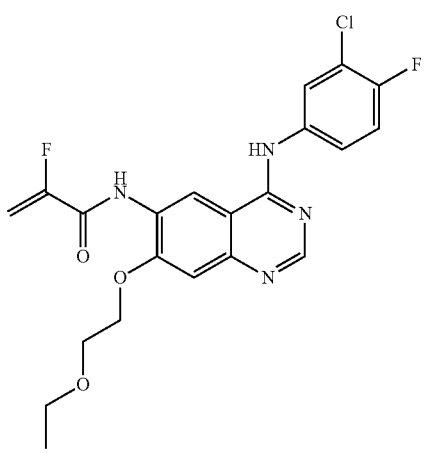
I-26
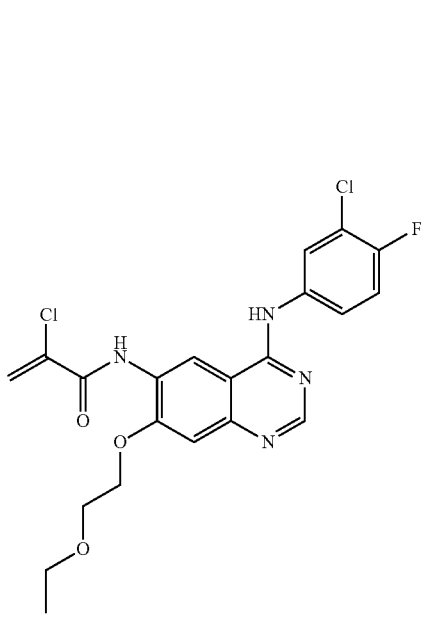
I-27
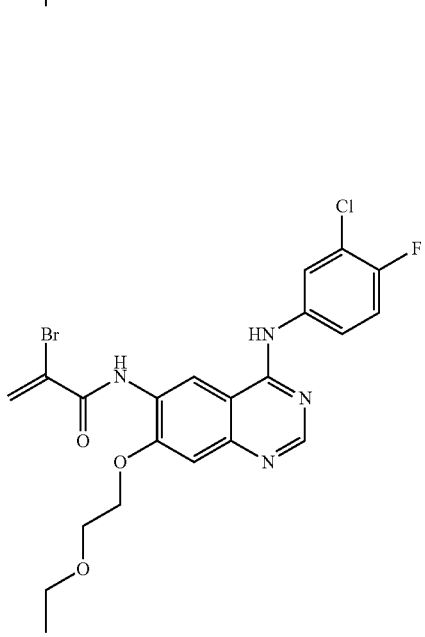
I-28

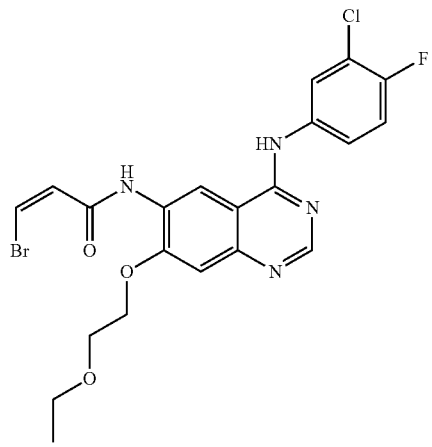
I-29
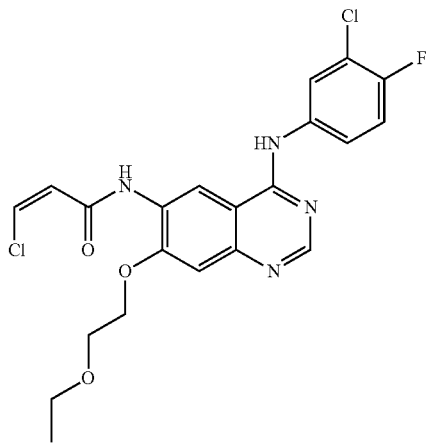
I-32
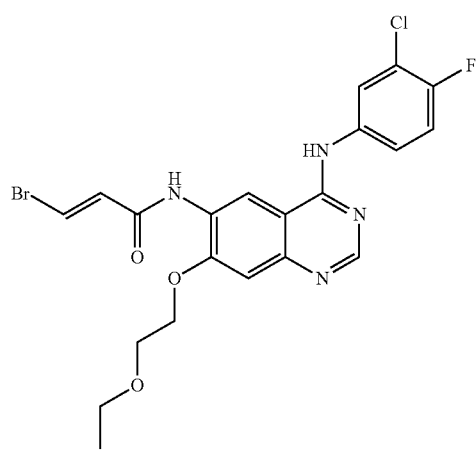
I-30
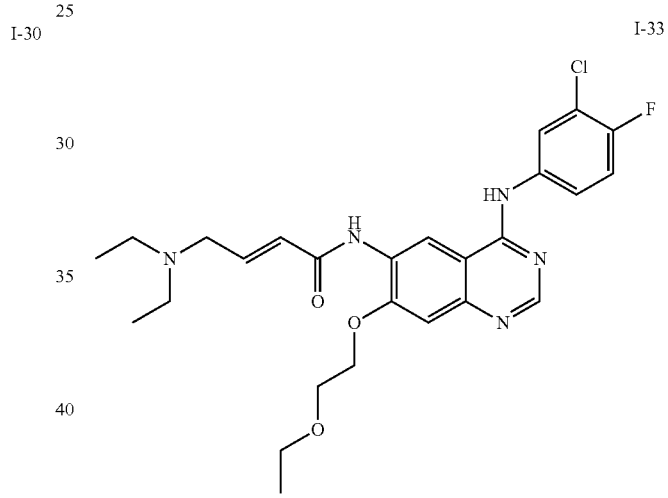
I-33
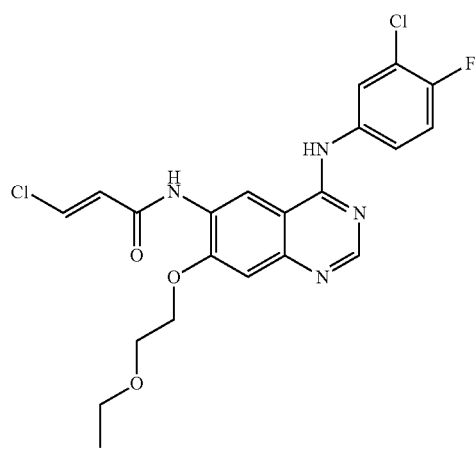
I-31
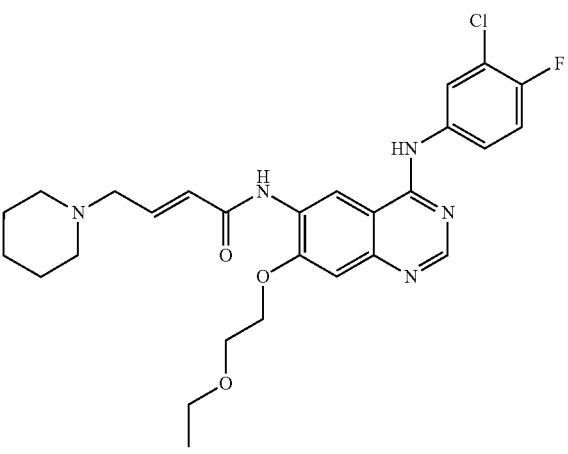
I-34

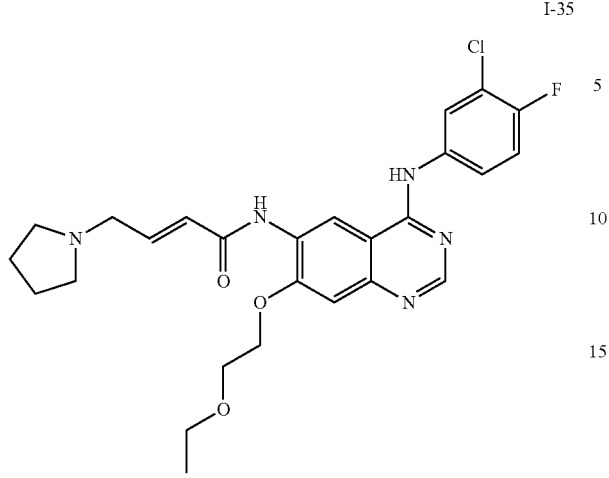

I-35

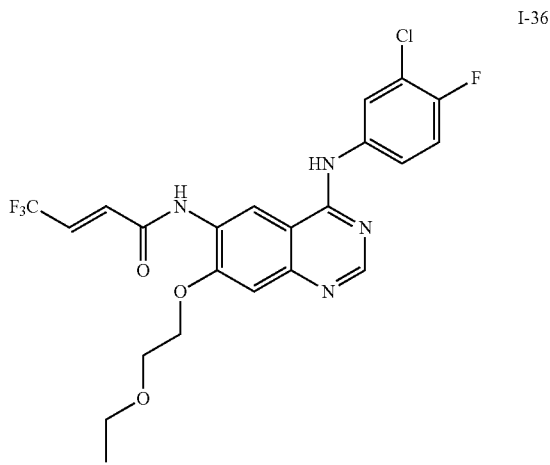

I-36

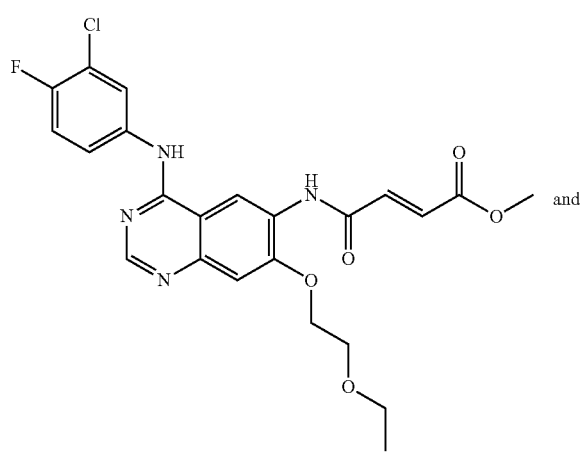

I-37 and

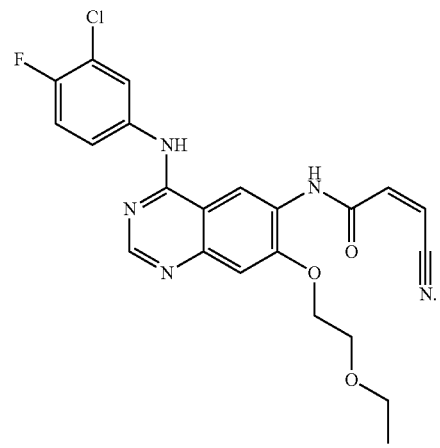

I-38

The present invention further provides a preparation method for the compound represented by general formula I, which comprises the following procedure: reacting R⁶Cl or R⁶OH with compound IV in a solvent to arrive at the general formula I by a condensation reaction;

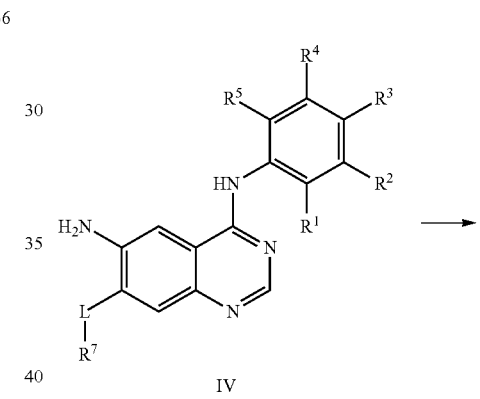

IV

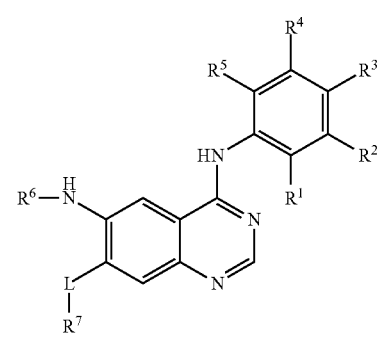

I wherein, $R^1$, $R^2$, $R^3$, $R^4$, $R^5$, $R^6$, $R^7$ and L are as previously defined.

The preparation method for the general formula I can be any method and condition that commonly used for the condensation reaction in this field, the present invention uses particularly preferably the following methods and conditions:

In the preparation method for the general formula I, the solvent is preferably an ether solvent, a polar aprotic solvent, or a chlorinated alkane solvent, the ether solvent is preferably tetrahydrofuran, the polar aprotic solvent is preferably N,N-dimethyllformamide (DMF), N-methyl-pyrrolidone (NMP) or dimethyl sulfoxide (DMSO), the chlorinated alkane solvent is preferably dichloromethane.

In the preparation method for the general formula I, the volume-to-mass ratio of the solvent to the compound IV is preferably 1 mL/g to 100 mL/g, more preferably 1 mL/g to 30 mL/g.

In the preparation method for the general formula I, the molar ratio of the $R^6Cl$ or $R^6OH$ to the compound IV is preferably 1 to 5, more preferably 3 to 4.

In the preparation method for the general formula I, the $R^6Cl$ may participate in the reaction in the form of a salt thereof, the salt of $R^6Cl$ refers to a salt formed by $R^6Cl$ with an acid, the acid can be an inorganic acid or an organic acid, the inorganic acid is preferably hydrochloric acid; the "salt of $R^6Cl$" is preferably hydrochloride of $R^6Cl$.

In the preparation method for the general formula I, when the $R^6Cl$ or the compound IV participate in the reaction in the form of a salt thereof, the reaction is carried out in the presence of a polar aprotic solvent. The polar aprotic solvent is preferably N-methyl-pyrrolidone, N,N-dimethylformamide (DMF), or dimethyl sulfoxide (DMSO). The molar concentration of the compound IV in the polar aprotic solvent is preferably 0.01M to 1.0M.

In the preparation method for the general formula I, the compound IV may participate in the reaction in the form of a salt thereof, the salt of compound IV refers to a salt formed by compound IV with an acid, the acid can be an inorganic acid or an organic acid, the inorganic acid is preferably hydrochloric acid; the "salt of compound IV" is preferably hydrochloride of compound IV.

In the preparation method for the general formula I, the temperature of the condensation reaction is preferably 0° C. to 100° C., more preferably 10° C. to 40° C.

In the preparation method for the general formula I, the process of the condensation reaction can be monitored according to the conventional test method in the field (e.g., TLC, HPLC or NMR), the reaction time of the present invention is preferably 30 min to 24 h, more preferably 30 min to 5 h.

In the preparation method for the general formula I, when the reaction substrate is $R^6OH$, the preparation method is preferably carried out in the presence of a condensation agent, and when the preparation method for the general formula I is carried out in the presence of a condensation agent, the condensation agent is preferably 1-(3-dimethylaminopropyl)-3-ethylcarbodiimide hydrochloride (EDCI), dicyclohexylcarbodiimide (DCC), 1-hydroxybenzotriazole (HOBt, CAS: 2592-95-2), 2-(7-azabenzotriazol-1-yl)-N,N,N',N'-tetramethyluronium hexafluorophosphate (HATU, CAS: 148893-10-1), 2-(7-azabenzotriazol-1-yl)-tetramethyluronium hexafluorophosphate (HBTU, CAS: 94790-37-1), $(EtO)_2P(O)N_3$, bis(2-oxo-3-oxazolidiny)phosphonic chloride (BOP-Cl, CAS: 68641-49-6), pivaloyl chloride

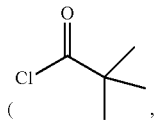

CAS: 3282-30-2), isopropyl chlorocarbonate

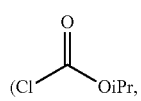

CAS: 108-23-6) or 4-toluenesulfonyl chloride (TsCl, CAS: 98-59-9); the molar ratio of the condensation agent to the $R^6OH$ is preferably 1 to 5.

Preferably the preparation method for the general formula I comprises the following post-processing steps, after the reaction is complete, a crude product is delivered by adjusting pH to ≥11 followed by extraction. The crude product can be purified by column chromatography to deliver the general formula I. The adjusting pH to ≥11 employs a base, the base is preferably an inorganic base, the inorganic base is preferably sodium hydroxide, the inorganic base can be employed in the form of a aqueous solution thereof, the mass concentration of the inorganic base aqueous solution is preferably 5% to 50%, the mass concentration refers to the percentage of the mass of the inorganic base accounted for of the total mass of the inorganic base aqueous solution. The purification method of the column chromatography can be any method and condition that commonly used for the column chromatography in this field.

In the preparation method for the general formula I, the compound IV can be prepared by the following method: reacting the compound III to arrive at the compound IV by a reduction reaction;

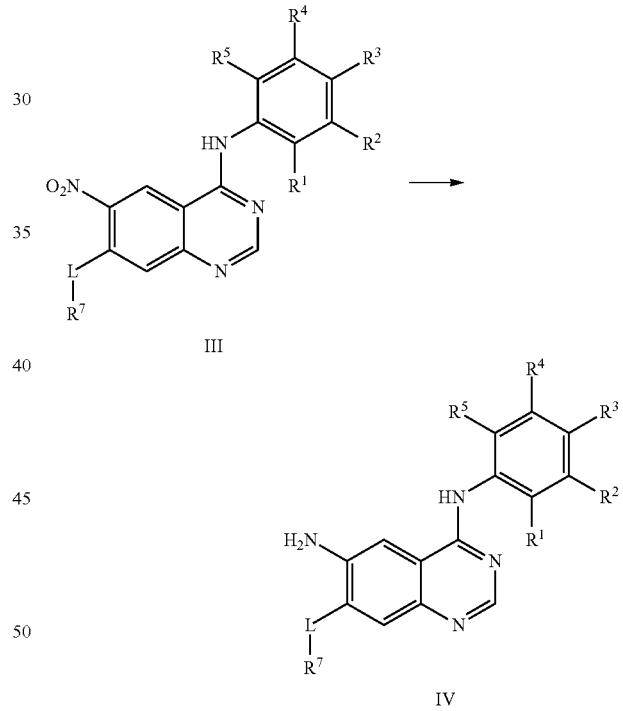

wherein, $R^1$, $R^2$, $R^3$, $R^4$, $R^5$, $R^6$, $R^7$ and L are as previously defined.

In the preparation method for the compound IV, the reduction reaction may comprises the following procedure: in the presence of an acid, reacting the compound III with a reducing reagent to arrive at the compound IV by a reduction reaction.

In the preparation method for the compound IV, the acid includes an inorganic acid and an organic acid, the inorganic acid is preferably hydrochloric acid, the hydrochloric acid can be the commercially available hydrochloric acid reagent that commonly used in the field, the mass concentration of the hydrochloric acid is preferably 30% to 37%, the mass concentration refers to the percentage of the mass of the chlorine hydride accounted for of the total mass of the hydrochloric aqueous solution; the organic acid is preferably acetic acid. The reducing reagent is preferably tin(II) chloride dehydrate or iron powder. The molar ratio of the acid to the reducing reagent is preferably 1 to 100. The molar ratio of the tin(II) chloride dehydrate to the compound III is preferably 1 to 5, more preferably 2 to 3. The temperature of the reduction reaction is preferably 0° C. to 100° C., more preferably 40° C. to 60° C. The process of the reduction reaction can be monitored according to the conventional test method in the field (e.g., TLC, HPLC or NMR), the reaction time of the present invention is preferably 30 min to 24 h, more preferably 30 min to 3 h.

Preferably the preparation method for the compound IV comprises the following post-processing steps, after the reaction is complete, the compound IV is delivered by filtration.

In the preparation method for the compound IV, the compound III can be prepared by the following method: in a solvent, reacting compound II with $R^7LH$ to arrive at the compound III in the presence of a base by a nucleophilic substitution reaction.

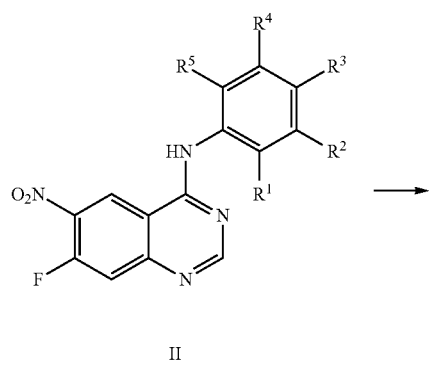

II

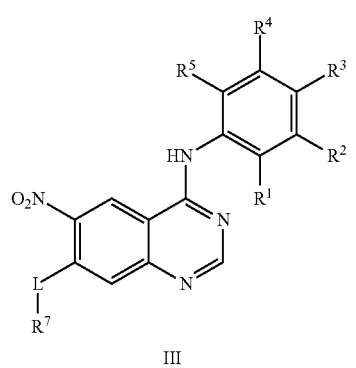

III wherein, $R^1$, $R^2$, $R^3$, $R^4$, $R^5$, $R^6$, $R^7$ and L are as previously defined.

The preparation method for the compound III can be any method that commonly used for the nucleophilic substitution in this field, the present invention uses particularly preferably the following methods and conditions:

In the preparation method for the compound III, the solvent is preferably an ether solvent and/or a polar aprotic solvent, the ether solvent is preferably tetrahydrofuran, the polar aprotic solvent is preferably N,N-dimethylformamide (DMF), N-methyl-pyrrolidone (NMP) or dimethyl sulfoxide (DMSO).

In the preparation method for the compound III, the volume-to-mass ratio of the solvent to the compound II is preferably 1 mL/g to 100 mL/g, more preferably 1 mL/g to 30 mL/g.

In the preparation method for the compound III, the base is preferably an inorganic base, the inorganic base is preferably sodium hydride, the sodium hydride can be the commercially available sodium hydride reagent that commonly used in the field, the mass percentage of the sodium hydride reagent is preferably 20% to 99%, more preferably 60% to 99%, the mass percentage refers to the percentage of the mass of the sodium hydride accounted for of the total mass of the sodium hydride reagent.

In the preparation method for the compound III, the molar ratio of the base to the compound II is preferably 1 to 10, more preferably 6 to 9.

In the preparation method for the compound III, the temperature of the nucleophilic substitution reaction is preferably −20° C. to 40° C., more preferably −15° C. to 30° C.

In the preparation method for the compound III, the process of the nucleophilic substitution reaction can be monitored according to the conventional test method in the field (e.g., TLC, HPLC or NMR), the reaction time of the present invention is preferably 30 min to 24 h, more preferably 30 min to 3 h.

Preferably, the preparation method for the compound III comprises the following procedure:

Step 1: dripping a mixture of $R^7LH$ and a solvent into a mixture of the sodium hydride and a solvent, reacting to afford a mixture;

Step 2: adding the reaction solution obtained in step 1 into a mixture of the compound II and a solvent, reacting to arrive at the compound III.

In the step 1, the temperature of the dripping is preferably −15° C. to 0° C.; the temperature of the reacting is preferably 0° C. to 40° C.

In the step 2, the temperature of the adding is preferably −15° C. to 0° C.; the temperature of the reacting is preferably 0° C. to 40° C.

In the preparation method for the compound III, the compound II can be prepared according to the following method 1 or method 2:

Method 1: reacting 7-fluoro-6-nitro-4-halogenated quinazoline with compound V in a solvent to arrive at the compound II by a condensation reaction;

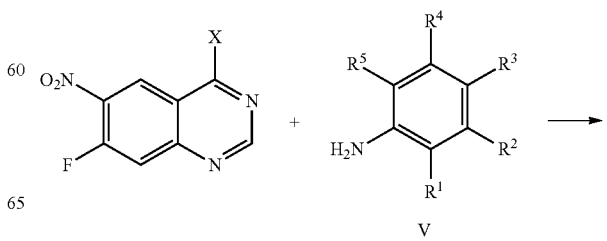

V

-continued

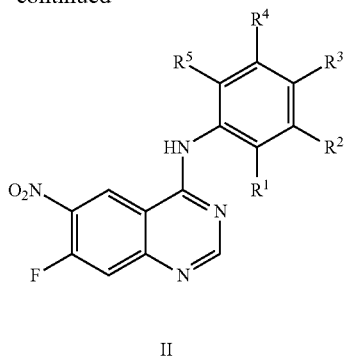

II wherein, X represents a chlorine or a bromine; $R^1$, $R^2$, $R^3$, $R^4$, $R^5$, $R^6$, $R^7$ and L are as previously defined.

Method 2: in a solvent, reacting 2-amino-4-fluoro-5-nitrobenzonitrile VII with compound V in the presence of the N,N-dimethylacetamide dimethyl acetal and the acetic acid to arrive at the compound II by a Dimroth rearrangement reaction;

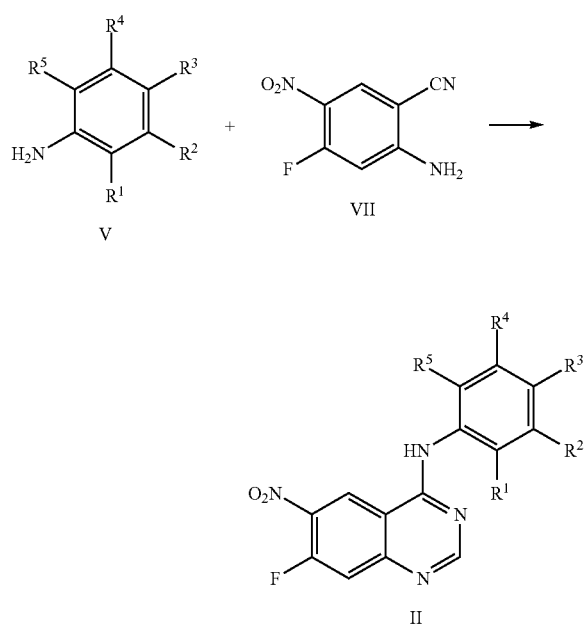

wherein, X represents a chlorine or a bromine; $R^1$, $R^2$, $R^3$, $R^4$, $R^5$, $R^6$, $R^7$ and L are as previously defined.

The preparation method 1 for the compound II can be any method that commonly used for the condensation reaction in this field, the present invention uses particularly preferably the following methods and conditions:

In the preparation method 1 for the compound II, the solvent is preferably a nitrile solvent, the nitrile solvent is preferably acetonitrile.

In the preparation method 1 for the compound II, the volume-to-mass ratio of the solvent to the 7-fluoro-6-nitro-4-halogenated quinazoline is preferably 1 mL/g to 100 mL/g, more preferably 1 mL/g to 50 mL/g.

In the preparation method 1 for the compound II, the temperature of the condensation reaction is preferably 0° C. to 100° C., more preferably 60° C. to 90° C.

In the preparation method 1 for the compound II, the process of the condensation reaction can be monitored according to the conventional test method in the field (e.g., TLC, HPLC or NMR), the reaction time of the present invention is preferably 1 h to 48 h, more preferably 10 h to 24 h.

Preferably, the preparation method 1 for the compound II comprises the following post-processing steps: after the reaction is complete, the compound II is delivered by filtration.

In the preparation method 1 for the compound II, the 7-fluoro-6-nitro-4-halogenated quinazoline can be prepared according to the following the method: reacting the 7-fluoro-6-nitro-4-hydroxyl quinazoline with a halogenating reagent to arrive at the 7-fluoro-6-nitro-4-halogenated quinazoline;

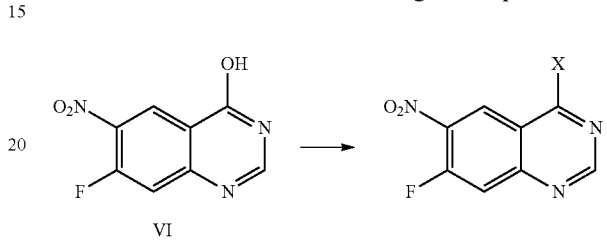

X represents a chlorine or a bromine.

In the preparation method 1 for the compound II, the preparation method for the 7-fluoro-6-nitro-4-halogenated quinazoline can be any method that commonly used for the reaction in this field, the present invention uses particularly preferably the following methods and conditions:

In the preparation method for the 7-fluoro-6-nitro-4-halogenated quinazoline, the halogenating reagent can be phosphorus oxychloride, phosphorus oxybromide or sulfoxide chloride, preferably phosphorus oxychloride or sulfoxide chloride.

In the preparation method for the 7-fluoro-6-nitro-4-halogenated quinazoline, the temperature of the reaction is preferably 100° C. to 200° C., more preferably 120° C. to 150° C.

In the preparation method for the 7-fluoro-6-nitro-4-halogenated quinazoline, the process of the reaction can be monitored according to the conventional test method in the field (e.g., TLC, HPLC or NMR), the reaction time of the present invention is preferably 1 h to 24 h, more preferably 4 h to 8 h.

In the present invention, preferably the preparation method 1 for the compound II is proceeded according to the following method: reacting the 7-fluoro-6-nitro-4-hydroxyl quinazoline with a halogenating reagent to arrive at the 7-fluoro-6-nitro-4-halogenated quinazoline, and reacting with the compound V directly without isolation and purification (i.e., an "one-pot" method) to afford the compound II by a condensation reaction;

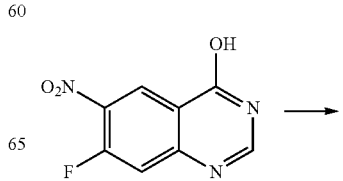

-continued

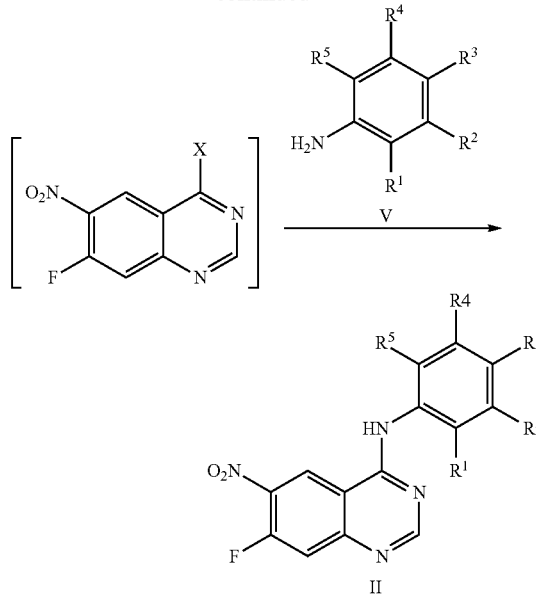

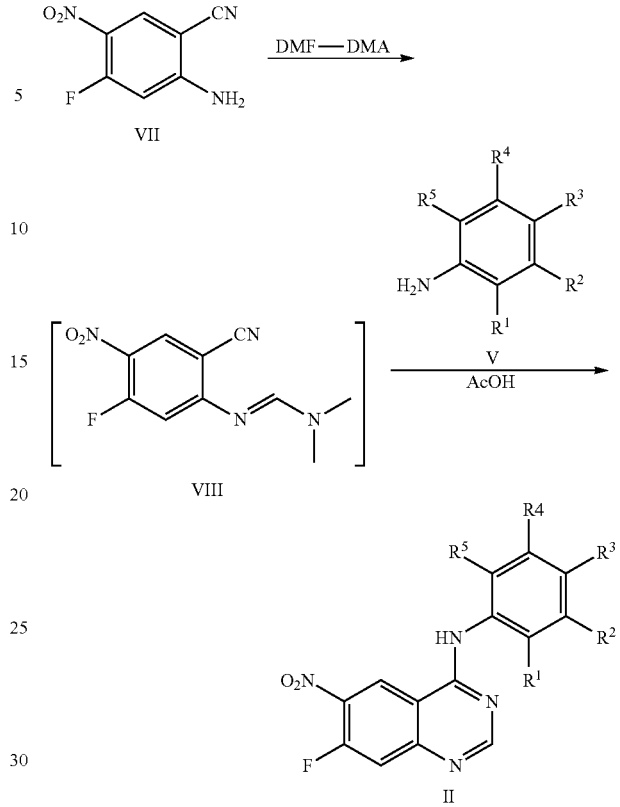

The preparation method 2 for the compound II can be any method that commonly used for the Dimroth rearrangement reaction in this field, the present invention uses particularly preferably the following methods and conditions:

In the preparation method 2 for the compound II, the reaction should be carried out in the presence of acetic acid and in a proper solvent, the solvent is preferably an aromatic solvent, the aromatic solvent includes but not limited to benzene, toluene, xylene, preferably toluene.

In the preparation method 2 for the compound II, the volume-to-mass ratio of the solvent to the 2-amino-4-fluoro-5-nitrobenzonitrile is preferably 1 mL/g to 100 mL/g, more preferably 1 mL/g to 20 mL/g.

In the preparation method 2 for the compound II, the molar ratio of the N,N-dimethylacetamide dimethyl acetal (DMF-DMA) to the 2-amino-4-fluoro-5-nitrobenzonitrile is preferably 1 to 3, more preferably 1 to 1.1.

In the preparation method 2 for the compound II, the molar ratio of the acid to the 2-amino-4-fluoro-5-nitrobenzonitrile is preferably 1 to 100, more preferably 1 to 65.

In the preparation method 2 for the compound II, the temperature of the Dimroth rearrangement reaction is preferably 0° C. to 150° C., more preferably 80° C. to 130° C., further more preferably 100° C. to 125° C.

In the preparation method 2 for the compound II, the process of the Dimroth rearrangement reaction can be monitored according to the conventional test method in the field (e.g., TLC, HPLC or NMR), the reaction time of the present invention is preferably 1 h to 24 h, more preferably 1 h to 10 h.

Preferably the preparation method 2 for the compound II is proceeded according to the following procedure: firstly reacting the 2-amino-4-fluoro-5-nitrobenzonitrile with the N,N-dimethylacetamide dimethyl acetal and the acetic acid in a solvent to arrive at an intermediate VIII; then reacting the intermediate with the compound V in the acetic acid to afford the compound II;

Preferably, the preparation method 2 for the compound II comprises the following post-processing steps: after the reaction is complete, the mixture was cooled and poured into ice water, the pH was adjusted to 9-10, into which ethyl acetate was added, filtrated to afford the compound II. The adjusted pH is preferably carried out by employing an organic base, the organic base is preferably ammonia. The ammonia can be the commercially available ammonia reagent that commonly used in the field, the mass concentration of the ammonia is preferably 5% to 50%, the mass concentration refers to the percentage of the mass of the ammonia accounted for of the total mass of the ammonia reagent.

In the preparation method 2 for the compound II, the 2-amino-4-fluoro-5-nitrobenzonitrile can be prepared according to the following method: reacting N-(2-cyano-5-fluoro-4-nitrophenyl)acetamide with an acid to arrive at the 2-amino-4-fluoro-5-nitrobenzonitrile by a hydrolysis reaction;

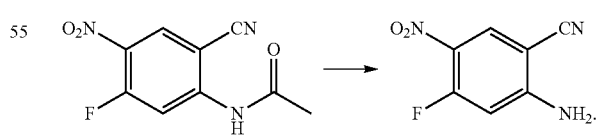

In the preparation method for the 2-amino-4-fluoro-5-nitrobenzonitrile, the hydrolysis reaction can be any method and condition that commonly used for the hydrolysis reaction in this field, the present invention uses particularly preferably the following methods and conditions:

In the preparation method for the 2-amino-4-fluoro-5-nitrobenzonitrile, the acid is preferably an inorganic acid, the inorganic acid is preferably hydrochloric acid. The hydrochloric acid can be the commercially available hydrochloric acid reagent that commonly used in the field, the mass concentration of the hydrochloric acid is preferably 30% to 37%, the mass concentration refers to the percentage of the mass of the chlorine hydride accounted for of the total mass of the hydrochloric aqueous solution.

In the preparation method for the 2-amino-4-fluoro-5-nitrobenzonitrile, the molar ratio of the acid to the N-(2-cyano-5-fluoro-4-nitrophenyl)acetamide is preferably 1 to 200.

In the preparation method for the 2-amino-4-fluoro-5-nitrobenzonitrile, the temperature of the hydrolysis reaction is preferably 40° C. to 80° C., more preferably 60° C. to 70° C.

In the preparation method for the 2-amino-4-fluoro-5-nitrobenzonitrile, the process of the hydrolysis reaction can be monitored according to the conventional test method in the field (e.g., TLC, HPLC or NMR), and typically with the depletion of the 2-amino-4-fluoro-5-nitrobenzonitrile as the terminal point of the reaction, the reaction time is preferably 1 h to 24 h, more preferably 1 h to 5 h.

In the preparation method for the 2-amino-4-fluoro-5-nitrobenzonitrile, the N-(2-cyano-5-fluoro-4-nitrophenyl)acetamide can be prepared according to the following method: in the presence of conc. sulfuric acid, reacting conc. nitric acid with N-(2-cyano-5-fluorophenyl)acetamide to arrive at the N-(2-cyano-5-fluoro-4-nitrophenyl)acetamide by a nitration reaction;

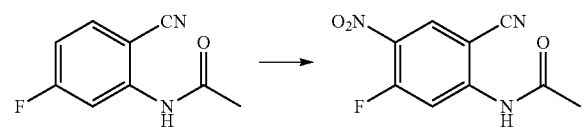 [SMILES: CC(=O)Nc1cc(F)ccc1C#N ; CC(=O)Nc1cc(F)c([N+](=O)[O-])cc1C#N]

In the preparation method for the N-(2-cyano-5-fluoro-4-nitrophenyl)acetamide, the nitration reaction can be any method and condition that commonly used for the nitration reaction in this field, the present invention uses particularly preferably the following methods and conditions:

In the preparation method for the N-(2-cyano-5-fluoro-4-nitrophenyl)acetamide, the volume ratio of the conc. sulfuric acid to the conc. nitric acid is preferably 1 to 5, more preferably 2 to 3.

In the preparation method for the N-(2-cyano-5-fluoro-4-nitrophenyl)acetamide, the conc. sulfuric acid can be the commercially available conc. sulfuric acid reagent that commonly used in the field, the mass concentration of the conc. sulfuric acid is preferably 98%, the mass concentration refers to the percentage of the mass of the sulfuric acid accounted for of the total mass of the conc. sulfuric acid reagent.

In the preparation method for the N-(2-cyano-5-fluoro-4-nitrophenyl)acetamide, the volume-to-mass ratio of the conc. nitric acid to the N-(2-cyano-5-fluorophenyl)acetamide is preferably 1 mL/g to 10 mL/g, more preferably 1 mL/g to 3 mL/g.

In the preparation method for the N-(2-cyano-5-fluoro-4-nitrophenyl)acetamide, the temperature of the nitration reaction is preferably 0° C. to 40° C., more preferably 10° C. to 30° C.

In the preparation method for the N-(2-cyano-5-fluoro-4-nitrophenyl)acetamide, the process of the nitration reaction can be monitored according to the conventional test method in the field (e.g., TLC, HPLC or NMR), and typically with the depletion of the N-(2-cyano-5-fluorophenyl)acetamide as the terminal point of the reaction, the reaction time is preferably 1 h to 24 h, more preferably 1 h to 5 h.

In the preparation method for the N-(2-cyano-5-fluoro-4-nitrophenyl)acetamide, the N-(2-cyano-5-fluorophenyl)acetamide can be prepared according to the following method: in an organic solvent, in the presence of a base, reacting 2-amino-4-fluorobenzonitrile and acetic anhydride to arrive at the N-(2-cyano-5-fluorophenyl)acetamide by a condensation reaction;

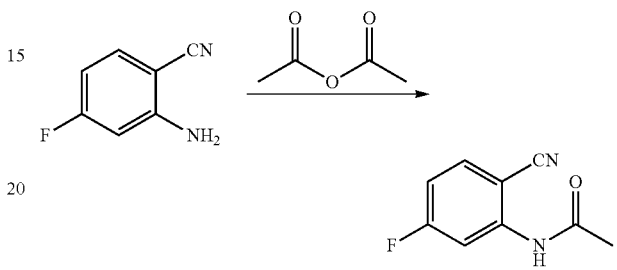

In the preparation method for the N-(2-cyano-5-fluorophenyl)acetamide, the condensation reaction can be any method and condition that commonly used for the nitration reaction in this field, the present invention uses particularly preferably the following methods and conditions:

In the preparation method for the N-(2-cyano-5-fluorophenyl)acetamide, the organic solvent is preferably a halogenated hydrocarbon solvent, the halogenated hydrocarbon solvent is preferably a chlorinated hydrocarbon solvent, the chlorinated hydrocarbon solvent is preferably dichloromethane.

In the preparation method for the N-(2-cyano-5-fluorophenyl)acetamide, the volume-to-mass ratio of the organic acid to the 2-amino-4-fluorobenzonitrile is preferably 1 mL/g to 100 mL/g, more preferably 1 mL/g to 20 mL/g.

In the preparation method for the N-(2-cyano-5-fluorophenyl)acetamide, the molar ratio of the acetic anhydride to the 2-amino-4-fluorobenzonitrile is preferably 1 to 5, more preferably 1 to 2.

In the preparation method for the N-(2-cyano-5-fluorophenyl)acetamide, the base is preferably an organic base, the organic base is preferably trimethylamine.

In the preparation method for the N-(2-cyano-5-fluorophenyl)acetamide, the molar ratio of the base to the 2-amino-4-fluorobenzonitrile is preferably 0.01 to 1, more preferably 0.1 to 0.5.

In the preparation method for the N-(2-cyano-5-fluorophenyl)acetamide, the temperature of the condensation reaction is preferably 0° C. to 40° C., more preferably 10° C. to 30° C.

In the preparation method for the N-(2-cyano-5-fluorophenyl)acetamide, the process of the condensation reaction can be monitored according to the conventional test method in the field (e.g., TLC, HPLC or NMR), and generally with the depletion of the 2-amino-4-fluorobenzonitrile as the terminal point of the reaction, the reaction time is preferably 1 h to 24 h, more preferably 2 h to 6 h.

In the present invention, preferably the compound represented by general formula I is prepared using the following route 1 or route 2:

Route 1:
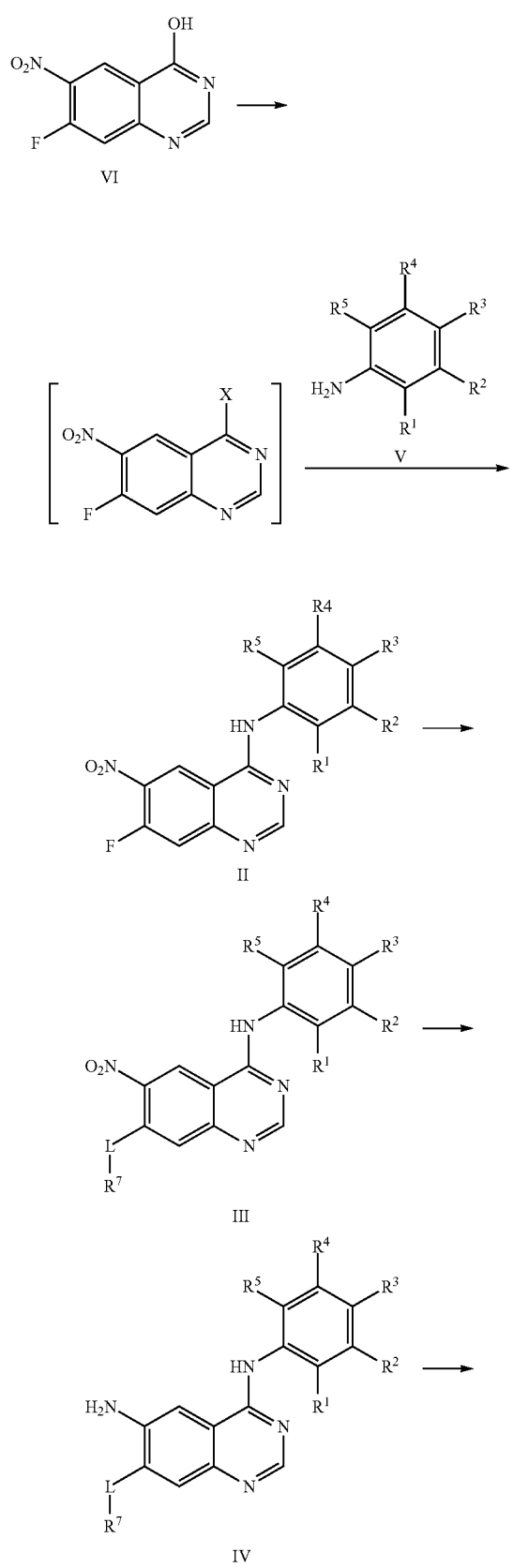
Route 2:
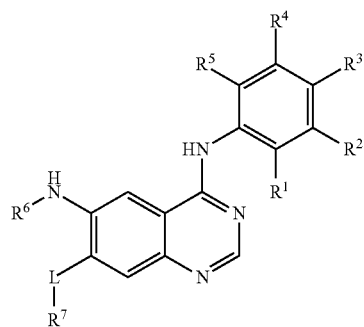
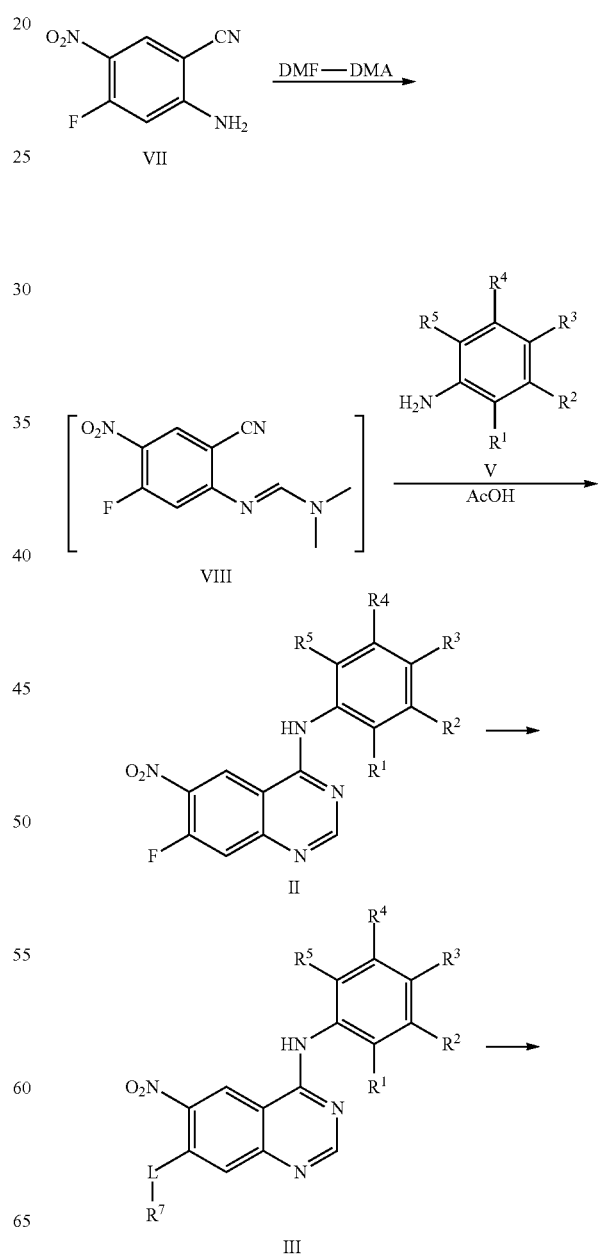

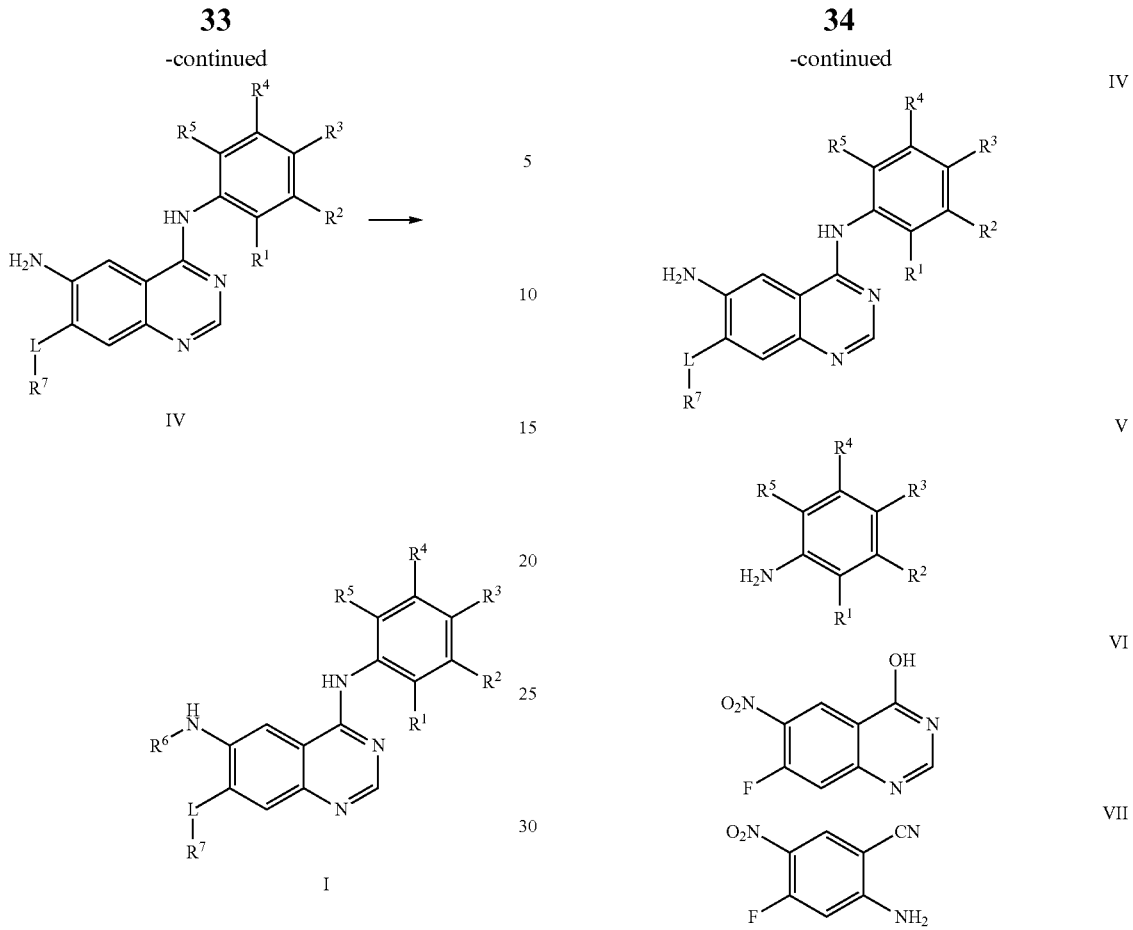

The present invention also provides the compound II, III, IV, V, VI or VII, wherein, $R^1$, $R^2$, $R^3$, $R^4$, $R^5$, $R^6$, $R^7$ and L are as previously defined.

The present invention also provides an application of the compound represented by general formula I, the pharmaceutical acceptable salt thereof, the stereoisomer or the solvate thereof in manufacturing a medicament, which may be administered alone or be administered in combination with other therapeutic agents. The medicament is used to treat and/or prevent diseases or conditions associated with receptor tyrosine kinases in mammals (including humans). The diseases or conditions associated with receptor tyrosine kinases in mammals (including humans) include but not limited to the proliferation and migration of tumor cells mediated by receptor tyrosine kinases or driven by receptor tyrosine kinases. The drug combination includes but not limited to nitrogen mustard, aziridine, methyl melamine, sulfonic acid alkyl ester, nitrosourea, triazene, folic acid analogue, pyrimidine analogue, purine analogue, vinca alkaloid, epipodophyllotoxins, antibiotics, topoisomerase inhibitor, anticancer vaccine, acivicin, aclarubicin, acodazole hydrochloride, acronine, adozelesin, aldesleukin, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, mesylate bisnafide, bizelesin, bleomycin sulfate, busulfan, actinomycin-C, calusterone, caracemide, carbetimer, carboplatin, carmustine, carubicin hydrochloride, idarubicin hydrochloride, ifosfamide, interleukin-II, interferon alpha-2a, interferon alpha-2b, irinotecan hydrochloride, letrozole, mercaptopurine, methotrexate, metoprine, mitomycin, mitoxantrone, paclitaxel, procarbazine, pethidine, vincaleukoblastinum, vincristine, angiogenesis inhibitor, camptothecin, dexamethasone, aspirin, acetyl aminophenol, indometacin, ibuprofen, ketoprofen, meloxicam, corticosteroid and adrenocortical steroid.

The present invention further provides a pharmaceutical composition comprising the compound represented by general formula I, the pharmaceutically acceptable salt thereof, the stereoisomer thereof or the solvate thereof, in association with one or more of pharmaceutically acceptable carriers or excipients.

In certain embodiments, the pharmaceutical composition of the present invention includes but not limited to physiologically acceptable surfactants, carriers, diluents, excipients, lubricants, suspensions, film forming materials, coating additives or combinations thereof, and the compound of the present invention, the acceptable carriers or diluents for therapeutic use are well known in the field of medicine.

The pharmaceutical composition of the present invention, may be manufactured according to the formulations and used as the following dosage forms: tablets, capsules or elixirs for oral administration, suppositories for rectal administration, sterile solutions, suspensions for injection administration, patches and subcutaneous deposits for cutaneous penetration administration, etc. The injections may be formulated according to the following conventional forms: solutions or suspensions, solid formulations which suitable to prepare solutions or suspensions before injection, or emulsions. Suitable excipients are, e.g. water, saline, glucose, mannitol, lactose, lecithin, albumin, sodium glutamate, cysteine hydrochloride, etc. In addition, if desired, the pharmaceutical composition for injection may comprise a relatively small amount of non-toxic adjuvants, such as wetting agents, pH buffer and the like. If desired, an absorption enhancer (e.g. liposome) may also be used.

Preparations for parenteral administration include aqueous solutions of active compounds in the form of water soluble. Additionally, the suspensions of active compounds may be formulated into suitable oil suspension injections. Suitable lipophilic solvents or carriers include fatty oils such as sesame oil, or other organic oils such as soybean oil, grapefruit oil or apricot kernel oil, or synthetic aliphatic esters such as ethyl oleate or triglyceride, or liposome. Aqueous suspension injections may include a substance that enhances the viscosity of the suspension, such as carboxymethylcellulose sodium, sorbitol or dextran. Optionally, the suspensions may include a suitable stabilizer or a reagent that enhances the solubility of the compound, to enable the preparation for solutions with high concentration.

The medicinal preparations for oral administration may obtained according to the following method: combing the active compound with a solid excipient, optionally milling the resulting mixture, and processing the particle mixture, if desired, to give a tablet or sugarcoated agent after adding a suitable adjuvant. Suitable excipients are, specifically, a filler such as a sugar including lactose, sucrose, mannitol or sorbitol; a cellulose preparation such as cornstarch, wheaten starch, rice starch, potato starch, gelatin, gum tragacanth, methyl cellulose, hydroxypropyl methyl cellulose, carboxymethyl cellulose sodium, and/or polyvinyl pyrrolidone (PVP). If desired, a disintegrating agent such as crosslinked polyvinylpyrrolidone, agar or alginic acid or alginate such as sodium alginate may be added. Suitable coating for the sugarcoated agent is made. For this purpose, a conc. sugar solution may be employed, the solution may optionally include arabic gum, talc, polyvinyl pyrrolidone, carboxyvinyl polymer gel, polyethylene glycol and/or titanium dioxide, a solution of shellac varnish, and a suitable organic solvent or a solvents mixture. A dye or pigment may be added into the tablet or sugarcoated agent in order to identify or indicate characteristics for the different combinations of the active compound doses. The preparations may be manufactured according to methods well known in the art.

The present invention also relates to various pharmaceutical compositions known in the pharmaceutical field which are used for intraocular, intranasal and intra-aural delivery. The pharmaceutical formulation comprises aqueous ophthalmic solution of the active compound, which may be in a water-soluble form such as guttae ophthalmicae, or a gellan gum or hydrogel; ophthalmic ointment; ophthalmic suspension, such as particulate, drug-contained small polymeric particles suspended in a liquid carrier medium, fat soluble preparations, and microspheres; and ocular inserts. For stability and comfort, these suitable pharmaceutical preparations are most frequently and preferably manufactured to sterile, isotonic and buffered preparations. The pharmaceutical composition also includes drops and sprays, which often simulate nasal secretions to ensure the maintenance of normal cilia function in many respects. As a person skilled in the art knows that, suitable preparations are most frequently and preferably isotonic, with a mild buffer of pH 5.5 to 6.5, and most frequently and preferably include an antimicrobial preservative and a suitable drug stabilizer. The pharmaceutical preparations used for entotic infusion include a suspension and an ointment entotic locally applied. The common solvents for these entotic preparations include glycerol and water.

The present invention also provides medicaments manufactured by the compound represented by general formula I, or the pharmaceutical acceptable salt thereof or the stereoisomer thereof or the solvate, which can be administrated to mammals such as humans in the administration routes of oral, parenteral (intravenous, intramuscular, subcutaneous, etc.), lung, topical, skin, etc. The dose for human of the compound in the present invention is ranged from about 0.1 mg to about 1000 mg.

In certain embodiments, examples of receptor tyrosine kinase mediated diseases and conditions include but not limited to inflammatory disease or condition, immune disease or condition, hyperplasia disease or condition, as well as degenerative disease or condition.

It can be expected that, examples of EGFR receptor tyrosine kinase mediated diseases and conditions in whose treatment the compound of the present invention can be used for include but not limited to head cancer, thyroid carcinoma, neck cancer, eye cancer, skin cancer, oral cancer, throat cancer, esophageal cancer, thymic carcinoma, bone cancer, leukemia, myeloma, lung cancer, colon cancer, sigmoid colon cancer, rectal cancer, gastric cancer, prostate cancer, breast cancer, ovarian cancer, kidney cancer, liver cancer, pancreatic cancer, brain cancer, colon cancer, cardiac carcinoma, adrenal carcinoma, subcutaneous carcinoma, lymph node cancer, melanoma, glioblastoma, HIV, hepatitis, adult respiratory distress syndrome, bone loss disease, chronic obstructive pulmonary disease, chronic pneumonia, dermatitis, inflammatory skin disease, atopic dermatitis, cystic fibrosis, septic shock, metastasizing septicemia, endotoxic shock, hemodynamic shock, sepsis syndrome, ischemic reperfusion injury, meningitis, psoriasis, fibrotic disease, cachexia, graft versus host disease rejection, autoimmune disease, rheumatoid spondylitis, arthrophlogosis diseases (such as rheumatoid arthritis or osteoarthritis), osteoporosis, Crohn's disease, ulcerative colitis, esoenteritis, multiple sclerosis, systemic lupus erythematosus, erythema nodosum leprosum in leprosy (ENL), radiation injury, asthma, oxygen rich induced lung injury, microbial infection and microbial infection syndrome.

The present invention also provides a method for treating and/or preventing diseases or conditions associated with receptor tyrosine kinases in mammals (including humans), which comprises the following process: administrating to a person in need with an effective amount of the pharmaceutical composition; the pharmaceutical composition comprises the compound represented by general formula I, or the pharmaceutical acceptable salt thereof or the stereoisomer or the solvate thereof, in association with one or more pharmaceutically acceptable carriers or excipients. The diseases or conditions associated with receptor tyrosine kinases include but not limited to the proliferation and migration of tumor cells mediated by receptor tyrosine kinases or driven by receptor tyrosine kinases.

The present invention is further illustrated in details below, the various terms and phrases used in the present invention have the general meanings well known to a person skilled in the art, but if any special definition occurs in this disclosure, it should be taken to be correct meaning of the subject.

The term "polar aprotic solvent" of the present invention refers to a solvent with a dielectric constant of more than 15, a dipole moment of more than 2.5 D, and the bonding between the intermolecular hydrogen atom and the intramolecular atom is firm and which is not easy to give a proton.

In the present invention, the term "halogen" refers to fluorine, chlorine, bromine or iodine.

In the present invention, the term "alkyl" refers to a linear or branched saturated hydrocarbon group, examples of which including but not limited to methyl, ethyl, n-propyl, iso-propyl, n-butyl, iso-butyl, sec-butyl, tert-butyl, n-amyl, iso-amyl, 2-methylbutyl, neo-amyl, 1-ethylpropyl, n-hexyl, iso-hexyl, 4-methylpentyl, 3-methylpentyl, 2-methylpentyl, 2-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl, etc.

In the present invention, the term "alkenyl" refers to a linear or branched unsaturated hydrocarbon group with at least one of carbon-carbon double bond, examples of which including but not limited to vinyl, propenyl, allyl, butenyl, pentenyl, penta-1,4-dienyl, etc.

In the present invention, the term "alkynyl" refers to a linear or branched unsaturated hydrocarbon group with at least one of carbon-carbon triple bond, examples of which including but not limited to ethynyl, propynyl, propargyl, butynyl, pentynyl, hexynyl, etc.

In the present invention, the term "cycloalkyl" refers to an all-carbon monocyclic or a polycyclic group, wherein each ring does not contain a double bond. Preferably a cycloalkyl of 1-3 of rings formed with 3-20 of carbon atoms, more preferably 3-10 of carbon atoms, for example: cyclopropyl, cyclobutyl, cyclopentyl, cyclohexyl, cycloheptyl, cyclooctyl, cyclodecanyl and cyclododecyl.

In the present invention, the term "hydroxyl" refers to

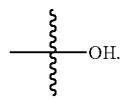

In the present invention, the term "amino" refers to

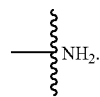

In the present invention, the term "cyano" refers to

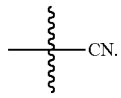

In the present invention, the term "alkyl sulphanyl" refers to a group formed by bonding an alkyl with a sulfur atom, i.e.

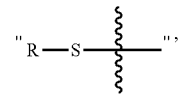

R represents an alkyl.

In the present invention, the term "alkoxyl" refers to a group formed by bonding an alkyl with an oxygen atom, i.e.

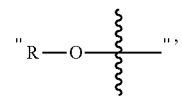

R represents an alkyl.

In the present invention, the term "aryl" refers to any stable mono- or di-cyclic carboatomic rings, each one of which containing more than 7 atoms, and at least one of which is aromatic; examples of the aryl unit include phenyl, naphthyl, tetralyl, 2,3-dihydroindenyl, biphenylyl, phenanthryl, anthryl or acenaphthyl. It will be understood that in the case where the aryl group is a di-cyclic substituent, and one of the rings is nonaromatic, the bonding is located on the aromatic one.

In the present invention, the term "heteroaryl" refers to any stable mono- or di-cyclic carboatomic rings, each one of which containing more than 7 atoms, and at least one of which is an aromatic ring and contains 1-4 of heteroatoms selected from the group consisting of O, N and S; examples of the heteroaryl within the scope of this definition include but not limit to acridinyl, carbazolyl, cinnolinyl, quinoxalinyl, pyrazolyl, indolyl, benzotriazolyl, furyl, thienyl, benzothienyl, benzofuryl, quinolyl, isoquinolyl, oxazolyl, isoxazoyl, indolyl, pyrazinyl, pyrizazinyl, pyridyl, pyrimidyl, pyrrolyl, tetrahydroquinolyl.

In the present invention, the term "pharmaceutically acceptable salt" refers to a salt within the scope of reliable medical judgment, which is suitable for use in contact with tissues of humans and animals but without excessive toxicity, irritation, allergic reactions, etc., and has a reasonable effect/risk ratio, including an acid addition salt and alkali addition salt. The acid addition salt comprises a salt formed with an inorganic acid, which including but not limited to hydrochloride, hydrobromide, sulfate, bisulfate and nitrate, etc.; a salt formed with an organic acid, which including but not limited to tartrate, formate, acetate, lactate, citrate, trichloroacetate, trifluoroacetate and benzoate, etc.; a salt formed with sulfonic acid such as methanesulfonate, benzene sulfonate, tosylate, naphthalenesulfonate and the like. The alkali addition salt includes but not limited to a salt formed with an alkali metal such as sodium, potassium, etc., an alkaline-earth metal such as calcium, magnesium zinc, etc., ammonium salt; and a salt formed with nitrogenous organic alkali, which including but not limited to trimethyl amine, triethyl amine, tributyl amine, pyridine, N,N-dimethyl aniline, N-methyl piperidine, N-methyl morpholine, diethyl amine, dicyclohexyl amine, dibenzyl amine, N-benzyl-β-phenylethyl amine, 1-diphemin, N,N-dibenzyl ethylene diamine, etc. In the present invention, the "pharmaceutically acceptable salt" is preferably selected from hydrochloride, sulfate, methanesulfonate, toluenesulfonate, fumarate, maleate, malate and benzoate.

In the present invention, the term "pharmaceutical composition" refers to a product comprising a specified amount of each specified component, and any product produced directly or indirectly from a combination of a specified amount of each specified component.

In the present invention, the term "solvate" refers to a hydrate, an alcohol-adduct or other organic solvent-adduct.

In the present invention, the term "stereoisomer" refers to racemate, enantiomer, diastereomer or enantiomer-enriched mixture.

In the present invention, the substituent of "$C_{x1}$-$C_{y1}$" in which the range of the carbon numbers are determined (x1 and y1 are integers), e.g., "$C_{x1}$-$C_{y1}$" alkyl, "$C_{x1}$-$C_{y1}$" alkyoxy, "$C_{x1}$-$C_{y1}$" aryl, "$C_{x1}$-$C_{y1}$" heteroaryl or "$C_{x1}$-$C_{y1}$" alkyoxycarbonyl, all refers to the numbers of carbon that do not contain the substituent, for example, the $C_1$-$C_6$ alkyl refers to a $C_1$-$C_6$ alkyl that does not contain the substituent.

The mentioned optimized conditions can be optionally combined in accordance with the general knowledge in this field to obtain preferred embodiments.

The reagents and the raw materials used herein are commercially available.

In the present invention, the room temperature refers to ambient temperature, i.e. 10° C. to 35° C.

The positive effects of the present invention are as follows: the present invention has found a class of quinazoline derivatives with an irreversible inhibitory of EGFR in the development of medicaments with excellent anti-tumor effect, reduced drug resistance and well-tolerated, which has a unique chemical structure, is characterized by irreversibly inhibiting EGFR tyrosine kinase, has high biological activity, apparently improves the inhibiting effect on the EGFR tyrosine kinase, has quite strong tumor inhibiting effect on tumor cells and a transplantation tumor pathological model of animal tumors, and has good market developing prospects.

DETAILED DESCRIPTION OF THE PREFERRED EMBODIMENT

The following preparation examples and biological examples of the compounds further illustrate the present invention, which are mainly intended to be explained concretely in more details, rather than be limited in any forms.

Embodiment 1: Synthesis of (E)-N-(4-(3-chloro-4-fluorophenylamino)-7-(3-methoxypropoxy)quinazolin-6-yl)-4-(dimethylamino)but-2-enamide (Compound 1)

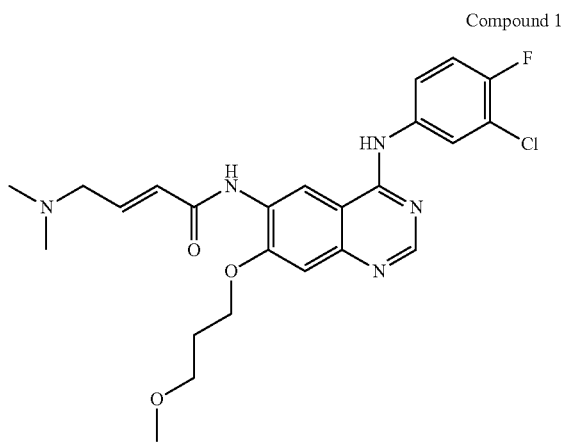 [SMILES: COCCCOc1cc2ncnc(Nc3ccc(F)c(Cl)c3)c2cc1NC(=O)/C=C/CN(C)C]

Compound 1 a. Synthesis of N-(3-chloro-4-fluorophenyl)-7-fluoro-6-nitro-4-quinazolinamine

Method 1 (One-Pot Reaction):

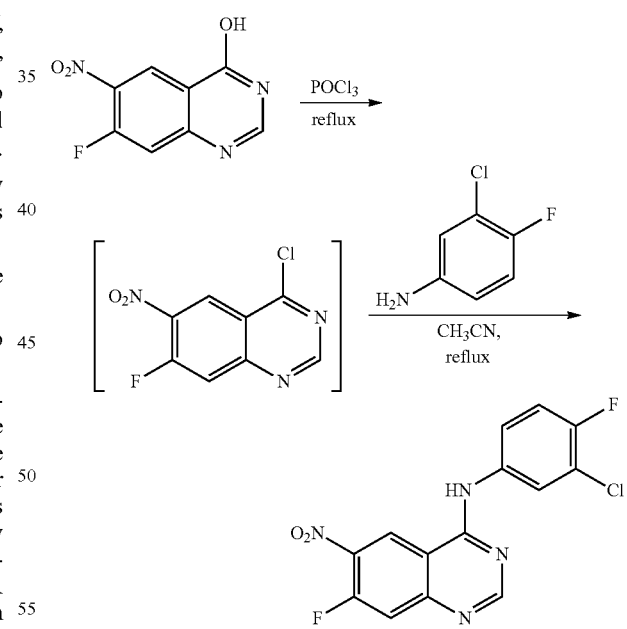

Compound 7-fluoro-6-nitro-4-hydroxyquinazoline (5 g, 23.9 mmol) was added into a 100 mL one-neck flask, then phosphorus oxychloride (44.6 mL, 478 mmol) was added, heated to reflux at 150° C. for 5 h, the phosphorus oxychloride in the reaction solution was evaporated, the residue was diluted with anhydrous dichloromethane and evaporated again. Repeat the procedure for 3 times and diluted with acetonitrile (100 mL), then compound 3-chloro-4-fluoroaniline (2.3 g, 15.8 mmol) was added. A yellow solid was precipitated after heating at reflux overnight. The yellow solid in the reaction solution was filtrated and dried to deliver the product N-(3-chloro-4-fluorophenyl)-7-fluoro-6-nitro-4-quinazolinamine (4.8 g, 56% yield). ¹H-NMR (d-DMSO, 400 MHz, δ ppm): 10.61 (br, 1H), 9.68 (d, J=10.8 Hz, 1H), 8.81 (s, 1H), 8.10-8.13 (d, J=7.6 Hz, 1H), 8.05-8.07 (d, J=8 Hz, 1H), 7.81-7.85 (m, 1H), 7.50-7.54 (d, J=8 Hz, 1H).

Method 2 (Dimroth Rearrangement Reaction):

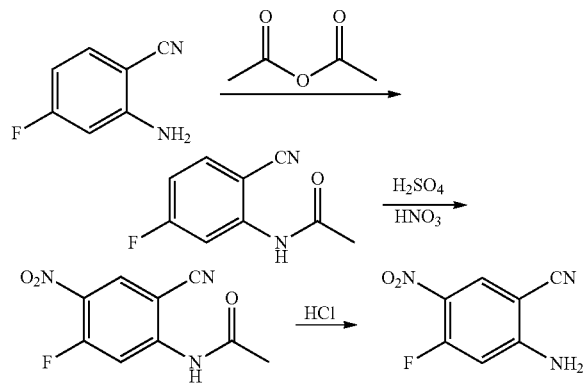

2-Amino-4-fluorobenzonitrile (13.6 g, 100 mmol) was dissolved in dichloromethane (130 mL) at room temperature, acetic anhydride (10.7 g, 105 mmol) and triethylamine (5 mL) were added while stirring, the reaction mixture was reacted for 6 h, water (200 mL) was added, the organic phase was separated, dried, filtrated and concentrated to deliver N-(2-cyano-5-fluorophenyl)acetamide (17 g, 96% yield). ¹H-NMR (MeOD, 400 MHz, δ ppm): 7.53 (m, 1H), 7.47 (m, 1H), 6.91 (m, 1H), 2.10 (s, 3H).

100 mL conc. sulfuric acid and 35 mL conc. nitric acid were added into a 250 mL flask, N-(2-cyano-5-fluorophenyl)acetamide (17 g, 96 mmol) was added at 0° C., the reaction solution was heated to 20° C., after stirring to react for 3 h, then poured into ice-water, filtrated, dried to deliver N-(2-cyano-5-fluoro-4-nitrophenyl)acetamide (12.8 g, 60% yield). ¹H-NMR (MeOD, 400 MHz, δ ppm): 8.42 (d, J=10.8 Hz, 1H), 7.79 (m, 1H), 2.11 (s, 3H).

N-(2-cyano-5-fluoro-4-nitrophenyl)acetamide (12.8 g, 57 mmol) was dissolved in conc. hydrochloric acid (37% concentration, 300 mL), heated to 65° C., and reacted for 2 h, the reaction solution was concentrated and a saturated sodium bicarbonate solution was added, extracted with ethyl acetate, dried over anhydrous sodium sulphate, purified by column chromatography to deliver 2-amino-4-fluoro-5-nitrobenzonitrile (7.2 g, 70% yield). ¹H-NMR (MeOD, 400 MHz, δ ppm): 8.17 (d, J=10.8 Hz, 1H), 6.61 (m, 1H). ESI-MS (m/z): 182.1 [M+H]⁺.

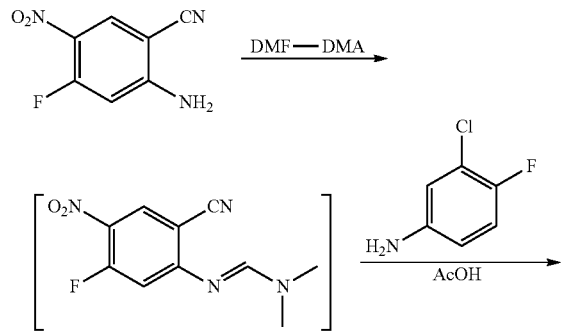

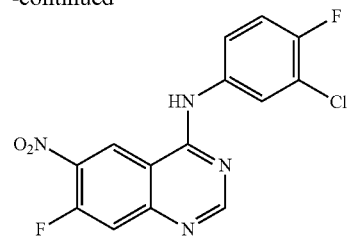

Compound 2-amino-4-fluoro-5-nitrobenzonitrile (7.2 g, 40 mmol) was dissolved into toluene (70 mL), DMF-DMA (N,N-dimethylformamide dimethyl acetal, 4.7 g, 40 mmol) and acetic acid (1 mL) was added, stirring to react at 105° C. for 2 h, after concentration by evaporation, acetic acid (140 mL) and 3-chloro-4-fluoroaniline (6.9 g, 48 mmol) were added, stirring to react at 125° C. for 3 h. The reaction mixture was cooled to room temperature, poured into ice-water, after the pH value was adjusted to 9 with ammonia, then ethyl acetate 40 mL was added, stirred for 1 h, filtrated, dried to deliver the product N-(3-chloro-4-fluorophenyl)-7-fluoro-6-nitro-4-quinazolinamine (8.3 g, 62% yield). ¹H-NMR (d-DMSO, 400 MHz, δ ppm): 10.61 (br, 1H), 9.68 (d, J=10.8 Hz, 1H), 8.81 (s, 1H), 8.10-8.13 (d, J=7.6 Hz, 1H), 8.05-8.07 (d, J=8 Hz, 1H), 7.81-7.85 (m, 1H), 7.50-7.54 (d, J=8 Hz, 1H).

b. Synthesis of N-(3-chloro-4-fluorophenyl)-7-(3-methoxypropoxy)-6-nitro-4-quinazolinamine

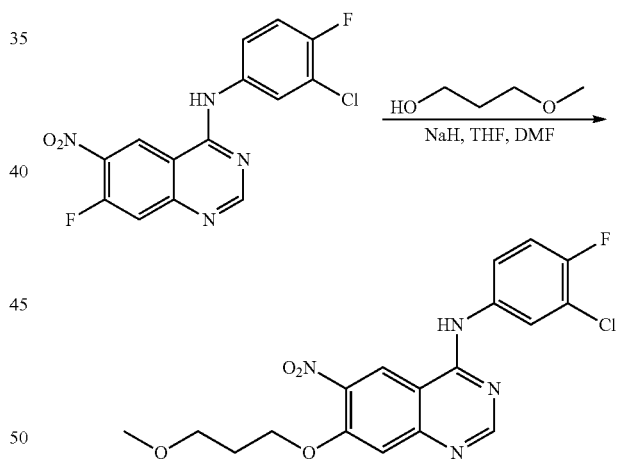

Under nitrogen gas atmosphere, 60 wt. % NaH (500 mg, 12.5 mmol, the wt. % refers to the percentage of the mass of sodium hydride accounted for of the total mass of the sodium hydride reagent) was added into a three-neck flask containing anhydrous tetrahydrofuran (5 mL), cooled to 0° C., into which a solution of propylene glycol methyl ether in anhydrous tetrahydrofuran (5 mL) was dripped, a lot of bubbles appeared in the system at the moment. The reaction mixture was stirred for 2 h at room temperature and cooled to −15° C., then added into a suspension of compound N-(3-chloro-4-fluorophenyl)-7-fluoro-6-nitro-4-quinazolinamine (0.5 g, 1.48 mmol) in THF (5 mL) and DMF (1 mL), during the dripping the system turned to blood red. The reaction mixture was reacted at −15° C. for 1.5 h, then stirred at room temperature for 1 h. The reaction solution was diluted with a lot of ice-water, extracted with ethyl acetate (5 mL×3), the organic phases were combined, dried, and filtrated, the filtrate was concentrated by evaporation to deliver a yellow solid N-(3-chloro-4-fluorophenyl)-7-(3-methoxypropoxy)-6-nitro-4-quinazolinamine (300 mg, 50% yield), which was used for the next step directly without further purification. ESI-MS (m/z): 407.1 [M+H]$^+$.

c. Synthesis of N-(3-chloro-4-fluorophenyl)-7-(3-methoxypropoxy)-6-amino-4-quinazolinamine

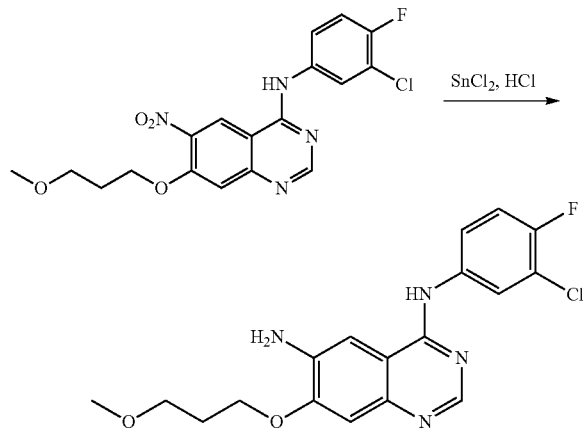

Anhydrous SnCl$_2$ (350 mg, 1.845 mmol) was fully dissolved in conc. hydrochloric acid (5 mL), and was added slowly into a flask containing compound N-(3-chloro-4-fluorophenyl)-7-(3-methoxypropoxy)-6-nitro-4-quinazolinamine (250 mg, 0.615 mmol), heated to 50° C. and reacted for 2 h, the solid in the reaction solution was filtrated under vacuum to deliver the product N-(3-chloro-4-fluorophenyl)-7-(3-methoxypropoxy)-6-amino-4-quinazolinamine hydrochloride (280 mg, 100% yield). ESI-MS (m/z): 377.1 [M+H]$^+$.

d. Synthesis of (E)-4-(dimethylamino)but-2-enoyl chloride hydrochloride

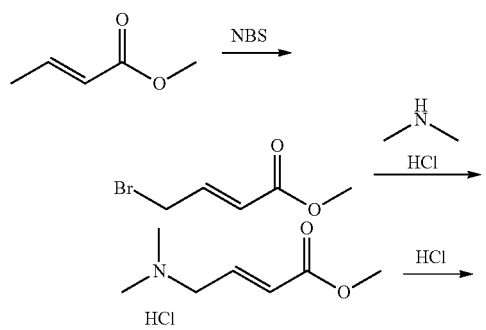

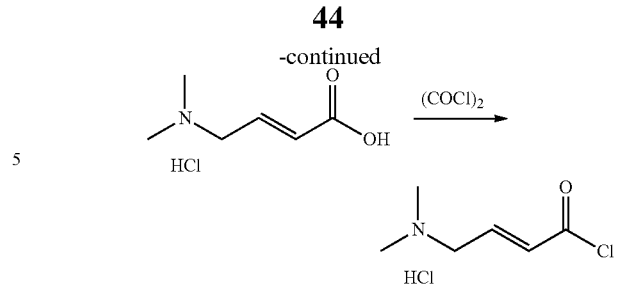

Compound methyl crotonate (20 g, 200 mmol) was added into a 500 mL one-neck flask, and dissolved with CCl$_4$ (200 mL), AIBN (66 mg, 0.4 mmol) and NBS (39.1 g, 220 mmol) were added while stirring, the reaction mixture was heated to reflux and reacted for 6 h, cooled, filtrated to remove the solid, the filtrate was washed with water (20 ml×3), dried over anhydrous Na$_2$SO$_4$, filtrated and evaporated up to dry to deliver a yellow oil methyl-4-bromocrotonate (34 g), the compound was used for the next step directly without further purification.

Compound methyl-4-bromocrotonate (34 g, 190 mmol) was added into a 500 mL one-neck flask, and dissolved with THF (200 mL), dimethylamine hydrochloride (18.5 g, 230 mmol) and Et$_3$N (74.2 ml, 530 mmol) were added while stirring, the reaction mixture was stirred to react overnight at room temperature, after methyl-4-bromocrotonate was fully reacted, the solvent was evaporated to remove, the remaining yellow oil was added into isopropanol (200 mL), a solution of 4M HCl/dioxane was dripped in to adjust pH≤2, a white solid was precipitated, filtrated and the filtrate cake was washed with THF, dried to deliver a white solid methyl 4-(dimethylamino)but-2-enoate hydrochloride (10 g, 30% yield). $^1$H-NMR (d-DMSO, 400 MHz, δ ppm): 6.89-6.92 (m, 1H), 6.30 (d, J=16 Hz, 1H), 3.91 (d, J=8 Hz, 2H), 3.70 (s, 3H), 2.72 (s, 6H).

Compound methyl 4-(dimethylamino)but-2-enoate hydrochloride (10 g, 56 mmol) was added in a 250 mL one-neck flask, 6N hydrochloric acid aqueous solution (100 mL) was added, the reaction mixture was reacted at reflux for 6 h, then evaporated to deliver a white solid 4-(dimethylamino)but-2-enoic acid hydrochloride (9.0 g, 98% yield). $^1$H-NMR (d-DMSO, 400 MHz, δ ppm): 6.75-6.81 (m, 1H), 6.18 (d, J=16 Hz, 1H), 3.89 (d, J=8 Hz, 2H), 2.74 (s, 6H).

4-dimethylaminocrotonic acid hydrochloride (0.3 g, 1.8 mmol), anhydrous THF (5 mL) and 3 drops of DMF were added into a three-neck flask, into which oxalyl chloride (0.25 g, 2 mmol) was dripped under nitrogen gas atmosphere, the reaction mixture was reacted for 30 min at room temperature to deliver compound (E)-4-(dimethylamino)but-2-enoyl chloride hydrochloride, which was used for the next step directly.

e. Synthesis of (E)-N-(4-(3-chloro-4-fluorophenylamino)-7-(3-methoxypropoxy)quinazolin-6-yl)-4-(dimethylamino)but-2-enamide (Compound 1)

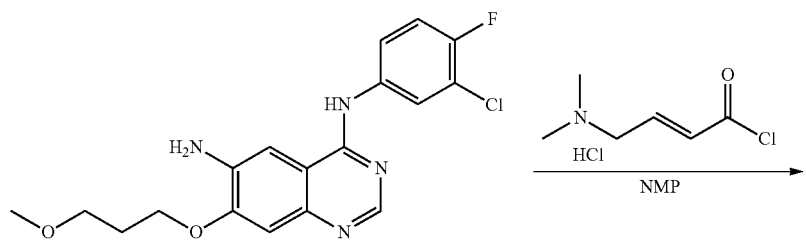

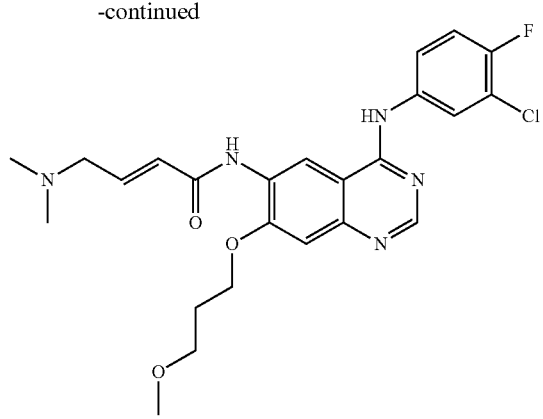

Compound 1

(E)-4-(dimethylamino)but-2-enoyl chloride hydrochloride (0.3 g, 1.8 mmol), anhydrous THF (5 mL) were added into a three-neck flask, a solution of N-(3-chloro-4-fluorophenyl)-7-(3-methoxypropoxy)-6-amino-4-quinazolinamine hydrochloride (0.2 g, 0.5 mmol) in NMP (3 mL) was dripped and the reaction mixture was reacted for 1 h. Water (3 mL) was added, 10% NaOH solution was added to adjust PH≥11, the reaction mixture was extracted with EtOAc (5 ml×3), dried, filtrated, evaporated up to dry, purified by preparative TLC to deliver the target compound (E)-N-(4-(3-chloro-4-fluorophenylamino)-7-(3-methoxypropoxy)quinazolin-6-yl)-4-(dimethylamino)but-2-enamide (102 mg, 39% yield) as a yellow solid. $^1$H-NMR (d-DMSO, 400 MHz, δ ppm): 9.80 (s, 1H), 9.54 (s, 1H), 8.89 (s, 1H), 8.53 (s, 1H), 8.12-8.15 (m, 1H), 7.79-7.82 (m, 1H), 7.40-7.44 (m, 1H), 7.27 (s, 1H), 6.78-6.84 (m, 1H), 6.57-6.61 ((d, J=16 Hz, 1H), 4.25-4.27 (m, 2H), 3.52-3.54 (m, 2H), 3.27-3.29 (m, 2H), 3.26 (s, 3H), 2.33 (s, 6H), 2.06-2.09 (m, 2H).

Embodiment 2: Synthesis of (R,E)-N-(4-(3-chloro-4-fluorophenylamino)-7-(2-methoxy-1-methylethoxy)quinazolin-6-yl)-4-(dimethylamino)but-2-enamide (Compound 2)

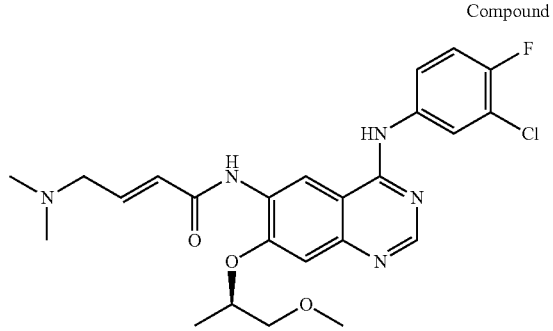

Compound 2 a. Synthesis of (R)—N-(3-chloro-4-fluorophenyl)-7-(2-methoxy-1-methylethoxy)-6-amino-4-quinazolinamine hydrochloride

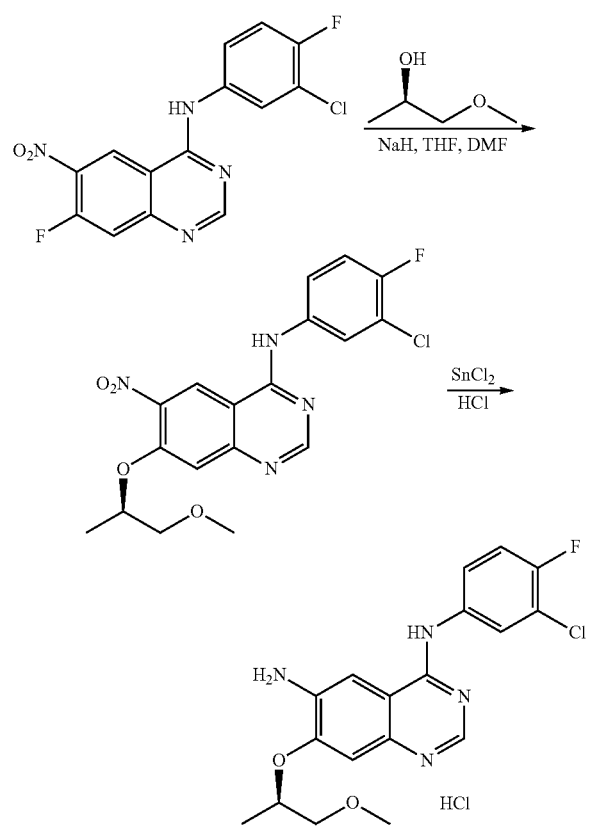

According to a method similar to the preparation of compound 1, taking (R)-1-methoxy-2-propanol as the starting material, compound (R)—N-(3-chloro-4-fluorophenyl)-7-(2-methoxy-1-methylethoxy)-6-nitro-4-quinazolinamine (83% yield) can be synthesized as a yellow solid. $^1$H-NMR (d-DMSO, 400 MHz, δ ppm): 10.12 (s, 1H), 9.17 (s, 1H), 8.67 (s, 1H), 8.16-8.18 (m, 1H), 7.78-7.82 (m, 1H), 7.59 (s, 1H), 7.46 (t, J=8.0 Hz, 1H), 5.05-5.10 (m, 1H), 3.56-3.57 (m, 2H), 3.30 (s, 3H), 1.32 (d, J=6.0 Hz, 3H).

According to a method similar to the preparation of compound 1, taking (R)—N-(3-chloro-4-fluorophenyl)-7-(2-methoxy-1-methylethoxy)-6-nitro-4-quinazolinamine as the starting material, compound (R)—N-(3-chloro-4-fluorophenyl)-7-(2-methoxy-1-methylethoxy)-6-amino-4-quinazolinamine hydrochloride (40% yield) can be synthesized. ESI-MS (m/z): 377.1 [M+H]$^+$.

b. Synthesis of (R,E)-N-(4-(3-chloro-4-fluorophenylamino)-7-(2-methoxy-1-methylethoxy)quinazolin-6-yl)-4-(dimethylamino)but-2-enamide (Compound 2)

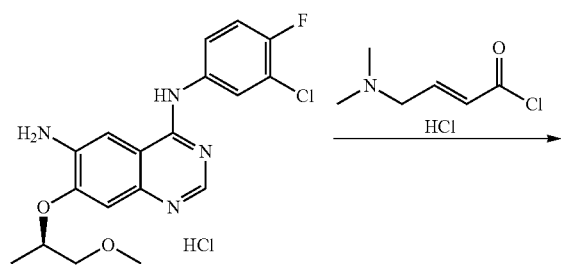

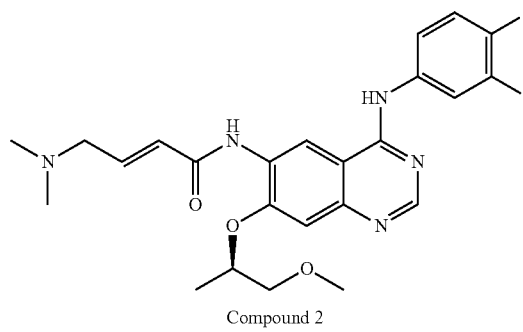

Compound 2

According to a method similar to the preparation of compound 1, taking (R)—N-(3-chloro-4-fluorophenyl)-7-(2-methoxy-1-methylethoxy)-6-amino-4-quinazolinamine hydrochloride as the starting material, compound 2 can be synthesized (32% yield) as a yellow solid. $^1$H-NMR (d-DMSO, 400 MHz, δ ppm): 9.83 (s, 1H), 9.58 (s, 1H), 8.93 (s, 1H), 8.52 (s, 1H), 8.11-8.13 (m, 1H), 7.78-7.81 (m, 1H), 7.45 (t, J=8.0 Hz, 1H), 7.42 (s, 1H), 6.82-6.87 (m, 1H), 6.70 (d, J=16 Hz, 1H), 4.91-4.93 (m, 1H), 3.67-3.69 (m, 2H), 3.55-3.57 (m, 2H), 3.48 (s, 3H), 2.47 (m, 6H), 1.33 (d, J=6.0 Hz, 3H).

Embodiment 3: Synthesis of (S,E)-N-(4-(3-chloro-4-fluorophenylamino)-7-(2-methoxy-1-methylethoxy)quinazolin-6-yl)-4-(dimethylamino)but-2-enamide (Compound 3)

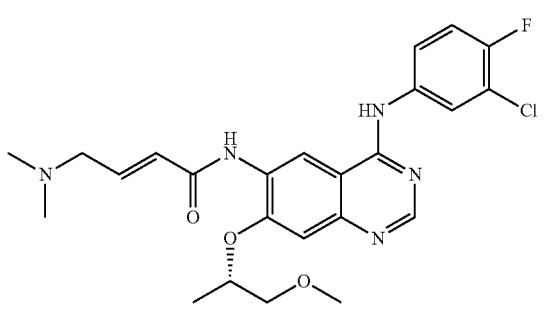

Compound 3 a. Synthesis of (S)—N-(3-chloro-4-fluorophenyl)-7-(2-methoxy-1-methylethoxy)-6-amino-4-quinazolinamine hydrochloride

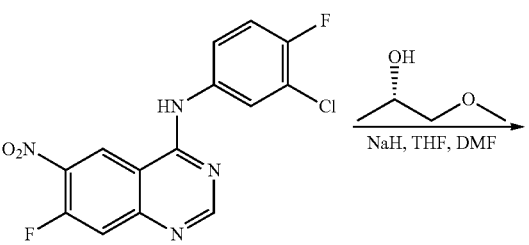

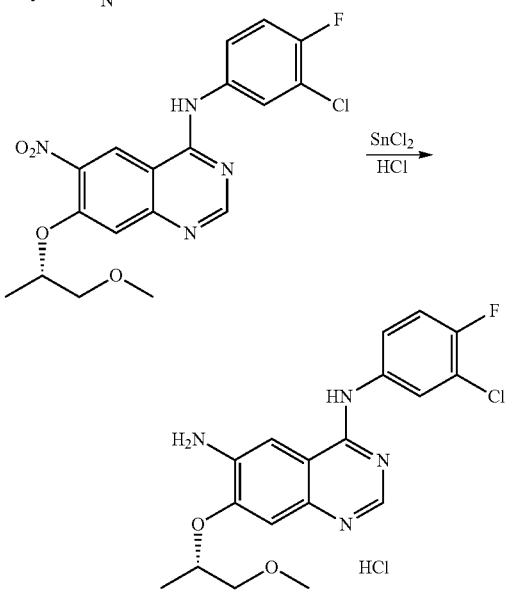

According to a method similar to the preparation of compound 1, taking (S)-1-methoxy-2-propanol as the starting material, compound (S)—N-(3-chloro-4-fluorophenyl)-7-(2-methoxy-1-methylethoxy)-6-nitro-4-quinazolinamine (81% yield) can be synthesized as a yellow solid. $^1$H-NMR (d-DMSO, 400 MHz, δ ppm): 10.12 (s, 1H), 9.17 (s, 1H), 8.67 (s, 1H), 8.16-8.18 (m, 1H), 7.78-7.82 (m, 1H), 7.59 (s, 1H), 7.46 (t, J=8.0 Hz, 1H), 5.05-5.10 (m, 1H), 3.56-3.57 (m, 2H), 3.30 (s, 3H), 1.32 (d, J=6.0 Hz, 3H).

According to a method similar to the preparation of compound 1, taking (S)—N-(3-chloro-4-fluorophenyl)-7-(2-methoxy-1-methylethoxy)-6-nitro-4-quinazolinamine as the starting material, compound (S)—N-(3-chloro-4-fluorophenyl)-7-(2-methoxy-1-methylethoxy)-6-amino-4-quinazolinamine hydrochloride (42% yield) can be synthesized. ESI-MS (m/z): 377.1 [M+H]+.

b. Synthesis of (S,E)-N-(4-(3-chloro-4-fluorophenylamino)-7-(2-methoxy-1-methylethoxy)quinazolin-6-yl)-4-(dimethylamino)but-2-enamide (Compound 3)

According to a method similar to the preparation of compound 1, taking (S)—N-(3-chloro-4-fluorophenyl)-7-(2-methoxy-1-methylethoxy)-6-amino-4-quinazolinamine hydrochloride as the starting material, compound 3 can be synthesized (50% yield) as a yellow solid. $^1$H-NMR (d-DMSO, 400 MHz, δ ppm): 9.81 (s, 1H), 9.51 (s, 1H), 8.94 (s, 1H), 8.52 (s, 1H), 8.12-8.14 (m, 1H), 7.79-7.82 (m, 1H), 7.43 (t, J=8.0 Hz, 1H), 7.37 (s, 1H), 6.81-6.84 (m, 1H), 6.65 (d, J=16 Hz, 1H), 4.91-4.95 (m, 1H), 3.65-3.67 (m, 2H), 3.56-3.57 (m, 2H), 3.48 (s, 3H), 2.49 (m, 6H), 1.33 (d, J=6.0 Hz, 3H).

Embodiment 4: Synthesis of (E)-N-(4-(3-chloro-4-fluorophenylamino)-7-(2-ethoxyethoxy)quinazolin-6-yl)-4-(dimethylamino)but-2-enamide (Compound 4)

Compound 4

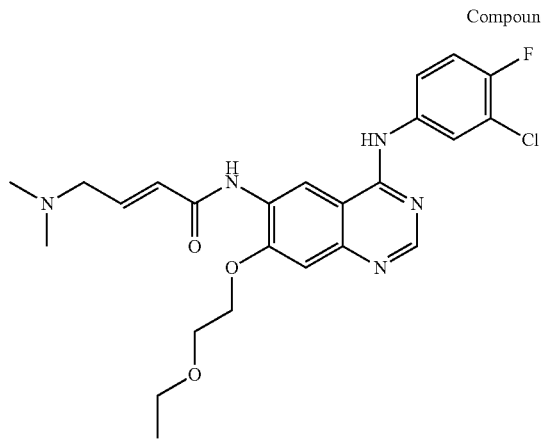

a. Synthesis of N-(3-chloro-4-fluorophenyl)-7-(2-ethoxyethoxy)-6-nitro-4-quinazolinamine

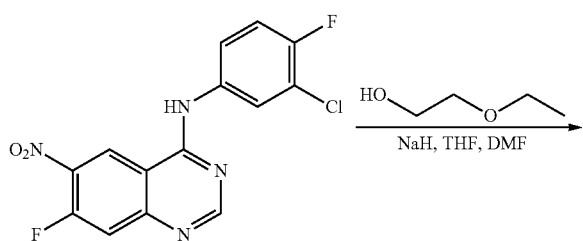

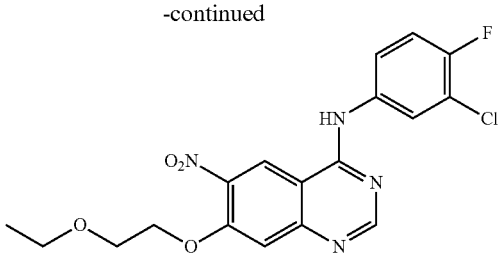

According to a method similar to the preparation of compound 1, taking 2-ethoxyethanol as the starting material, N-(3-chloro-4-fluorophenyl)-7-(2-ethoxyethoxy)-6-nitro-4-quinazolinamine can be synthesized (66% yield) as a yellow solid. $^1$H-NMR (d-DMSO, 400 MHz, δ ppm): 10.17 (s, 1H), 9.21 (s, 1H), 8.68 (s, 1H), 8.15-8.18 (m, 1H), 7.79-7.82 (m, 1H), 7.52 (s, 1H), 7.47 (t, J=8.0 Hz, 1H), 4.43 (t, J=4.4 Hz, 2H), 3.78 (t, J=4.4 Hz, 2H), 3.53-3.55 (m, 2H), 1.12 (t, J=7.2 Hz, 3H).

b. Synthesis of N-(3-chloro-4-fluorophenyl)-7-(2-ethoxyethoxy)-6-amino-4-quinazolinamine

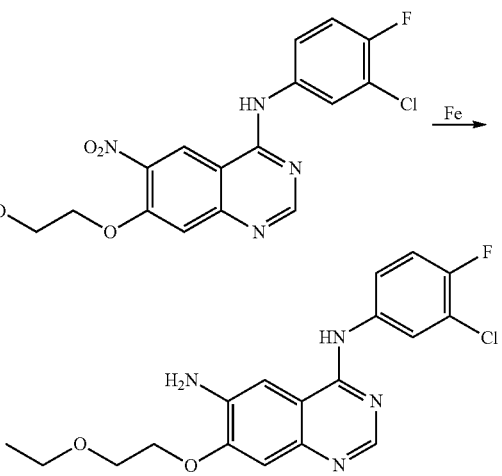

Compound N-(3-chloro-4-fluorophenyl)-7-(2-ethoxyethoxy)-6-nitro-4-quinazolinamine (400 mg, 0.984 mmol) was added into a 100 mL one-neck flask, acetic acid (6 mL) and iron powder (0.26 g, 4.63 mmol) were added, reacted for 1.5 h at room temperature, filtrated to remove most of the iron powder, the pH value of the filtrate was adjusted to 11 with 10% NaOH aqueous solution, a large amount of solid was precipitated, filtrated and washed with water, the solid was dried to deliver a yellow solid N-(3-chloro-4-fluorophenyl)-7-(2-ethoxyethoxy)-6-amino-4-quinazolinamine (150 mg, 41% yield). $^1$H-NMR (d-DMSO, 400 MHz, δ ppm): 9.41 (s, 1H), 8.38 (s, 1H), 8.19-8.21 (m, 1H), 7.80-7.82 (m, 1H), 7.40-7.42 (m, 1H), 7.12 (s, 1H), 5.32 (s, 2H), 4.28 (t, J=4.4 Hz, 2H), 3.83 (t, J=4.4 Hz, 2H), 3.53-3.57 (m, 2H), 1.15 (t, J=7.2 Hz, 3H).

c. Synthesis of (E)-N-(4-(3-chloro-4-fluorophenylamino)-7-(2-ethoxyethoxy)quinazolin-6-yl)-4-(dimethylamino)but-2-enamide (Compound 4)

According to a method similar to the preparation of compound 1, taking N-(3-chloro-4-fluorophenyl)-7-(2- ethoxyethoxy)-6-amino-4-quinazolinamine as the starting material, compound 4 can be synthesized (73% yield) as a yellow solid. $^1$H-NMR (d-DMSO, 400 MHz, δ ppm): 9.94 (s, 1H), 9.77 (s, 1H), 9.01 (s, 1H), 8.65 (s, 1H), 8.23-8.25 (m, 1H), 7.90-7.93 (m, 1H), 7.52-7.54 (t, J=8.0 Hz, 1H), 7.44 (s, 1H), 6.90-6.96 (m, 1H), 6.73 (d, J=16 Hz, 1H), 4.46 (t, J=4.4 Hz, 2H), 3.94 (t, J=4.4 Hz, 2H), 3.65-3.67 (m, 2H), 3.29 (d, J=5.6 Hz, 2H), 2.62 (s, 6H), 1.24 (t, J=7.2 Hz, 3H).

Embodiment 5: Synthesis of (E)-N-(4-(3-chloro-4-fluorophenylamino)-7-(2-propoxyethoxy)quinazolin-6-yl)-4-(dimethylamino)but-2-enamide (Compound 5)

Compound 5

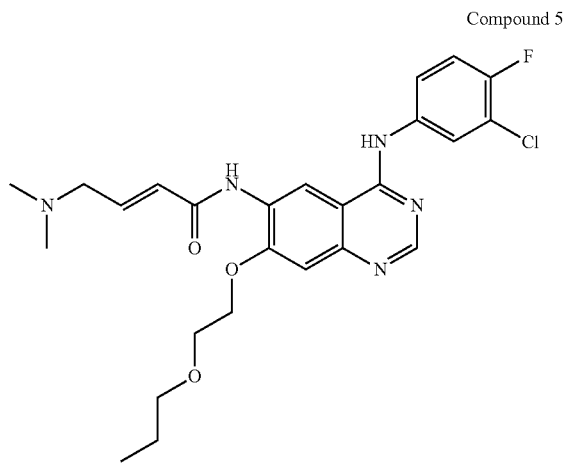 [SMILES: CCCOCCOc1cc2ncnc(Nc3ccc(F)c(Cl)c3)c2cc1NC(=O)/C=C/CN(C)C]

a. Synthesis of N-(3-chloro-4-fluorophenyl)-7-(2-propoxyethoxy)-6-nitro-4-quinazolinamine

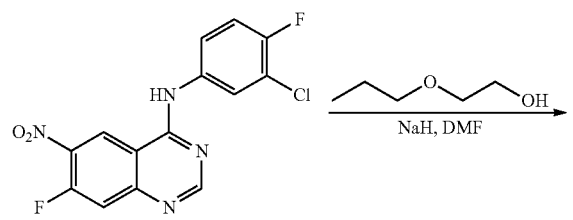

According to a method similar to the preparation of compound 1, taking 2-propoxyethan-1-ol as the starting material, N-(3-chloro-4-fluorophenyl)-7-(2-propoxyethoxy)-6-nitro-4-quinazolinamine can be synthesized (84% yield) as a yellow solid. $^1$H-NMR (d-DMSO, 400 MHz, δ ppm): 10.17 (s, 1H), 9.21 (s, 1H), 8.68 (s, 1H), 8.17 (d, J=8.0 Hz, 1H), 8.12-8.15 (m, 1H), 7.82 (s, 1H), 7.79 (t, J=8.0 Hz, 1H), 4.44 (t, J=4.4 Hz, 2H), 3.77 (t, J=4.4 Hz, 2H), 3.42-3.46 (m, 2H), 1.49-1.54 (m, 2H), 0.86 (t, J=7.2 Hz, 3H).

b. Synthesis of N-(3-chloro-4-fluorophenyl)-7-(2-propoxyethoxy)-6-amino-4-quinazolinamine

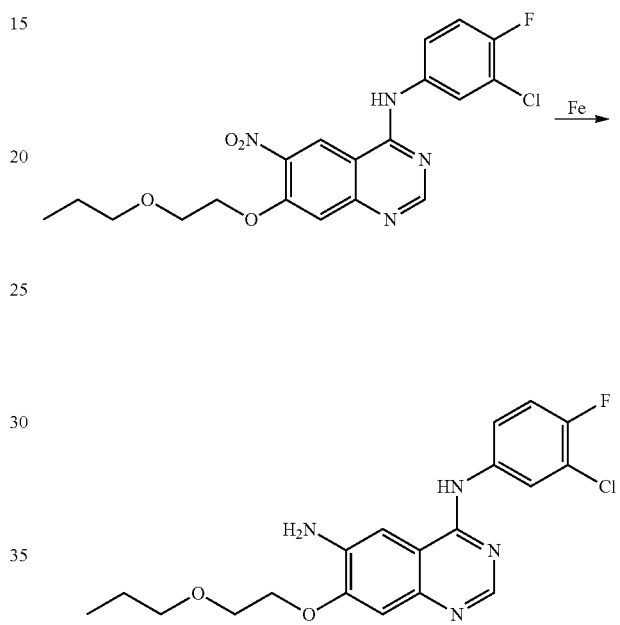

According to a method similar to the preparation of compound 4, taking N-(3-chloro-4-fluorophenyl)-7-(2-propoxyethoxy)-6-nitro-4-quinazolinamine as the starting material, N-(3-chloro-4-fluorophenyl)-7-(2-propoxyethoxy)-6-amino-4-quinazolinamine can be synthesized (83% yield) as a yellow solid. $^1$H-NMR (d-DMSO, 400 MHz, δ ppm): 9.41 (s, 1H), 8.37 (s, 1H), 8.17-8.19 (m, 1H), 7.80-7.82 (m, 1H), 7.38-7.41 (m, 2H), 7.13 (s, 1H), 5.32 (s, 2H), 4.28 (t, J=4.4 Hz, 2H), 3.83 (t, J=4.4 Hz, 2H), 3.46-3.48 (m, 2H), 1.54-1.56 (m, 2H), 0.86 (t, J=7.2 Hz, 3H).

c. Synthesis of (E)-N-(4-(3-chloro-4-fluorophenylamino)-7-(2-propoxyethoxy)quinazolin-6-yl)-4-(dimethylamino)but-2-enamide (Compound 5)

According to a method similar to the preparation of compound 1, taking N-(3-chloro-4-fluorophenyl)-7-(2-propoxyethoxy)-6-amino-4-quinazolinamine as the starting material, compound 5 can be synthesized (31% yield) as a yellow solid. $^1$H-NMR (d-DMSO, 400 MHz, δ ppm): 9.82 (s, 1H), 9.58 (s, 1H), 8.90 (s, 1H), 8.53 (s, 1H), 8.12-8.15 (m, 1H), 7.79-7.80 (m, 1H), 7.42 (t, J=8.0 Hz, 1H), 7.33 (s, 1H), 6.78-6.83 (m, 1H), 6.57 (d, J=16 Hz, 1H), 4.36 (t, J=4.4 Hz, 2H), 3.83 (t, J=4.4 Hz, 2H), 3.42-3.46 (m, 2H), 3.20 (d, J=5.6 Hz, 2H), 2.27 (s, 6H), 1.52-1.53 (m, 2H), 0.85 (t, J=7.2 Hz, 3H).

Embodiment 6: Synthesis of (E)-N-(4-(3-chloro-4-fluorophenylamino)-7-(2-isopropoxyethoxy)quinazolin-6-yl)-4-(dimethylamino)but-2-enamide (Compound 6)

Compound 6

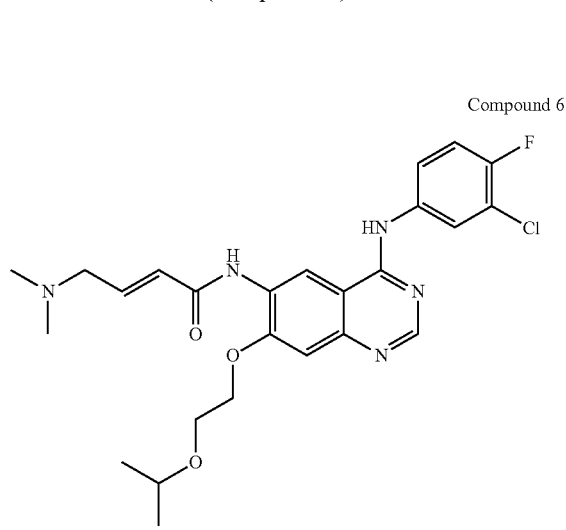

a. Synthesis of N-(3-chloro-4-fluorophenyl)-7-(2-isopropoxyethoxy)-6-nitro-4-quinazolinamine

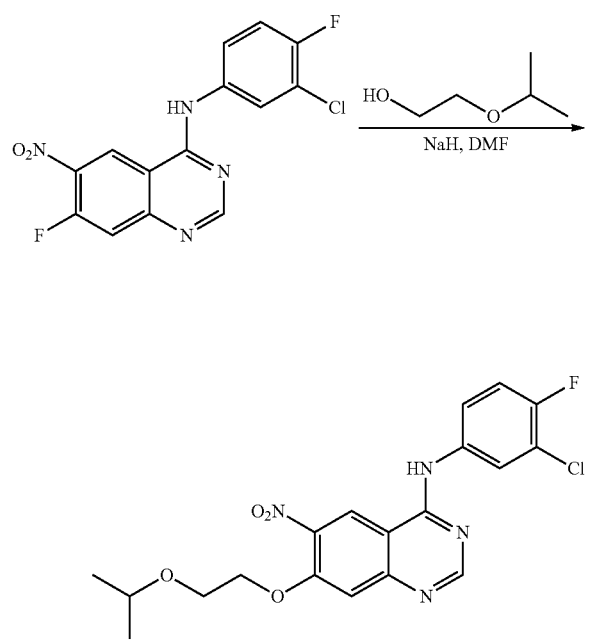

According to a method similar to the preparation of compound 1, taking 2-isopropoxyethan-1-ol as the starting material, N-(3-chloro-4-fluorophenyl)-7-(2-isopropoxyethoxy)-6-nitro-4-quinazolinamine can be synthesized (81% yield) as a yellow solid. $^1$H-NMR (d-DMSO, 400 MHz, δ ppm): 10.16 (s, 1H), 9.22 (s, 1H), 8.67 (s, 1H), 8.15-8.18 (m, 1H), 7.78-7.82 (m, 1H), 7.51 (s, 1H), 7.48 (t, J=8.0 Hz, 1H), 4.40 (t, J=4.4 Hz, 2H), 3.76 (t, J=4.4 Hz, 2H), 3.63-3.67 (m, 1H), 1.10 (d, J=6.0 Hz, 6H).

b. Synthesis of N-(3-chloro-4-fluorophenyl)-7-(2-isopropoxyethoxy)-6-amino-4-quinazolinamine

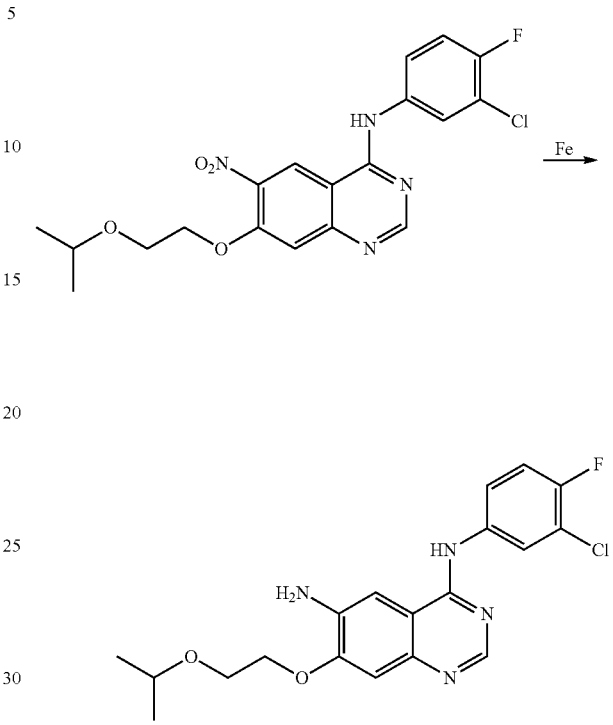

According to a method similar to the preparation of compound 4, taking N-(3-chloro-4-fluorophenyl)-7-(2-isopropoxyethoxy)-6-nitro-4-quinazolinamine as the starting material, N-(3-chloro-4-fluorophenyl)-7-(2-isopropoxyethoxy)-6-amino-4-quinazolinamine can be synthesized (78% yield). $^1$H-NMR (d-DMSO, 400 MHz, δ ppm): 9.43 (s, 1H), 8.38 (s, 1H), 8.17-8.20 (m, 1H), 7.78-7.82 (m, 1H), 7.38-7.41 (m, 2H), 7.12 (s, 1H), 5.31 (s, 2H), 4.26 (t, J=4.4 Hz, 2H), 3.81 (t, J=4.4 Hz, 2H), 3.66-3.69 (m, 1H), 1.13 (d, J=6.0 Hz, 6H).

c. Synthesis of (E)-N-(4-(3-chloro-4-fluorophenylamino)-7-(2-isopropoxyethoxy)quinazolin-6-yl)-4-(dimethylamino)but-2-enamide (Compound 6)

According to a method similar to the preparation of compound 1, taking N-(3-chloro-4-fluorophenyl)-7-(2-isopropoxyethoxy)-6-amino-4-quinazolinamine as the starting material, compound 6 can be synthesized (62% yield) as a yellow solid. $^1$H-NMR (d-DMSO, 400 MHz, δ ppm): 9.81 (s, 1H), 9.57 (s, 1H), 8.89 (s, 1H), 8.53 (s, 1H), 8.12-8.14 (m, 1H), 7.78-7.81 (m, 1H), 7.43 (t, J=8.0 Hz, 1H), 7.32 (s, 1H), 6.78-6.82 (m, 1H), 6.56 (d, J=16 Hz, 1H), 4.31 (t, J=4.4 Hz, 2H), 3.83 (t, J=4.4 Hz, 2H), 3.66-3.69 (m, 1H), 3.26-3.36 (m, 2H), 2.29 (s, 6H), 1.11 (d, J=6.0 Hz, 6H).

Embodiment 7: Synthesis of (E)-N-(4-(3-chloro-4-fluorophenylamino)-7-(2-(2,2,2-trifluoroethoxy)ethoxy)quinazolin-6-yl)-4-(dimethylamino)but-2-enamide (Compound 7)

Compound 7

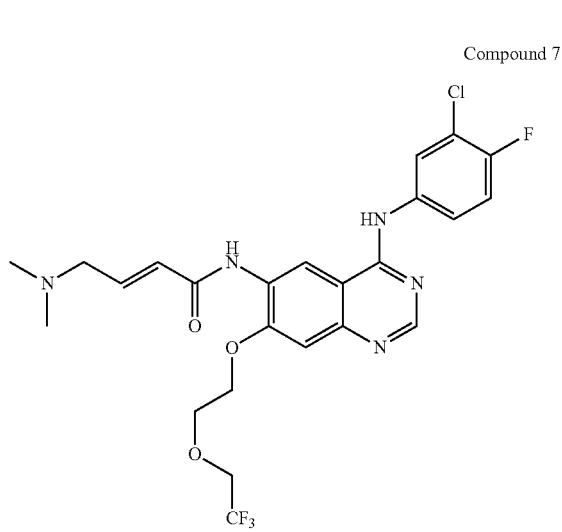 [SMILES: CN(C)C/C=C/C(=O)Nc1cc2c(Nc3ccc(F)c(Cl)c3)ncnc2cc1OCCOCC(F)(F)F]

a. Synthesis of N-(3-chloro-4-fluorophenyl)-7-(2-(2,2,2-trifluoroethoxy)ethoxy)-6-nitro-4-quinazolinamine

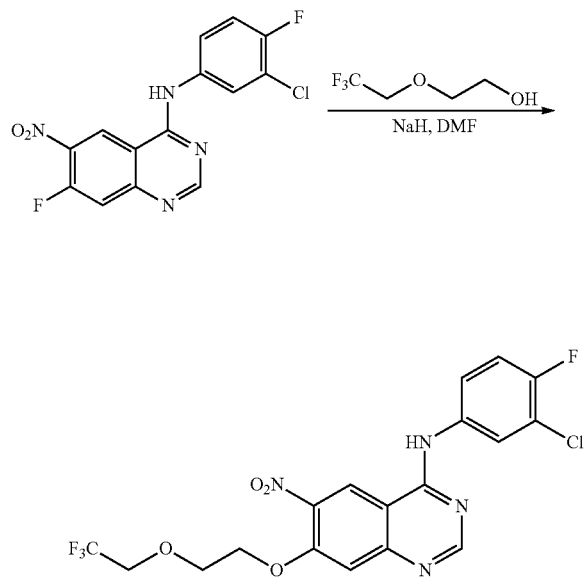

According to a method similar to the preparation of compound 1, taking 2-(2,2,2-trifluoroethoxy)ethanol as the starting material, N-(3-chloro-4-fluorophenyl)-7-(2-(2,2,2-trifluoroethoxy)ethoxy)-6-nitro-4-quinazolinamine can be synthesized (60% yield). $^1$H-NMR (d-DMSO, 400 MHz, δ ppm): 10.18 (s, 1H), 9.22 (s, 1H), 8.66 (s, 1H), 8.13-8.15 (m, 1H), 7.77-7.79 (m, 1H), 7.43-7.48 (m, 2H), 4.46 (t, J=4.4 Hz, 2H), 4.18-4.22 (m, 2H), 4.01 (t, J=4.4 Hz, 2H).

b. Synthesis of N-(3-chloro-4-fluorophenyl)-7-(2-(2,2,2-trifluoroethoxy)ethoxy)-6-amino-4-quinazolinamine

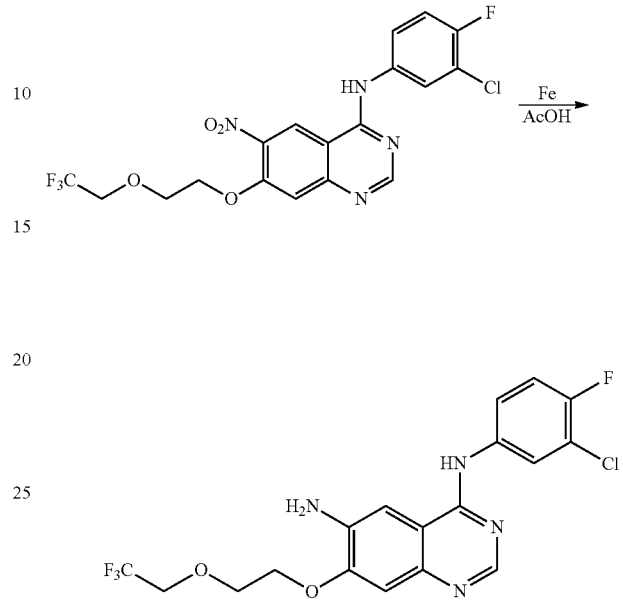

According to a method similar to the preparation of compound 4, taking N-(3-chloro-4-fluorophenyl)-7-(2-(2,2,2-trifluoroethoxy)ethoxy)-6-nitro-4-quinazolinamine as the starting material, N-(3-chloro-4-fluorophenyl)-7-(2-(2,2,2-trifluoroethoxy)ethoxy)-6-amino-4-quinazolinamine can be synthesized (82% yield). $^1$H-NMR (d-DMSO, 400 MHz, δ ppm): 9.53 (s, 1H), 8.40 (s, 1H), 8.17-8.19 (m, 1H), 7.78-7.80 (m, 1H), 7.38-7.42 (m, 2H), 7.12 (s, 1H), 5.42 (s, 2H), 4.33 (t, J=4.4 Hz, 2H), 4.22-4.26 (m, 2H), 4.06 (t, J=4.4 Hz, 2H).

c. Synthesis of (E)-N-(4-(3-chloro-4-fluorophenylamino)-7-(2-(2,2,2-trifluoroethoxy)ethoxy)quinazolin-6-yl)-4-(dimethylamino)but-2-enamide (Compound 7)

According to a method similar to the preparation of compound 1, taking N-(3-chloro-4-fluorophenyl)-7-(2-(2,2,2-trifluoroethoxy)ethoxy)-6-amino-4-quinazolinamine as the starting material, compound 7 can be synthesized (77% yield) as a yellow solid. $^1$H-NMR (d-DMSO, 400 MHz, δ ppm): 9.81 (s, 1H), 9.57 (s, 1H), 9.89 (s, 1H), 9.57 (s, 1H), 8.89 (s, 1H), 8.53 (s, 1H), 8.11-8.12 (m, 1H), 7.77-7.81 (m, 1H), 7.42 (t, J=8.0 Hz, 1H), 7.31 (s, 1H), 6.83-6.87 (m, 1H), 6.64 (d, J=16 Hz, 1H), 4.34 (t, J=4.4 Hz, 2H), 4.18-4.21 (m, 2H), 4.16 (t, J=4.4 Hz, 2H), 3.28 (d, J=5.6 Hz, 2H), 2.32 (s, 6H).

Embodiment 8: Synthesis of (E)-N-(4-(3-chloro-4-fluorophenylamino)-7-(2-(methylsulfonamido)ethoxy)quinazolin-6-yl)-4-(dimethylamino)but-2-enamide (Compound 8)

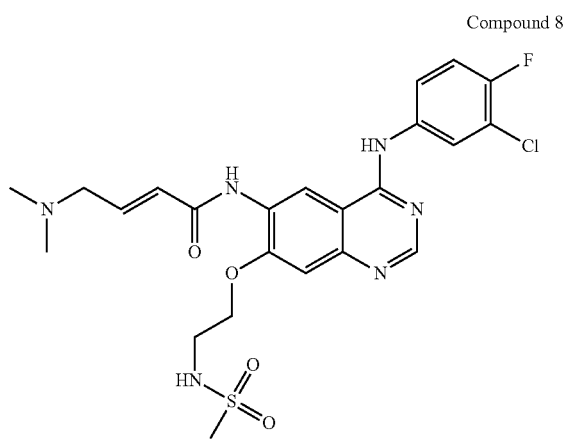 [SMILES: CN(C)C/C=C/C(=O)Nc1cc2c(Nc3ccc(F)c(Cl)c3)ncnc2cc1OCCNS(C)(=O)=O]

Compound 8 a. Synthesis of 7-(2-aminoethoxy)-N-(3-chloro-4-fluorophenyl)-6-nitro-4-quinazolinamine

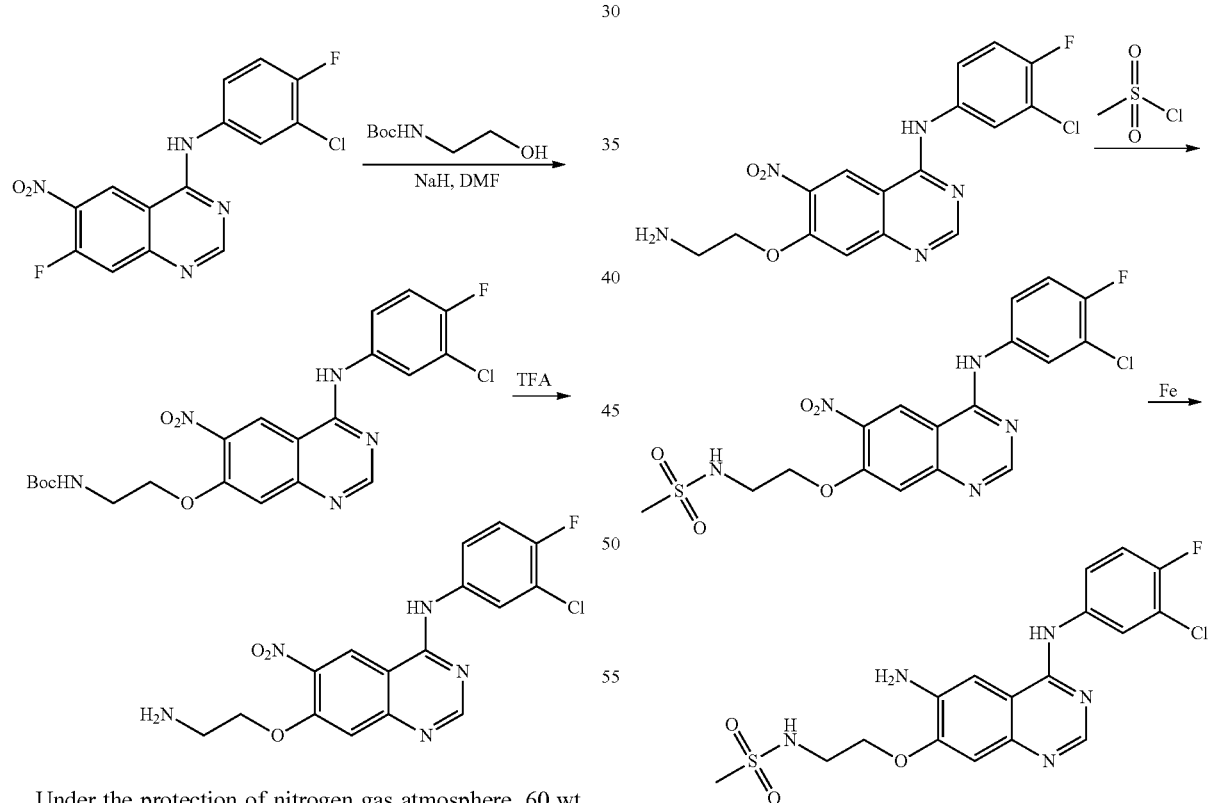

Under the protection of nitrogen gas atmosphere, 60 wt. % NaH (0.24 g, 5.95 mmol) was added into a three-neck flask containing DMF (5 mL), cooled to 0° C., into which a solution of N-Boc-ethanolamine (0.48 g, 2.98 mmol) in DMF (5 mL) was dripped, a lot of bubbles appeared in the system at the moment. The reaction mixture was stirred for 0.5 h at room temperature and cooled to −15° C., then added into a suspension of compound N-(3-chloro-4-fluorophenyl)-7-fluoro-6-nitro-4-quinazolinamine (0.5 g, 1.49 mmol) in DMF (1 mL), during the dripping the system turned to blood red, the reaction mixture was reacted at −15° C. for 1.5 h, then stirred at room temperature for 1 h. The reaction mixture was quenched with a lot of ice-water, a large amount of yellow solid was precipitated, filtrated and washed with water, the solid was collected and dried to deliver the product 2-(4-(3-chloro-4-fluorophenylamino)-6-nitro-quinazolin-7-oxy)ethyl tert-butyl carbamate (0.28 g, 40% yield). ESI-MS (m/z): 478.1 [M+H]$^+$.

2-(4-(3-Chloro-4-fluorophenylamino)-6-nitro-quinazolin-7-oxy)ethyl tert-butyl carbamate (0.19 g, 0.6 mmol) was dissolved in DCM (9 mL), TFA (3 mL) was added under an ice bath. The reaction mixture was reacted for 3 h at room temperature, evaporated to dry, saturated NaHCO$_3$ aqueous solution was added to adjust the pH value to 7-8, extracted with DCM, dried over anhydrous Na$_2$SO$_4$ and evaporated to dry, purified by preparative TLC to deliver 7-(2-aminoethoxy)-N-(3-chloro-4-fluorophenyl)-6-nitro-4-quinazolinamine (0.19 g, 85% yield). $^1$H-NMR (d-DMSO, 400 MHz, δ ppm): 9.31 (s, 1H), 8.74 (s, 1H), 8.22-8.24 (m, 1H), 7.85-7.89 (m, 1H), 7.57 (s, 1H), 7.54 (t, J=9.2 Hz, 1H), 4.36 (t, J=5.6 Hz, 2H), 3.06 (t, J=5.6 Hz, 2H).

b. Synthesis of N-(2-(6-amino-4-(3-chloro-4-fluorophenylamino)quinazolin-7-oxy)ethyl)methanesulfonamide 7-(2-Aminoethoxy)-N-(3-chloro-4-fluorophenyl)-6-nitro-4-quinazolinamine (0.19 g, 0.51 mmol) was dissolved into anhydrous THF (5 mL), into which DIPEA (0.2 g, 1.53 mmol) was added, methanesulfonyl chloride (0.12 g, 1.02 mmol) was added under an ice bath. The reaction mixture was reacted overnight at room temperature, evaporated to dry, diluted with water and extracted with DCM, dried over anhydrous Na$_2$SO$_4$, filtrated and evaporated to dry, and used for the next step directly.

The product obtained in the previous step was added in a 100 mL one-neck flask, and acetic acid (6 mL) was added, reduced iron powder (0.14 g, 2.50 mmol) was added. The reaction mixture was reacted for 1.5 h at room temperature, filtrated to remove most of the iron powder, the pH value of the filtrate was adjusted to 11 with 10% NaOH aqueous solution, extracted with ethyl acetate, dried over anhydrous Na$_2$SO$_4$, filtrated and evaporated to dry, purified by preparative TLC to deliver compound N-(2-(6-amino-4-(3-chloro-4-fluorophenylamino)quinazolin-7-oxy)ethyl)methanesulfonamide (0.13 g, 60% yield). $^1$H-NMR (d-DMSO, 400 MHz, δ ppm): 9.31 (s, 1H), 8.74 (s, 1H), 8.22-8.24 (m, 1H), 7.85-7.89 (m, 1H), 7.57 (s, 1H), 7.54 (t, J=9.2 Hz, 1H), 4.36 (t, J=5.6 Hz, 2H), 3.06 (t, J=5.6 Hz, 2H).

c. Synthesis of (E)-N-(4-(3-chloro-4-fluorophenylamino)-7-(2-(methylsulfonamido)ethoxy)quinazolin-6-yl)-4-(dimethylamino)but-2-enamide (Compound 8)

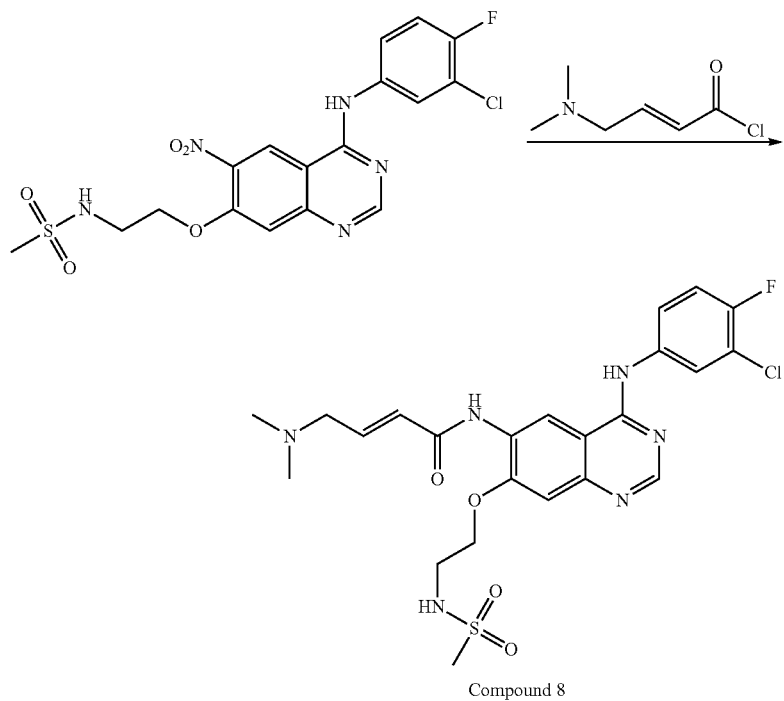

Compound 8

According to a method similar to the preparation of compound 1, taking N-(2-(6-amino-4-(3-chloro-4-fluorophenylamino)quinazolin-7-oxy)ethyl)methanesulfonamide as the starting material, compound 8 can be synthesized (51% yield) as a yellow solid. $^1$H-NMR (CD$_3$OD, 400 MHz, δ ppm): 9.01 (s, 1H), 8.49 (s, 1H), 8.03-8.06 (m, 1H), 7.68-7.72 (m, 1H), 7.28 (t, J=8.8 Hz, 1H), 7.19 (s, 1H), 6.99-7.03 (m, 1H), 6.67 (d, J=15.2 Hz, 1H), 4.28 (t, J=4.8 Hz, 2H), 3.66 (t, J=4.8 Hz, 2H), 3.53 (d, J=6.8 Hz, 2H), 3.09 (s, 3H), 2.58 (s, 6H).

Embodiment 9: Synthesis of (E)-N-(4-(3-chloro-4-fluorophenylamino)-7-(2-methoxyethylthio)quinazolin-6-yl)-4-(dimethylamino)but-2-enamide (Compound 9)

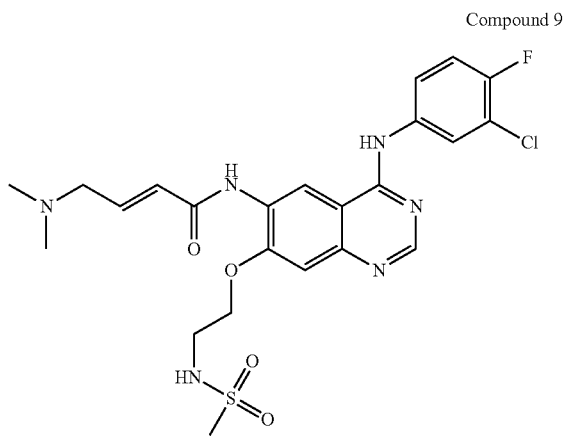 [SMILES: CN(C)C/C=C/C(=O)Nc1cc2c(Nc3ccc(F)c(Cl)c3)ncnc2cc1OCCNS(C)(=O)=O]

Compound 9 a. Synthesis of N-(3-chloro-4-fluorophenyl)-7-(2-methoxyethylthio)-6-nitro-4-quinazolinamine

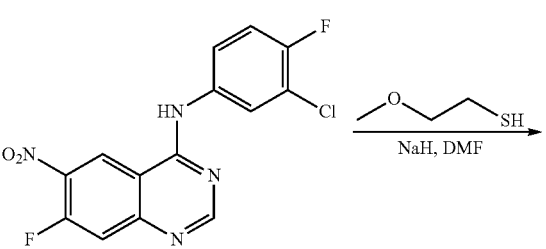

61

-continued

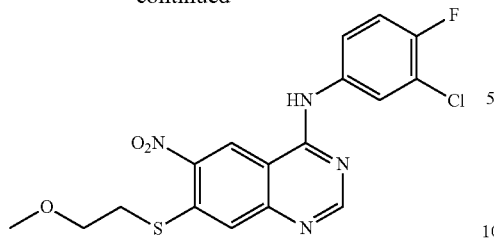

Under nitrogen gas atmosphere, 60 wt. % NaH (0.24 g, 5.95 mmol) was added into a three-neck flask containing DMF (5 mL), cooled to 0° C., into which a solution of 2-methoxyethanethiol (0.27 g, 2.98 mmol) in DMF (5 mL) was dripped. The reaction mixture was stirred for 0.5 h at room temperature and cooled to −15° C., then a suspension of compound N-(3-chloro-4-fluorophenyl)-7-fluoro-6-nitro-4-quinazolinamine (0.5 g, 1.49 mmol) in DMF (5 mL) was added, the reaction mixture was reacted at −15° C. for 1.5 h, then stirred at room temperature for 1 h. The reaction mixture was quenched with a lot of ice-water, a large amount of yellow solid was precipitated, filtrated and washed with water, the solid was collected and dried to deliver the product N-(3-chloro-4-fluorophenyl)-7-(2-methoxyethyl-thio)-6-nitro-4-quinazolinamine (0.24 g, 40% yield). ESI-MS (m/z): 409.1 [M+H]$^+$.

b. Synthesis of (E)-N-(4-(3-chloro-4-fluorophenylamino)-7-(2-methoxyethylthio)quinazolin-6-yl)-4-(dimethylamino)but-2-enamide (Compound 9)

According to a method similar to the preparation of compound 4, taking N-(3-chloro-4-fluorophenyl)-7-(2-methoxyethylthio)-6-nitro-4-quinazolinamine as the starting material, compound 9 can be synthesized. ESI-MS (m/z): 490.1 [M+H]$^+$.

Embodiment 10: Synthesis of (E)-N-(7-(2-ethoxy-ethoxy)-4-(3-ethynylphenylamino)quinazolin-6-yl)-4-(dimethylamino)but-2-enamide (Compound 10)

62 a. Synthesis of N-(3-ethynylphenyl)-7-fluoro-6-nitro-4-quinazolinamine

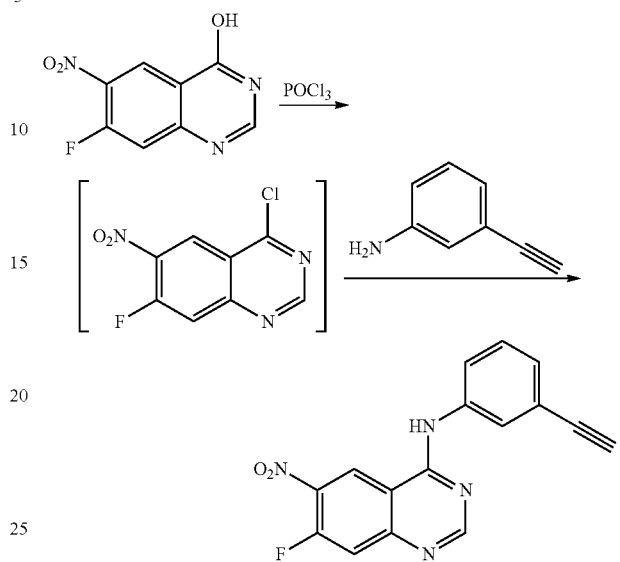

Compound 7-fluoro-6-nitro-4-hydroxyquinazoline (5 g, 23.9 mmol) was added into a 100 mL one-neck flask, POCl$_3$ (44.6 ml, 478 mmol) was added, heated to reflux at 150° C. for 5 h. The POCl$_3$ in the reaction solution was evaporated to dry, and the reaction mixture was diluted with anhydrous DCM, and evaporated to dry again. The procedure was repeated for 3 times and the reaction mixture was diluted with acetonitrile (100 mL), compound 3-amino phenylacetylene (5.6 g, 23.9 mmol) was added. The reaction mixture was heated to reflux overnight, a yellow solid was precipitated. The yellow solid in the reaction mixture was filtrated under vacuum, dried to deliver the product N-(3-ethynyl-phenyl)-7-fluoro-6-nitro-4-quinazolinamine (6.5 g, 88% yield). $^1$H-NMR (d-DMSO, 400 MHz, δ ppm): 9.85 (d, J=8.0 Hz, 1H), 8.91 (s, 1H), 7.94-7.98 (m, 2H), 7.83 (d, J=8.0 Hz, 1H), 7.50 (t, J=8.0 Hz, 1H), 7.40 (d, J=8.0 Hz, 1H), 4.28 (s, 1H).

b. Synthesis of 7-(2-ethoxyethoxy)-N-(3-ethynyl-phenyl)-6-amino-4-quinazolinamine Compound 10

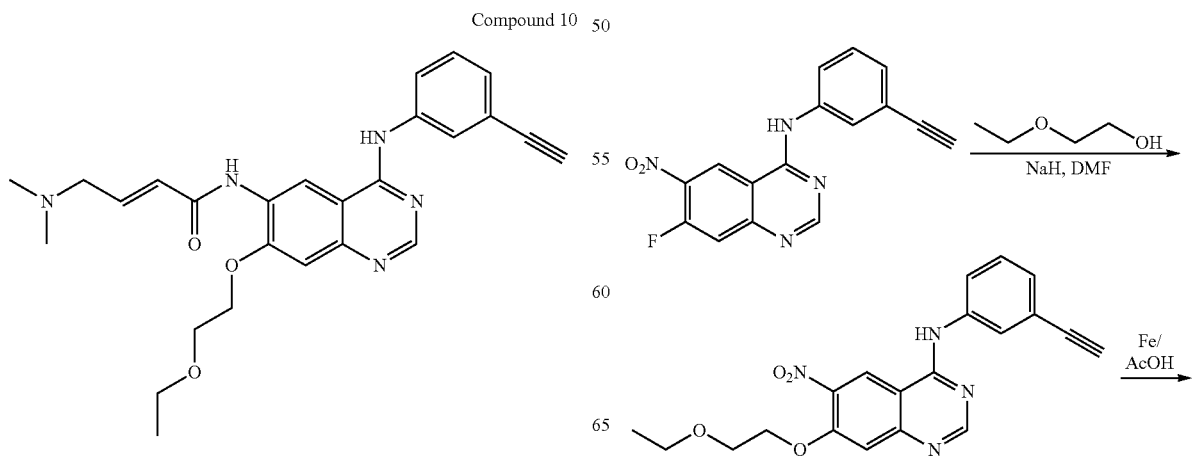

-continued

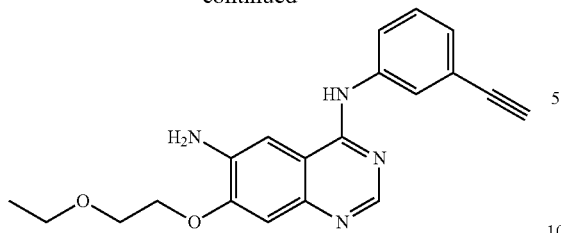

According to a method similar to the preparation of compound 1, 7-(2-ethoxyethoxy)-N-(3-ethynylphenyl)-6-nitro-4-quinazolinamine (85% yield) can be synthesized. $^1$H-NMR (d-DMSO, 400 MHz, δ ppm): 10.10 (s, 1H), 9.24 (s, 1H), 8.67 (s, 1H), 8.03 (s, 1H), 7.88 (d, J=8.0 Hz, 1H), 7.51 (s, 1H), 7.43 (t, J=8.0 Hz, 1H), 7.26 (d, J=8.0 Hz, 1H), 4.43 (t, J=4.4 Hz, 2H), 4.23 (s, 1H), 3.77 (t, J=4.4 Hz, 2H), 3.52-3.54 (m, 2H), 1.12 (t, J=6.8 Hz, 3H).

According to a method similar to the preparation of compound 4, 7-(2-ethoxyethoxy)-N-(3-ethynylphenyl)-6-amino-4-quinazolinamine (88% yield) can be synthesized as a yellow solid. $^1$H-NMR (d-DMSO, 400 MHz, δ ppm): 9.34 (s, 1H), 8.37 (s, 1H), 8.05 (s, 1H), 7.87-7.89 (m, 1H), 7.43 (s, 1H), 7.34 (t, J=8.0 Hz, 1H), 7.14 (d, J=8.0 Hz, 1H), 7.11 (s, 1H), 5.30 (s, 2H), 4.28 (t, J=4.4 Hz, 2H), 4.17 (s, 1H), 3.81 (t, J=4.4 Hz, 2H), 3.55-3.56 (m, 2H), 1.15 (t, J=7.2 Hz, 3H).

c. Synthesis of (E)-N-(7-(2-ethoxyethoxy)-4-(3-ethynylphenylamino)quinazolin-6-yl)-4-(dimethylamino)but-2-enamide (Compound 10)

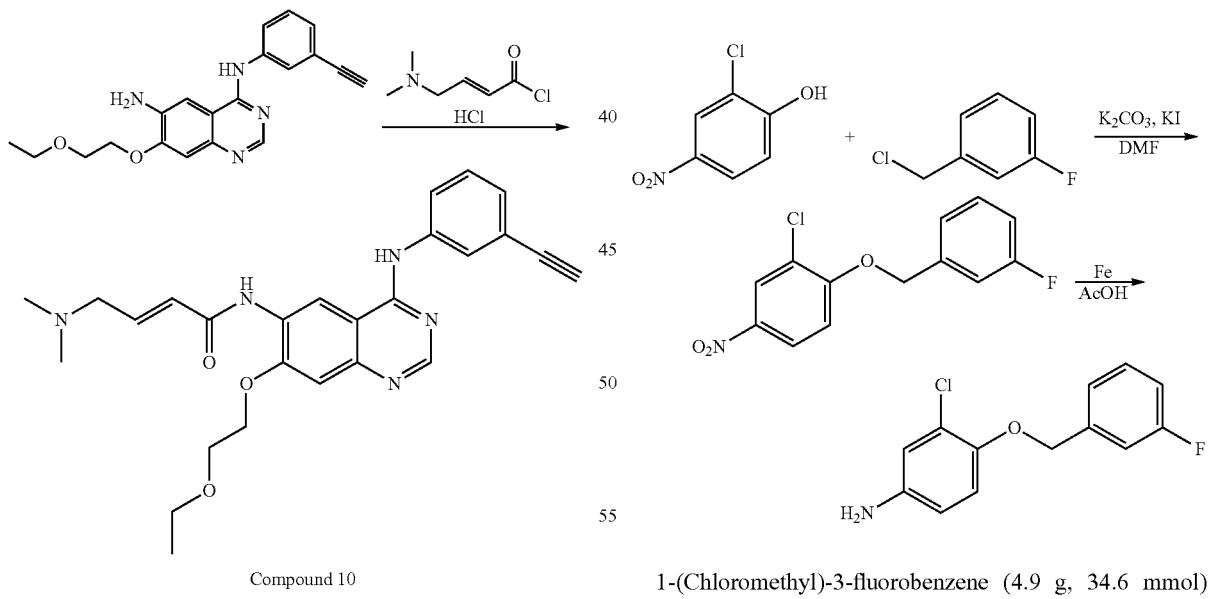

Compound 10

According to a method similar to the preparation of compound 1, taking 7-(2-ethoxyethoxy)-N-(3-ethynylphenyl)-6-amino-4-quinazolinamine as the starting material, compound 10 (35% yield) can be synthesized as a yellow solid. $^1$H-NMR (d-DMSO, 400 MHz, δ ppm): 9.75 (s, 1H), 9.56 (s, 1H), 8.91 (s, 1H), 8.53 (s, 1H), 8.01 (s, 1H), 7.86-7.89 (m, 1H), 7.38 (t, J=8.0 Hz, 1H), 7.32 (s, 1H), 7.20 (d, J=8.0 Hz, 1H), 6.78-6.82 (m, 1H), 6.56 (d, J=16 Hz, 1H), 4.33 (t, J=4.4 Hz, 2H), 4.19 (s, 1H), 3.84 (t, J=4.4 Hz, 2H), 3.54-3.56 (m, 2H), 3.16 (d, J=6.8 Hz, 2H), 2.24 (s, 6H), 1.13 (t, J=7.2 Hz, 3H).

Embodiment 11: Synthesis of (E) N (4 (4 (3 fluorobenzyloxy)3-chlorophenylamino)-7-(2-ethoxyethoxy)quinazolin-6-yl)-4-(dimethylamino)but-2-enamide (Compound 11)

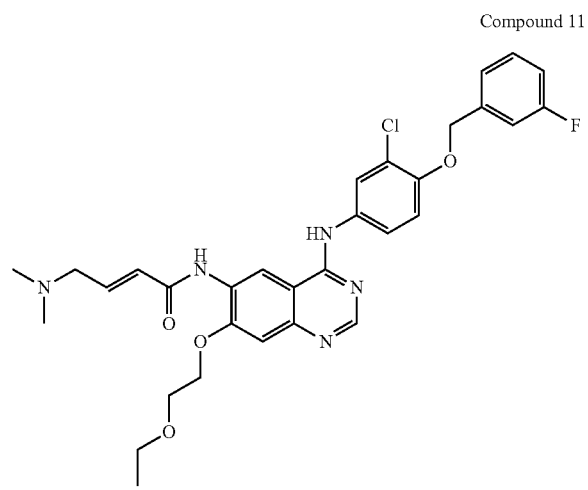 [SMILES: CCOCCOc1cc2ncnc(Nc3ccc(OCc4cccc(F)c4)c(Cl)c3)c2cc1NC(=O)/C=C/CN(C)C]

Compound 11 a. Synthesis of 3-chloro-4-(3-fluorobenzyloxy)aniline 1-(Chloromethyl)-3-fluorobenzene (4.9 g, 34.6 mmol) was added into DMF (48 mL) and stirred to dissolve completely, K$_2$CO$_3$ (9.6 g, 69 mmol) was added and stirred for 30 min. 2-Chloro-4-nitrophenol (6 g, 34.6 mmol), KI (0.29 g, 1.7 mmol) were added at 60° C. under an oil bath, then reacted for 3 h. The reaction solution was added into ice-water, a large amount of solid was precipitated after stirring, filtrated to deliver the product 2-chloro-1-(3-fluorobenzyloxy)-4-nitrobenzene, which was used in the next step directly.

According to a method similar to the preparation of compound 4, taking 2-chloro-1-(3-fluorobenzyloxy)-4-nitrobenzene obtained in the previous step as the starting material, 3-chloro-4-(3-fluorobenzyloxy)aniline (81% yield) can be synthesized. ESI-MS (m/z): 252.1 [M+H]⁺.

b. Synthesis of N-4-(3-fluorobenzyloxy)-3-chlorophenyl)-7-fluoro-6-nitro-4-quinazolinamine

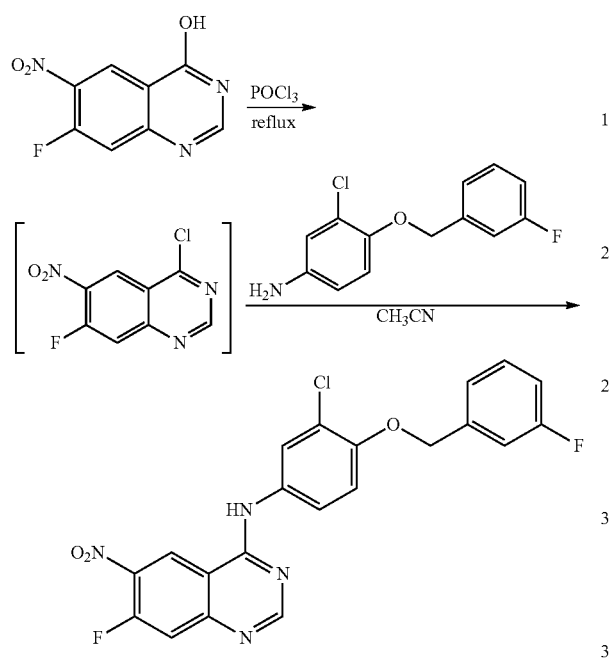

Compound 7-fluoro-6-nitro-4-hydroxyquinazoline (5 g, 23.9 mmol) was added into a 100 mL one-neck flask, POCl₃ (44.6 mL, 478 mmol) was added, heated to reflux at 150° C. for 5 h. The POCl₃ in the reaction mixture was evaporated to dry, and the reaction mixture was diluted with anhydrous DCM, and evaporated to dry again. The procedure was repeated for 3 times and the reaction mixture was diluted with acetonitrile (100 mL), compound 3-chloro-4-(3-fluorobenzyloxy)aniline (6.0 g, 23.9 mmol) was added, the reaction mixture was heated to reflux overnight, a yellow solid was precipitated, the yellow solid in the reaction mixture was filtrated under vacuum, dried to deliver the product N-4-(3-fluorobenzyloxy)-3-chlorophenyl)-7-fluoro-6-nitro-4-quinazolinamine (8.2 g, 78% yield), which was used for the next step directly without further purification. ESI-MS (m/z): 443.1 [M+H]⁺.

c. Synthesis of N-(4-(3-fluorobenzyloxy)-3-chlorophenyl)-7-(2-ethoxyethoxy)-6-amine-4-quinazolinamine

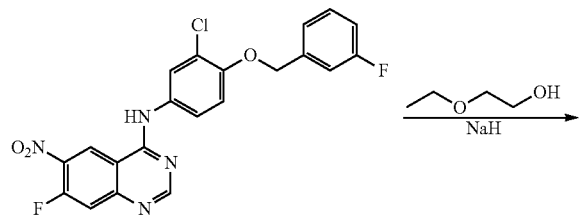

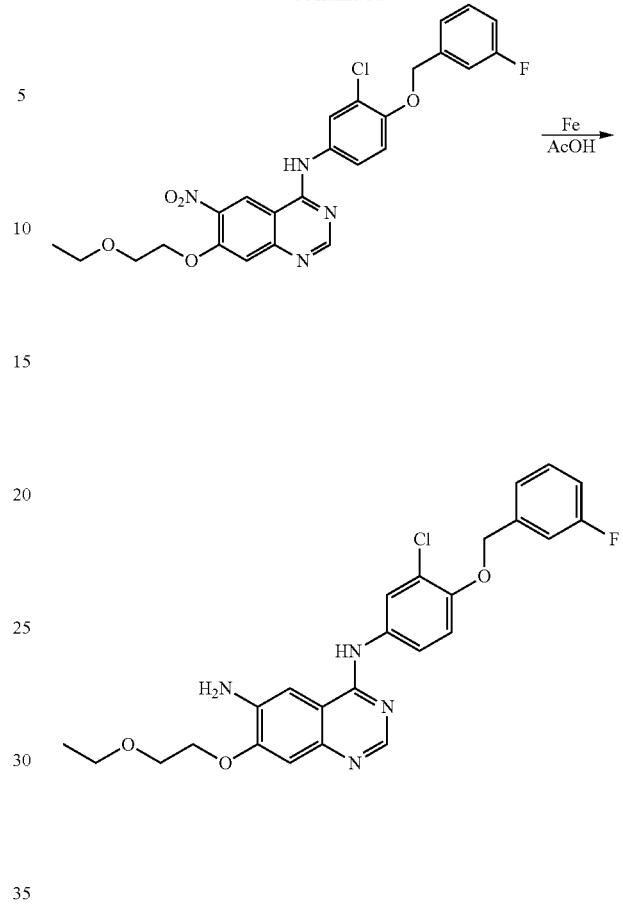

According to a method similar to the preparation of compound 1, taking N-(4-(3-fluorobenzyloxy)-3-chlorophenyl)-7-fluoro-6-nitro-4-quinazolinamine and 2-ethoxyethanol as the starting materials, N-(4-(3-fluorobenzyloxy)-3-chlorophenyl)-7-(2-ethoxyethoxy)-6-nitro-4-quinazolinamine (83% yield) can be synthesized. ¹H-NMR (d-DMSO, 400 MHz, δ ppm): 10.06 (s, 1H), 9.18 (s, 1H), 8.61 (s, 1H), 7.95 (s, 1H), 7.68-7.71 (m, 1H), 7.42-7.46 (m, 2H), 7.28-7.32 (m, 3H), 7.16-7.18 (m, 1H), 5.25 (s, 2H), 4.40 (t, J=4.4 Hz, 2H), 3.75 (t, J=4.4 Hz, 2H), 3.52-3.54 (m, 2H), 1.12 (t, J=6.8 Hz, 3H).

According to a method similar to the preparation of compound 4, taking N-(4-(3-fluorobenzyloxy)-3-chlorophenyl)-7-(2-ethoxyethoxy)-6-nitro-4-quinazolinamine as the starting material, N-(4-(3-fluorobenzyloxy)-3-chlorophenyl)-7-(2-ethoxyethoxy)-6-amino-4-quinazolinamine (91% yield) can be synthesized as a yellow solid. ¹H-NMR (d-DMSO, 400 MHz, δ ppm): 9.30 (s, 1H), 8.33 (s, 1H), 8.02 (s, 1H), 7.68-7.71 (m, 1H), 7.46-7.47 (m, 1H), 7.40 (s, 1H), 7.32-7.33 (m, 2H), 7.18-7.23 (m, 2H), 7.09 (s, 1H), 5.28 (s, 2H), 5.23 (s, 2H), 4.28 (t, J=4.4 Hz, 2H), 3.81 (t, J=4.4 Hz, 2H), 3.54-3.56 (m, 2H), 1.15 (t, J=6.8 Hz, 3H).

d. Synthesis of (E)-N-(4-(4-(3-fluorobenzyloxy)3-chlorophenylamino)-7-(2-ethoxyethoxy)quinazolin-6-yl)-4-(dimethylamino)but-2-enamide (Compound 11)

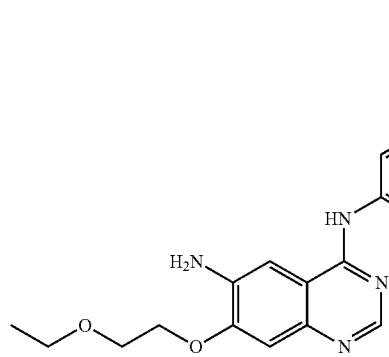 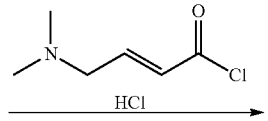

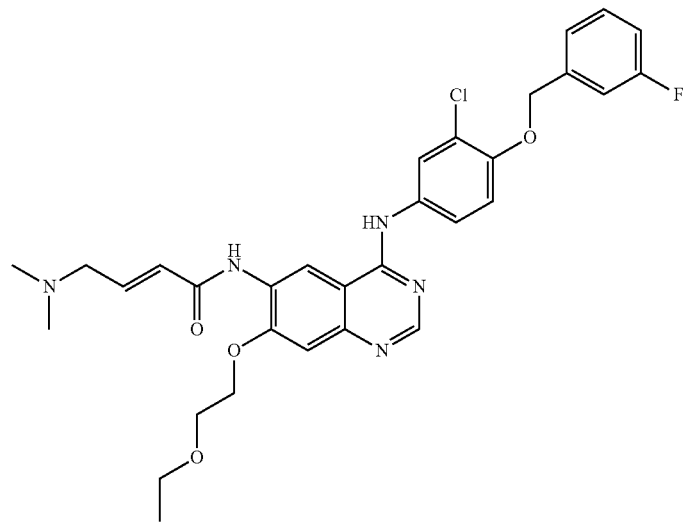

Compound 11

According to a method similar to the preparation of compound 1, taking N-(4-(3-fluorobenzyloxy)-3-chlorophenyl)-7-(2-ethoxyethoxy)-6-amino-4-quinazolinamine as the starting material, compound 11 (50% yield) can be synthesized as a yellow solid. $^1$H-NMR (d-DMSO, 400 MHz, δ ppm): 9.68 (s, 1H), 9.55 (s, 1H), 8.87 (s, 1H), 8.48 (s, 1H), 7.97 (s, 1H), 7.68-7.71 (m, 1H), 7.46-7.48 (m, 1H), 7.30-7.34 (m, 3H), 7.23-7.25 (m, 2H), 6.78-6.82 (m, 1H), 6.57 (d, J=16 Hz, 1H), 5.25 (s, 2H), 4.33 (t, J=4.4 Hz, 2H), 3.84 (t, J=4.4 Hz, 2H), 3.54-3.56 (m, 2H), 3.20 (d, J=6.8 Hz, 2H), 2.26 (s, 6H), 1.13 (t, J=6.8 Hz, 3H).

Embodiment 12: Synthesis of (E)-N-(4-(3-chloro-4-(pyridin-2-ylmethoxy)phenylamino)-7-(2-ethoxyethoxy)quinazolin-6-yl)-4-(dimethylamino)but-2-enamide (Compound 12)

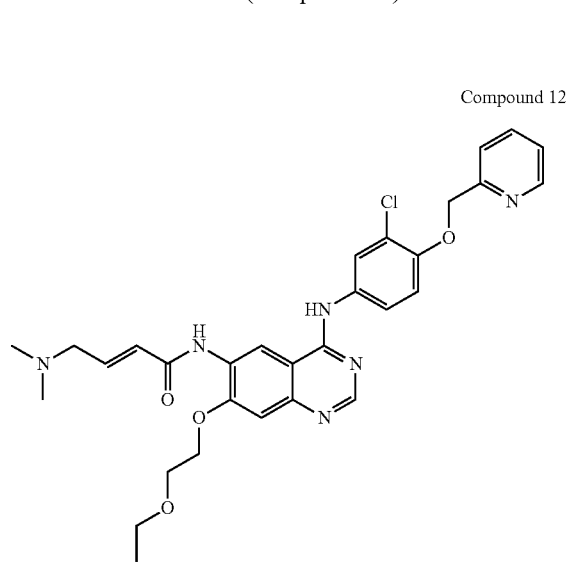

Compound 12 a. Synthesis of 3-chloro-4-(pyridin-2-ylmethoxy)aniline

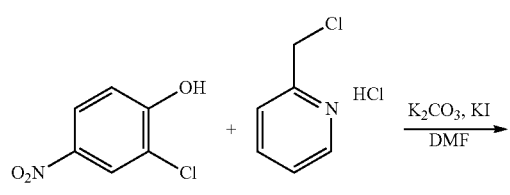

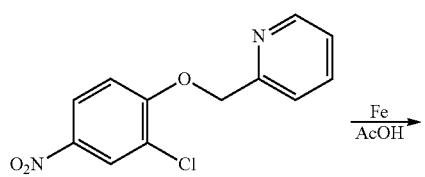

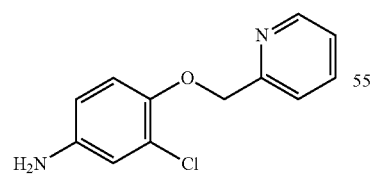

According to the literature (Bioorganic and Medicinal Chemistry 2013, 21, 3090-3104), 3-chloro-4-(pyridin-2-ylmethoxy)aniline can be synthesized. $^1$H-NMR (d-DMSO, 400 MHz, δ ppm): 8.55 (d, J=4, 1H), 7.85 (t, J=7.6, 1H), 7.55 (d, J=8.8, 1H), 7.35 (m, 1H), 6.90 (d, J=8.8, 1H), 6.65 (s, 1H), 6.45 (dd, $J_1$=8.8, $J_2$=2.4, 1H), 5.07 (s, 2H), 4.95 (s, 2H).

b. Synthesis of N-(4-(3-chloro-4-(pyridin-2-ylmethoxy)phenylamino)-7-fluoro-6-nitro-4-quinazolinamine

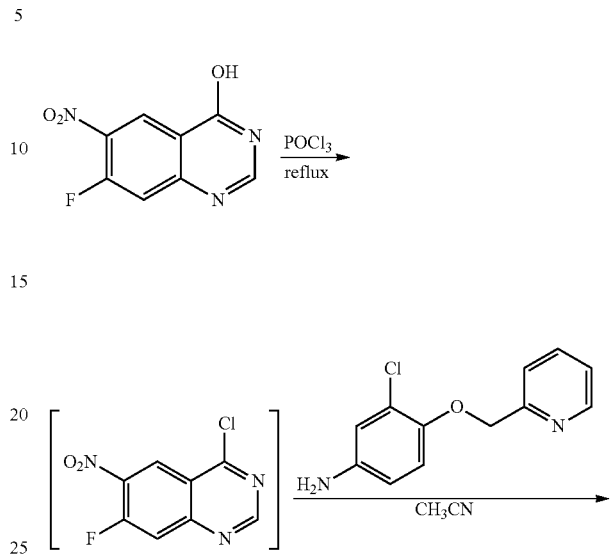

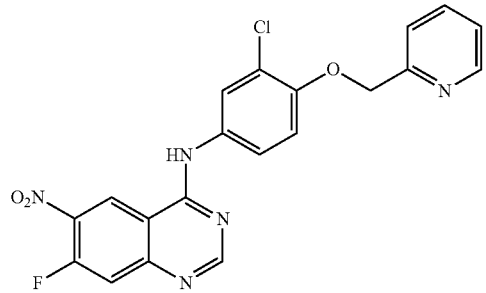

According to a method similar to the preparation of compound 1, N-(3-chloro-4-(pyridin-2-ylmethoxy)phenylamino)-7-fluoro-6-nitro-4-quinazolinamine (52% yield) can be synthesized. $^1$H-NMR (d-DMSO, 400 MHz, δ ppm): 9.64-9.65 (m, 1H), 8.78 (s, 1H), 8.01-8.03 (m, 2H), 7.85-7.88 (m, 1H), 7.67-7.72 (m, 2H), 7.47-7.49 (m, 2H), 7.33-7.35 (m, 1H), 5.37 (s, 2H).

c. Synthesis of N-(4-(3-chloro-4-(pyridin-2-ylmethoxy)phenylamino)-7-(2-ethoxyethoxy)-6-nitro-4-quinazolinamine

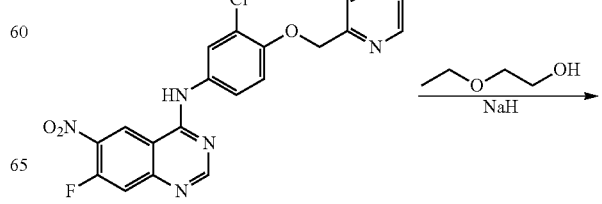

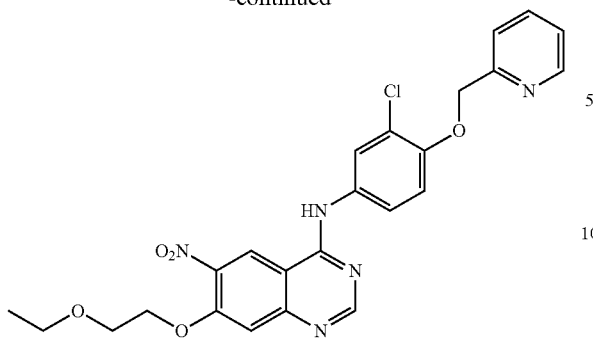

According to a method similar to the preparation of compound 1, N-(4-(3-chloro-4-(pyridin-2-ylmethoxy)phenylamino)-7-(2-ethoxyethoxy)-6-nitro-4-quinazolinamine (73% yield) can be synthesized. ¹H-NMR (d-DMSO, 400 MHz, δ ppm): 10.07 (s, 1H), 9.19 (s, 1H), 8.61 (m, 2H), 8.00-8.01 (m, 1H), 7.89-7.91 (m, 1H), 7.86-7.88 (m, 1H), 7.67-7.69 (m, 1H), 7.67 (s, 1H), 7.48-7.57 (m, 1H), 7.37 (d, J=8.0 Hz, 1H), 5.29 (s, 2H), 4.41 (t, J=4.4 Hz, 2H), 3.76 (t, J=4.4 Hz, 2H), 3.52-3.54 (m, 2H), 1.12 (t, J=6.8 Hz, 3H).

d. Synthesis of N-(4-(3-chloro-4-(pyridin-2-ylmethoxy)phenylamino)-7-(2-ethoxyethoxy)-6-amino-4-quinazolineamine

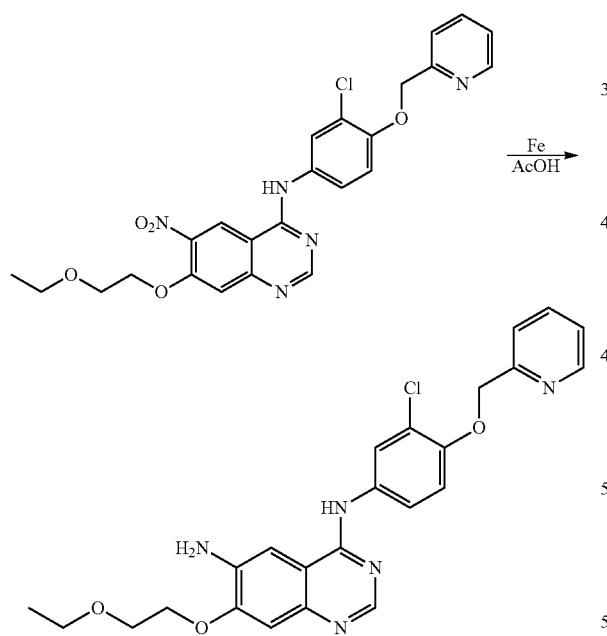

According to a method similar to the preparation of compound 4, N-(4-(3-chloro-4-(pyridin-2-ylmethoxy)phenylamino)-7-(2-ethoxyethoxy)-6-amino-4-quinazolineamine (82% yield) can be synthesized. ¹H-NMR (d-DMSO, 400 MHz, δ ppm): 9.34 (br, 1H), 8.59-8.60 (m, 1H), 8.36 (s, 1H), 8.05 (s, 1H), 7.86-7.89 (m, 1H), 7.70-7.72 (m, 1H), 7.58-7.60 (m, 1H), 7.44 (s, 1H), 7.34-7.37 (m, 1H), 7.22 (d, J=8.0 Hz, 1H), 7.11 (s, 1H), 5.25 (s, 2H), 5.23 (s, 2H), 4.27 (t, J=4.4 Hz, 2H), 3.87 (t, J=4.4 Hz, 2H), 3.52-3.54 (m, 2H), 1.14 (t, J=6.8 Hz, 3H).

e. Synthesis of (E)-N-(4-(3-chloro-4-(pyridin-2-ylmethoxy)phenylamino)-7-(2-ethoxyethoxy)quinazolin-6-yl)-4-(dimethylamino)but-2-enamide (Compound 12)

According to a method similar to the preparation of compound 1, taking N-(4-(3-chloro-4-(pyridin-2-ylmethoxy)phenylamino)-7-(2-ethoxyethoxy)-6-amino-4-quinazolineamine as the starting material, compound 12 (82% yield) can be synthesized as a yellow solid. ¹H-NMR (d-DMSO, 400 MHz, δ ppm): 9.69 (s, 1H), 9.54 (s, 1H), 8.87 (s, 1H), 8.60-8.61 (m, 1H), 8.48 (s, 1H), 7.97-7.98 (m, 1H), 7.88-7.89 (m, 1H), 7.67-7.69 (m, 1H), 7.58-7.60 (m, 1H), 7.35-7.38 (m, 1H), 7.29 (s, 1H), 7.23-7.26 (m, 1H), 6.80-6.83 (m, 1H), 6.55 (d, J=16 Hz, 1H), 5.28 (s, 2 H), 4.33 (t, J=4.4 Hz, 2H), 3.83 (t, J=4.4 Hz, 2H), 3.54-3.56 (m, 2H), 3.13 (d, J=6.8 Hz, 2H), 2.22 (s, 6H), 1.14 (t, J=6.8 Hz, 3H).

Embodiment 13: Synthesis of (E)-N-(4-(3-chloro-4-(2,2,2-trifluoroethoxy)phenylamino)-7-(2-ethoxyethoxy)quinazolin-6-yl)-4-(dimethylamino)but-2-enamide (Compound 13)

Compound 13

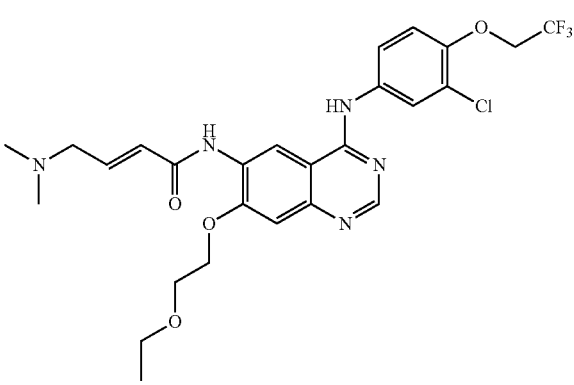

a. Synthesis of 3-chloro-4-(2,2,2-trifluoroethoxy)aniline

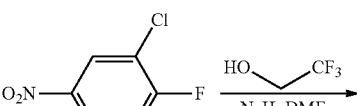

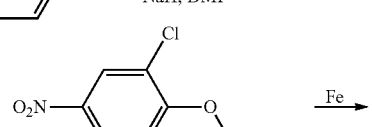

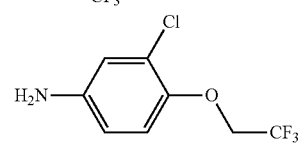

Under nitrogen gas atmosphere, 60 wt. % NaH (0.18 g, 4.52 mmol) was added into a three-neck flask containing DMF (5 mL), cooled to 0° C., into which a solution of 2,2,2-trifluoroethanol (0.23 g, 2.26 mmol) in DMF (5 mL) was dripped, a lot of bubbles appeared in the system at the moment, the reaction mixture was stirred for 0.5 h at room temperature and cooled to −15° C. A suspension of compound 2-chloro-1-fluoro-4-nitrobenzene (0.198 g, 1.13 mmol) in DMF (5 mL) was added, during the dripping the system turned to blood red. The reaction mixture was reacted at −15° C. for 1.5 h, then stirred at room temperature for 1 h. The reaction mixture was quenched with a lot of ice-water, a large amount of yellow solid was precipitated, filtrated and washed with water, the solid was collected and dried to deliver the product 2-chloro-4-nitro-1-(2,2,2-trifluoroethoxy)benzene (0.234 g, 81% yield). $^1$H-NMR (CDCl$_3$, 400 MHz, δ ppm): 8.32 (d, J=2.8, 1H), 8.17 (dd, J$_1$=9.2, J$_2$=2.8, 1H), 7.03 (d, J=9.2, 1H), 4.50-4.56 (m, 2H).

Compound 2-chloro-4-nitro-1-(2,2,2-trifluoroethoxy)benzene (0.234 g, 0.92 mmol) was added into a 100 mL one-neck flask, acetic acid (8 mL) was added, iron powder (0.26 g, 4.69 mmol) was added, reacted for 1.5 h at room temperature. The reaction mixture was filtrated to remove most of the iron powder, and the pH value of the filtrate was adjusted to 11 with 10% NaOH aqueous solution, a large amount of solid was precipitated, filtrated and washed with water, the solid was dried to deliver a yellow solid 3-chloro-4-(2,2,2-trifluoroethoxy)aniline (0.19 g, 90% yield). ESI-MS (m/z): 226.2 [M+H]$^+$.

b. Synthesis of (E)-N-(4-(3-chloro-4-(2,2,2-trifluoroethoxy)phenylamino)-7-(2-ethoxyethoxy)quinazolin-6-yl)-4-(dimethylamino)but-2-enamide (Compound 13)

According to a method similar to the preparation of compound 1, taking 3-chloro-4-(2,2,2-trifluoroethoxy)aniline as the starting material, compound 13 (48% yield) can be synthesized. $^1$H-NMR (CD$_3$OD, 400 MHz, δ ppm): 8.89 (s, 1H), 8.43 (s, 1H), 7.89 (s, 1H), 7.61 (d, J=7.2, 1H), 7.14-7.17 (m, 2H), 6.98-7.02 (m, 1H), 6.64-6.67 (m, 1H), 4.60-4.62 (m, 2H), 4.35 (t, J=4.4 Hz, 2H), 3.95 (t, J=4.4 Hz, 2H), 3.67-3.69 (m, 4H), 2.66 (s, 6H), 1.28 (t, J=7.2 Hz, 3H).

Embodiment 14: Synthesis of (E)-N-(4-(3-chloro-4-(trifluoromethoxy)phenylamino)-7-(2-ethoxyethoxy)quinazolin-6-yl)-4-(dimethylamino)but-2-enamide (Compound 14)

Compound 14

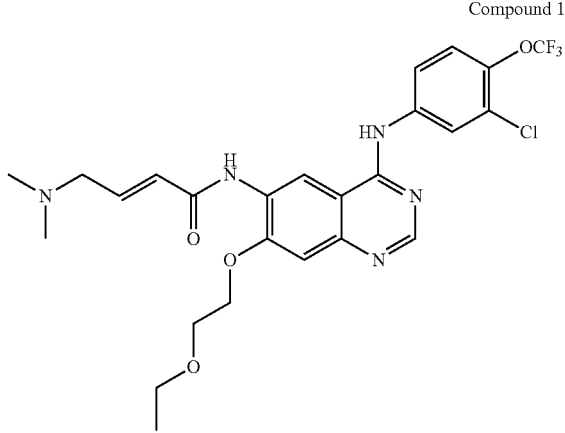

a. Synthesis of 3-chloro-4-(trifluoromethoxy)aniline

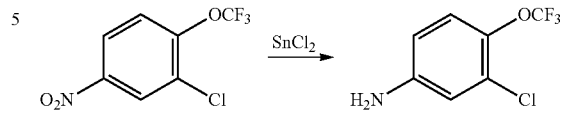

3-Chloro-4-trifluoroethoxynitrobenzene (2.6 g, 11 mmol) was dissolved in ethanol (20 mL), a solution of SnCl$_2$ (8.6 g, 46 mmol) dissolved in conc. hydrochloric acid (10 mL) was dripped in at a temperature below 30° C., reacted for 2 h at room temperature, then for 0.5 h at 50° C. The reaction mixture was poured into water, the pH value was adjusted to 7-8 with 10% NaOH aqueous solution, extracted with diethyl ether, dried over anhydrous Na$_2$SO$_4$, filtrated, evaporated to dry, purified by column chromatography to deliver 3-chloro-4-(trifluoromethoxy)aniline (2 g, 86% yield). ESI-MS (m/z): 212.1 [M+H]$^+$.

b. Synthesis of (E)-N-(4-(3-chloro-4-(trifluoromethoxy)phenylamino)-7-(2-ethoxyethoxy)quinazolin-6-yl)-4-(dimethylamino)but-2-enamide (Compound 14)

According to a method similar to the preparation of compound 1, taking 3-chloro-4-(2,2,2-trifluoroethoxy)aniline as the starting material, compound 14 can be synthesized. ESI-MS (m/z): 554.2 [M+H]$^+$.

Embodiment 15: Synthesis of (E)-N-(4-(3-chloro-4-(2-methoxyethoxy)phenylamino)-7-(2-ethoxyethoxy)quinazolin-6-yl)-4-(dimethylamino)but-2-enamide (Compound 15)

Compound 15

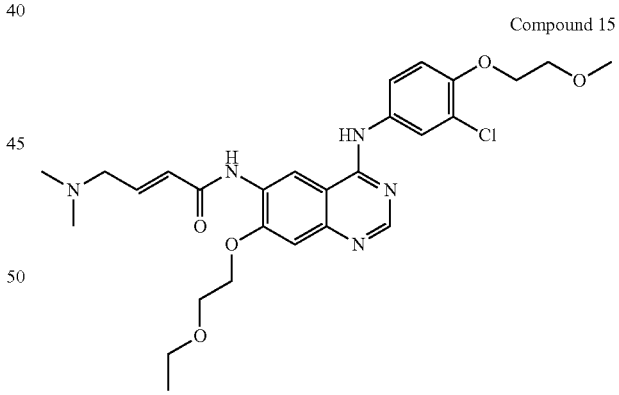

a. Synthesis of 3-chloro-4-(2-ethoxyethoxy)aniline

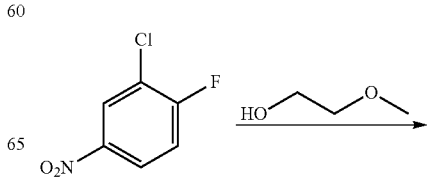

-continued

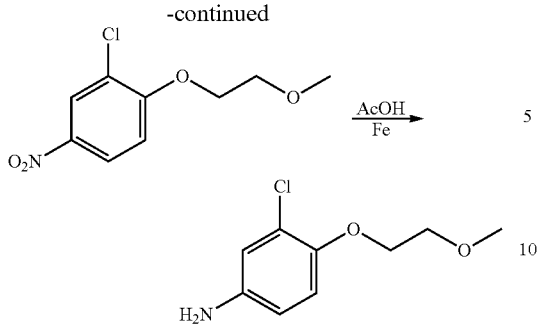

2-methoxyethan-1-ol (1.3 g, 17.1 mmol) and DMF (15 mL) were added into a 100 mL one-neck flask, after stirring for 10 min, NaH (1.37 g, 34.2 mmol) was added under an ice bath, after reacting for 30 min, a solution of 2-chloro-4-nitro-fluorobenzene (1 g, 5.7 mmol) in DMF (15 mL) was added, stirred to react for 1 h. The reaction mixture was poured into water, extracted with DCM for 3 times, the organic phases were combined, dried over anhydrous $Na_2SO_4$, evaporated to dry to deliver compound 2-chloro-1-(2-methoxyethoxy)-4-nitrobenzene (used for the next step directly).

2-Chloro-1-(2-methoxyethoxy)-4-nitrobenzene obtained from the previous step was added into a 100 mL one-neck flask, HAc (13 mL) was added, after stirring to dissolve completely, iron powder (3.2 g, 57 mmol) was added, reacted for 2 h at 40° C. The reaction mixture was added into water, extracted with EA for 3 times. The organic phase was washed with saturated sodium bicarbonate solution until the aqueous phase was alkaline, the organic phase was dried and evaporated to dry, purified by column chromatography to deliver the product 3-chloro-4-(2-ethoxyethoxy)aniline (0.4 g, 38% yield). $^1$H-NMR (d-DMSO, 400 MHz, δ ppm): 6.84 (d, J=8.8, 1H), 6.61 (d, J=2.8, 1H), 6.45 (dd, $J_1$=8.8, $J_2$=2.8, 1H), 4.92 (s, 2H), 3.98 (t, J=4.4, 2H), 3.60 (t, J=4.4, 2H), 3.34 (s, 3H).

b. Synthesis of (E)-N-(4-(3-chloro-4-(2-methoxyethoxy)phenylamino)-7-(2-ethoxyethoxy)quinazolin-6-yl)-4-(dimethylamino)but-2-enamide (Compound 15)

According to a method similar to the preparation of compound 1, taking 1-fluoro-2-chloro-4-nitrobenzene and 2-methoxyethan-1-ol as the starting materials, compound 15 (67% yield) can be synthesized. $^1$H-NMR (d-DMSO, 400 MHz, δ ppm): 9.68 (s, 1H), 9.58 (s, 1H), 8.87 (s, 1H), 8.49 (s, 1H), 7.94 (d, J=2.4 Hz, 1H), 7.70 (dd, $J_1$=2.4 Hz, $J_2$=8.8 Hz, 1H), 7.30 (s, 1H), 7.18 (d, J=8.8 Hz 1H), 6.77-6.84 (m, 1H), 6.52-6.60 (m, 1H), 4.35 (t, J=4.4 Hz, 2H), 4.19 (t, J=4.4 Hz, 2H), 3.84 (t, J=4.4 Hz, 2H), 3.71 (t, J=4.4 Hz, 2H), 3.54 (m, 2H), 3.33-3.37 (m, 2H), 3.32 (s, 3H), 2.23 (s, 6H), 1.14 (t, J=6.8 Hz, 3H).

Embodiment 16: Synthesis of (E)-N-(7-(2-ethoxy-ethoxy)-4-(3-fluoro-4-(2-methoxyethoxy)phe-nylamino)quinazolin-6-yl)-4-(dimethylamino)but-2-enamide (Compound 16)

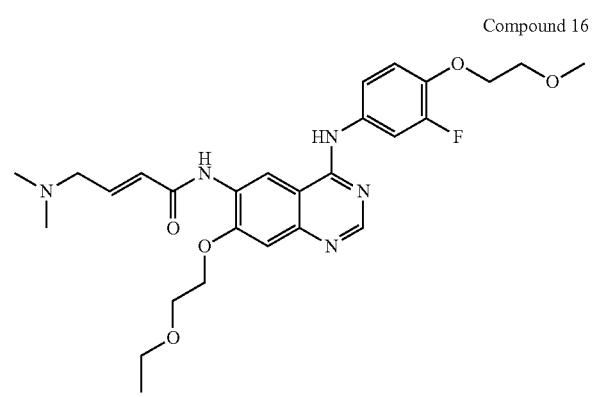

Compound 16

According to a method similar to the preparation of compound 15, taking 1,2-difluoro-4-nitrobenzene and 2-methoxyethan-1-ol as the starting materials, compound 16 can be synthesized. ESI-MS (m/z): 528.3 $[M+H]^+$.

Embodiment 17: Synthesis of (E)-N-(4-(3-chloro-4-(2-ethoxyethoxy)phenylamino)-7-(2-ethoxyethoxy)quinazolin-6-yl)-4-(dimethylamino)but-2-enamide (Compound 17)

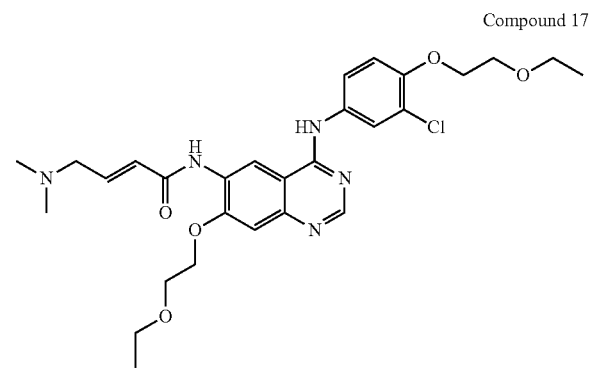 [SMILES: CCOCCOc1ccc(Nc2ncnc3cc(OCCOCC)c(NC(=O)/C=C/CN(C)C)cc23)cc1Cl]

Compound 17 a. Synthesis of 3-chloro-4-(2-ethoxyethoxy)aniline

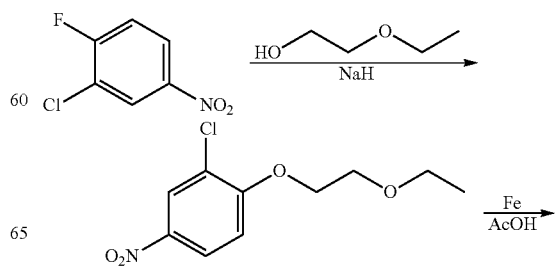

-continued

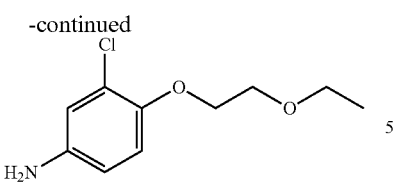

According to a method similar to the preparation of compound 4, taking 2-ethoxyethanol as the starting material, 3-chloro-4-(2-ethoxyethoxy)aniline (82% yield) can be synthesized. $^1$H-NMR (d-DMSO, 400 MHz, δ ppm): 6.85 (d, J=8.8, 1H), 6.64 (d, J=2.4, 1H), 6.49 (dd, J$_1$=8.8, J$_2$=2.4, 1H), 5.11 (s, 2H), 3.97 (t, J=4.4, 2H), 3.64 (t, J=4.4, 2H), 3.47-3.52 (m, 2H), 1.11 (t, J=6.8, 3H).

b. Synthesis of (E)-N-(4-(3-chloro-4-(2-ethoxyethoxy)phenylamino)-7-(2-ethoxyethoxy)quinazolin-6-yl)-4-(dimethylamino)but-2-enamide (Compound 17)

According to a method similar to the preparation of compound 1, taking 3-chloro-4-(2-ethoxyethoxy)aniline as the starting material, compound 17 (48% yield) can be synthesized. $^1$H-NMR (d-DMSO, 400 MHz, δ ppm): 9.68 (s, 1H), 9.56 (s, 1H), 8.88 (s, 1H), 8.49 (s, 1H), 7.95 (d, J=2.4 Hz, 1H), 7.70 (dd, J$_1$=2.4 Hz, J$_2$=8.8 Hz, 1H), 7.30 (s, 1H), 7.18 (d, J=8.8 Hz 1H), 6.80-6.84 (m, 1H), 6.55-6.59 (m, 1H), 4.35 (t, J=4.4 Hz, 2H), 4.19 (t, J=4.4 Hz, 2H), 3.84 (t, J=4.4 Hz, 2H), 3.75 (t, J=4.4 Hz, 2H), 3.53-3.58 (m, 4H), 3.2 (d, J=5.6 Hz, 2H), 2.26 (s, 6H), 1.14 (t, J=6.8 Hz, 6H).

Embodiment 18: Synthesis of (E)-N-(7-(2-ethoxyethoxy)-4-(4-(2-ethoxyethoxy)-3-fluorophenylamino)quinazolin-6-yl)-4-(dimethylamino)but-2-enamide (Compound 18)

Compound 18

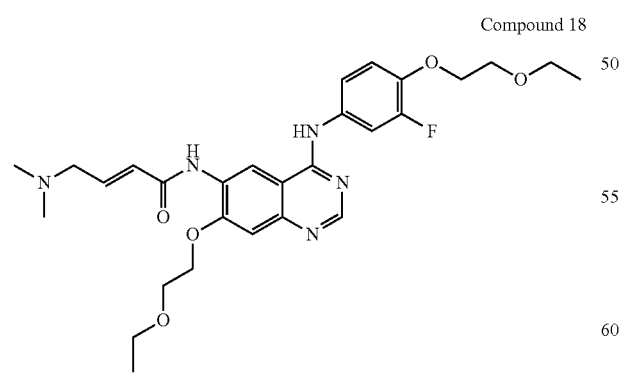

According to a method similar to the preparation of compound 17, taking 1,2-difluoro-4-nitrobenzene and 2-ethoxyethanol as the starting materials, compound 18 can be synthesized. ESI-MS (m/z): 542.3 [M+H]$^+$.

Embodiment 19: Synthesis of (E)-N-(4-(3-chloro-4-(2-(2,2,2-trifluoroethoxy)ethoxy)phenylamino)-7-(2-ethoxyethoxy)quinazolin-6-yl)-4-(dimethylamino)but-2-enamide (Compound 19)

Compound 19

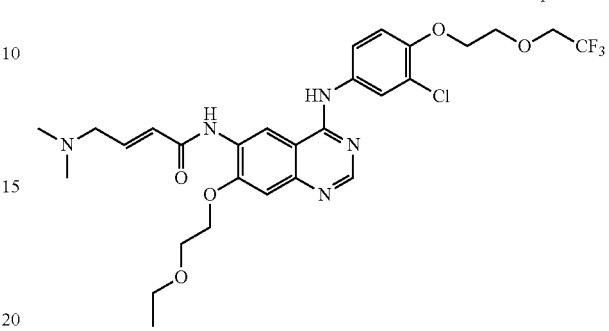

According to a method similar to the preparation of compound 15, taking 1-fluoro-2-chloro-4-nitrobenzene and 2-(2,2,2-trifluoroethoxy)ethanol as the starting materials, compound 19 can be synthesized. ESI-MS (m/z): 612.2 [M+H]$^+$.

Embodiment 20: Synthesis of (E)-N-(4-(3-chloro-4-((2-(methylsulfonyl)ethyl)amino)phenylamino)-7-(2-ethoxyethoxy)quinazolin-6-yl)-4-(dimethylamino)but-2-enamide (Compound 20)

Compound 20 a. Synthesis of 2-chloro-N$^1$-(2-(methylsulfonyl)ethyl)benzene-1,4-diamine

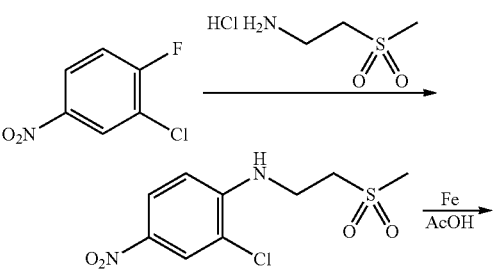

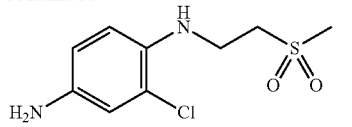

TEA (8 mL, 57 mmol) was dripped into a mixture of compound 2-chloro-4-nitrofluorobenzene (1.0 g, 5.7 mmol) and compound 2-mesylethylamine hydrochloride (1.1 g, 6.8 mmol) till pH was alkaline under an ice bath, the reaction mixture was reacted for 40 min at 0° C. then came to room temperature and reacted overnight. Water was added into the reaction mixture, which was extracted with ethyl acetate, the organic phase was evaporated to dry to deliver 2-chloro-N-(2-(methylsulfonyl)ethyl)-4-nitroaniline (1.4 g, 89% yield) as a yellow solid, which was used for the next step directly.

Reduced iron powder (0.3 g, 5.4 mmol) was added to a solution of compound 2-chloro-N-(2-(methylsulfonyl)ethyl)-4-nitroaniline (1.3 g, 1.1 mmol) in acetic acid (10 mL), stirred and reacted for 2 h at room temperature till the starting material could completely react, evaporated to remove most of the acetic acid, 10% NaOH aqueous solution was added to adjust the pH value to 10, extracted with ethyl acetate (10 mL×3), the organic phase was dried and evaporated to dry to deliver a light yellow solid compound 2-chloro-N$^1$-(2-(methylsulfonyl)ethyl)benzene-1,4-diamine (0.98 g, 84% yield). $^1$H-NMR (d-DMSO, 400 MHz, δ ppm): 6.56-6.61 (m, 2H), 6.47-6.50 (m, 1H), 3.44 (t, J=6.4 Hz, 2H), 3.35 (t, J=6.4 Hz, 2H), 3.04 (s, 3H).

b. Synthesis of (E)-N-(4-(3-chloro-4-((2-(methylsulfonyl)ethyl)amino)phenylamino)-7-(2-ethoxyethoxy)quinazolin-6-yl)-4-(dimethylamino)but-2-enamide (Compound 20)

According to a method similar to the preparation of compound 13, taking 2-chloro-N$^1$-(2-(methylsulfonyl)ethyl)benzene-1,4-diamine as the starting material, compound 20 (39% yield) can be synthesized. $^1$H-NMR (d-DMSO, 400 MHz, δ ppm): 9.57 (s, 2H), 8.83 (s, 1H), 8.44 (s, 1H), 7.79 (d, J=2.4 Hz, 1H), 7.56 (dd, J$_1$=2.4 Hz, J$_2$=8.8 Hz, 1H), 7.28 (s, 1H), 6.79-6.83 (m, 2H), 6.56-6.60 (m, 1H), 5.50 (t, J=6 Hz, 1H), 4.34 (t, J=4.4 Hz, 2H), 3.83 (t, J=4.4 Hz, 2H), 3.30-3.62 (m, 8H), 3.08 (s, 3H), 2.33 (s, 6H), 1.14 (t, J=6.8 Hz, 3H).

Embodiment 21: Synthesis of (E)-N-(4-(3-chloro-4-(2-oxopropoxy)phenylamino)-7-(2-ethoxyethoxy)quinazolin-6-yl)-4-(dimethylamino)but-2-enamide (Compound 21)

Compound 21

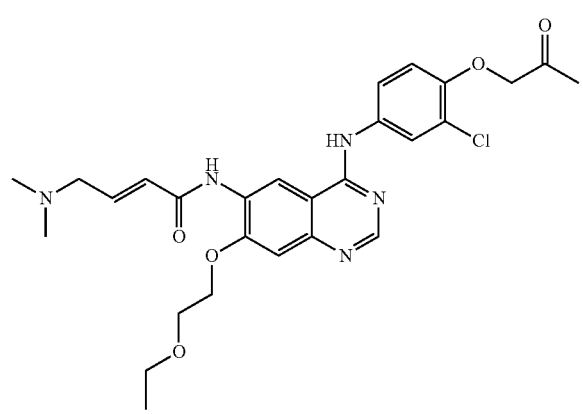

a. Synthesis of 1-(2-chloro-4-aminophenoxy)propan-2-one

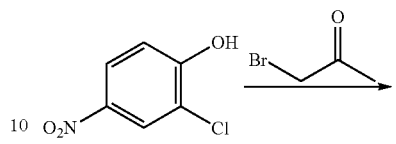

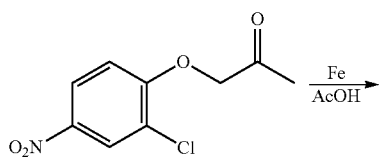

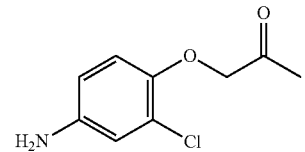

Bromoacetone (4.7 g, 34.6 mmol) was added in DMF (48 mL) and stirred to dissolve, K$_2$CO$_3$ (9.6 g, 69 mmol) was added and stirred for 30 min. 2-Chloro-4-nitrophenol (6 g, 34.6 mmol), KI (0.29 g, 1.7 mmol) were added at 60° C. under an oil bath, stirred for 3 h. The reaction solution was added into ice-water, a large amount of solid was precipitated after stirring, filtrated to deliver product 1-(2-chloro-4-nitrophenoxy)propan-2-one (4.8 g, 60% yield, the purity of hydrogen spectrum was greater than 98%). $^1$H-NMR (d-DMSO, 400 MHz, δ ppm): 8.32 (d, J=2.4 Hz, 1H), 8.16 (dd, J$_1$=2.4 Hz, J$_2$=9.2 Hz, 1H), 7.24 (d, J=9.2 Hz, 1H), 5.19 (s, 2H), 2.20 (s, 3H).

According to a method similar to the preparation of compound 4, taking 1-(2-chloro-4-nitrophenoxy)propan-2-one as the starting material, 1-(2-chloro-4-aminophenoxy)propan-2-one can be synthesized. ESI-MS (m/z): 200.1 [M+H]$^+$.

b. Synthesis of (E)-N-(4-(3-chloro-4-(2-oxopropoxy)phenylamino)-7-(2-ethoxyethoxy)quinazolin-6-yl)-4-(dimethylamino)but-2-enamide (Compound 21)

According to a method similar to the preparation of compound 1, taking 1-(2-chloro-4-aminophenoxy)propan-2-one as the starting material, compound 21 can be synthesized. ESI-MS (m/z): 542.2 [M+H]$^+$.

Embodiment 22: Synthesis of N-(4-(3-chloro-4-fluorophenylamino)-7-(2-ethoxyethoxy)quinazolin-6-yl)acrylamide (Compound 22)

Compound 22

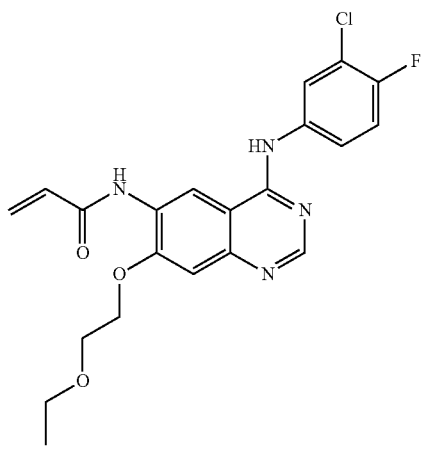

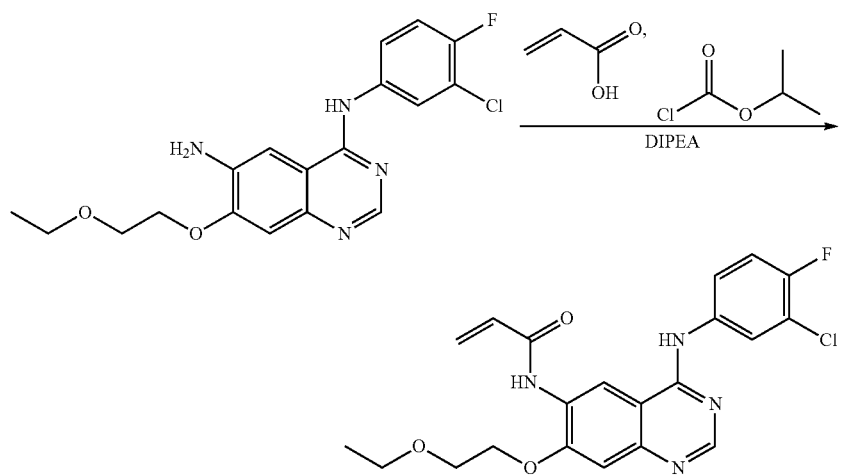

Compound vinyl propionate (2.5 g, 35 mmol), anhydrous THF (50 mL) were added to a 100 mL one-neck flask, DIPEA (1.1 g, 8.5 mmol) was added, isopropyl chloroformate (0.9 g, 7.3 mmol) was dripped slowly under an ice bath, after stirring for 3 h at room temperature, a solution of N-(3-chloro-4-fluorophenyl)-7-(2-ethoxyethoxy)-6-amino-4-quinazolinamine (1.8 g, 4.8 mmol) in pyridine (6 mL) was added. The reaction mixture was stirred for 2 h at 0° C. The reaction mixture was quenched with ice-water, extracted with ethyl acetate, the organic phase was washed with water twice, washed with saturated NaHCO$_3$ aqueous solution, saturated brine, dried, evaporated to dry at room temperature, purified by column chromatography to deliver compound 22 (0.53 g, 23% yield) as a yellow solid. $^1$H-NMR (d-DMSO, 400 MHz, δ ppm): 9.83 (s, 1H), 9.64 (s, 1H), 8.90 (s, 1H), 8.54 (s, 1H), 8.12-8.15 (m, 1H), 7.78-7.82 (m, 1H), 7.43 (t, J=8.8 Hz, 1H), 7.34 (s, 1H), 6.71 (dd, 1H, J$_1$=17.2 Hz, J$_2$=10.4 Hz), 6.32 (dd, 1H, J$_1$=16.8 Hz, J$_2$=1.6 Hz), 5.83 (dd, 1H, J$_1$=10 Hz, J$_2$=1.6 Hz), 4.37 (t, J=4.4 Hz, 2H), 3.83 (t, J=4.4 Hz, 2H), 3.52-3.57 (m, 2H), 1.13 (t, J=7.2 Hz, 3H).

Embodiment 23: Synthesis of N-(4-(3-chloro-4-fluorophenylamino)-7-((2-(dimethylamino)ethyl)(methyl)amino)quinazolin-6-yl)acrylamide (Compound 23)

Compound 23

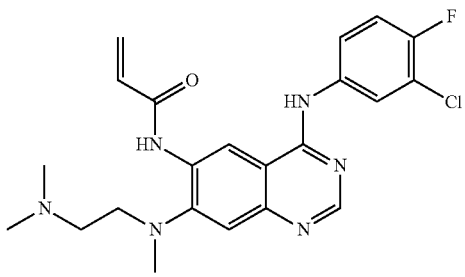

a. Synthesis of N$^4$-(3-chloro-4-fluorophenyl)-N$^7$-(2-(dimethylamino)ethyl)-N$^7$-methyl-6-nitroquinazoline-4,7-diamine

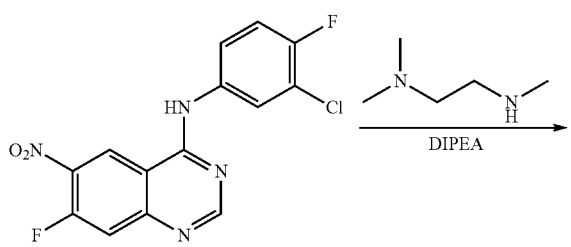

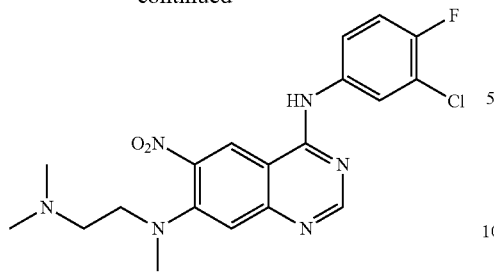

N-(3-chloro-4-fluorophenyl)-7-fluoro-6-nitro-4-quinazolinamine (0.5 g, 1.49 mmol) and N,N,N'-trimethylethanediamine (0.31 g, 3 mmol) were dissolved in anhydrous THF (10 mL), DIPEA (0.58 g, 4.5 mmol) was added, reacted at reflux overnight, evaporated to dry, diluted with water, extracted with ethyl acetate, dried over anhydrous $Na_2SO_4$, purified by column chromatography to deliver compound $N^4$-(3-chloro-4-fluorophenyl)-$N^7$-(2-(dimethylamino)ethyl)-$N^7$-methyl-6-nitroquinazoline-4,7-diamine (0.39 g, 62% yield). ESI-MS (m/z): 419.1 [M+H]$^+$.

b. Synthesis of N-(4-(3-chloro-4-fluorophenylamino)-7-((2-(dimethylamino)ethyl)(methyl)amino)quinazolin-6-yl)acrylamide (Compound 23)

According to a method similar to the preparation for compound 22, taking $N^4$-(3-chloro-4-fluorophenyl)-$N^7$-(2-(dimethylamino)ethyl)-$N^7$-methyl-6-nitroquinazoline-4,7-diamine as the starting material, compound 23 (56% yield) can be synthesized. ESI-MS (m/z): 442.2 [M+H]$^+$.

Embodiment 24: Synthesis of N-(4-(3-chloro-4-fluorophenylamino)-7-(2-ethoxyethoxy)quinazolin-6-yl)ethenesulfonamide (Compound 24)

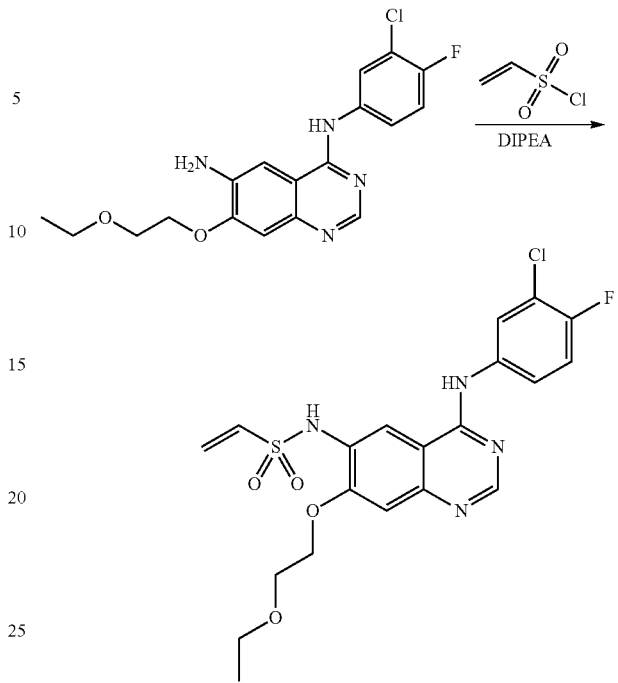

Compound N-(3-chloro-4-fluorophenyl)-7-(2-ethoxyethoxy)-6-amino-4-quinazolineamine (1 g, 2.7 mmol) was dissolved in anhydrous DCM (10 mL), vinyl sulfonyl chloride (673 mg, 5.3 mmol), DIPEA (1.4 mL) was dripped in slowly under an ice bath, after the dripping, the reaction mixture was stirred to react under an ice bath and monitored by TLC, after 0.5 h the reaction finished, evaporated to remove the solvent, purified by column chromatography to deliver compound 24 (200 mg, 17% yield). $^1$H-NMR (d-DMSO, 400 MHz, δ ppm): 9.88 (s, 1H), 9.57 (s, 1H), 8.98 (s, 1H), 8.55 (s, 1H), 8.39 (s, 1H), 8.14-8.16 (m, 1H), 7.79-7.83 (m, 1H), 7.44 (t, J=8.8 Hz, 1H), 7.27 (s, 1H), 6.86-6.95 (m, 1H), 5.85-5.95 (m, 1H), 4.29 (t, J=4.4 Hz, 2H), 3.83 (t, J=4.4 Hz, 2H), 3.54-3.59 (m, 2H), 1.17 (t, J=7.2 Hz, 3H).

Embodiment 25: Synthesis of N-(4-(3-chloro-4-fluorophenylamino)-7-(2-ethoxyethoxy)quinazolin-6-yl)propiolamide (Compound 25)

Compound 24

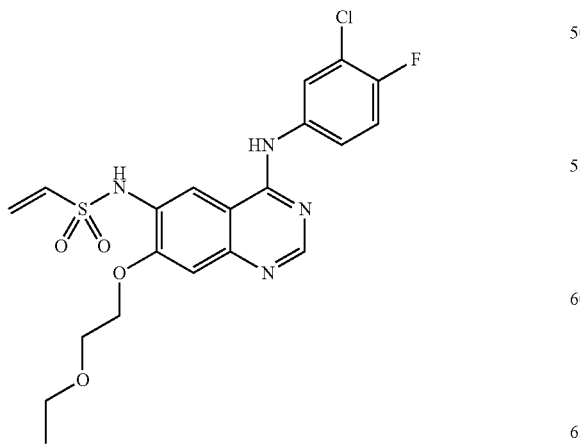

Compound 25

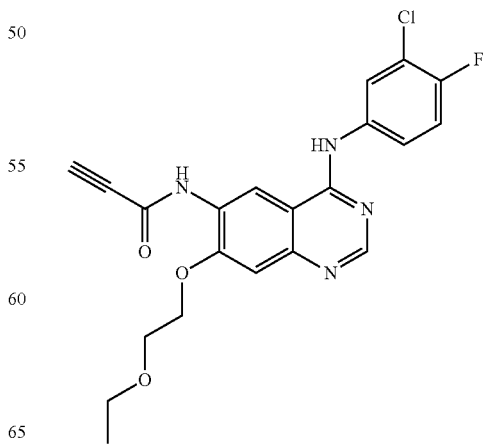

According to a method similar to the preparation of compound 22, taking propargyl acid as the starting material, compound 25 (26% yield) can be synthesized as a yellow solid. ¹H-NMR (d-DMSO, 400 MHz, δ ppm): 10.28 (s, 1H), 9.79 (s, 1H), 8.63 (s, 1H), 8.56 (s, 1H), 8.14-8.16 (m, 1H), 7.79-7.81 (m, 1H), 7.44 (t, J=8.8 Hz, 1H), 7.33 (s, 1H), 4.46 (s, 1H), 4.32 (t, J=4.4 Hz, 2H), 3.82 (t, J=4.4 Hz, 2H), 3.30-3.33 (m, 2H), 1.14 (t, J=7.2 Hz, 3H).

Embodiment 26: Synthesis of N-(4-(3-chloro-4-fluorophenylamino)-7-(2-ethoxyethoxy)quinazolin-6-yl)-2-fluoroacrylamide (Compound 26)

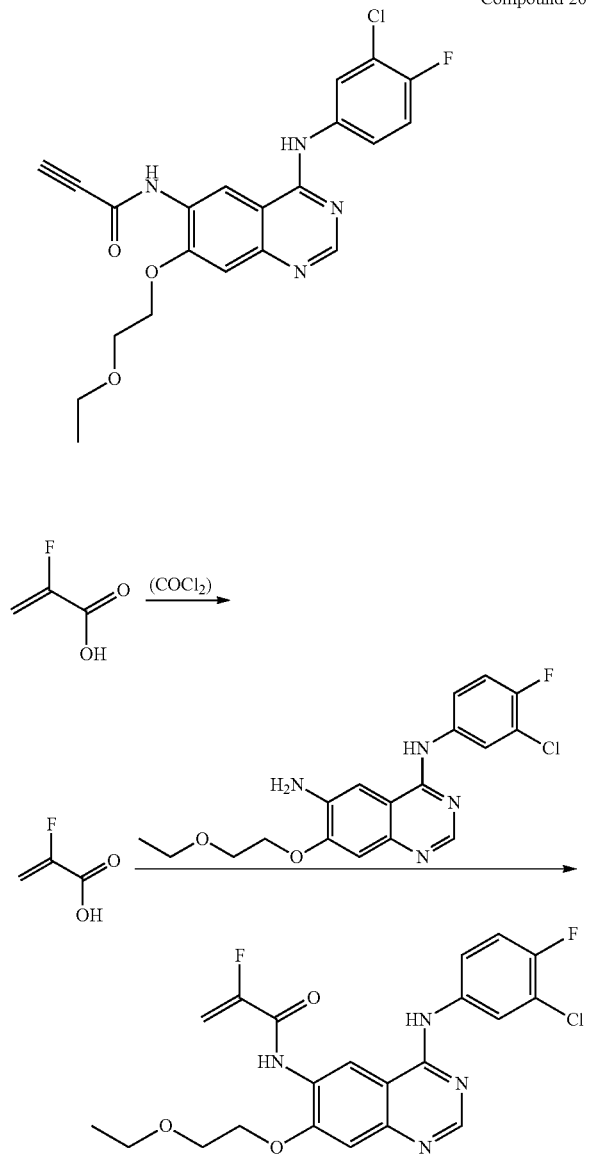

According to a method similar to the preparation of compound 1, taking 2-fluoroacrylic acid as the starting material, compound 26 (30% yield) can be synthesized as a yellow solid. ¹H-NMR (d-DMSO, 400 MHz, δ ppm): 9.88 (s, 1H), 9.57 (s, 1H), 8.98 (s, 1H), 8.92 (s, 1H), 7.98-8.00 (m, 1H), 7.65-7.69 (m, 1H), 7.56 (t, J=8.8 Hz, 1H), 7.43 (s, 1H), 5.75-5.87 (m, 1H), 5.55-5.59 (m, 1H), 4.40 (t, J=4.4 Hz, 2H), 3.83 (t, J=4.4 Hz, 2H), 3.53-3.57 (m, 2H), 1.15 (t, J=7.2 Hz, 3H).

Embodiment 27: Synthesis of N-(4-(3-chloro-4-fluorophenylamino)-7-(2-ethoxyethoxy)quinazolin-6-yl)2-chloroacrylamide (Compound 27)

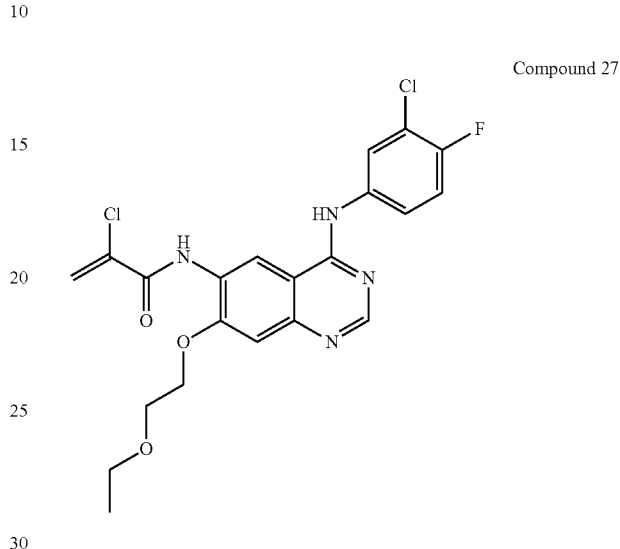

According to a method similar to the preparation of compound 26, taking 2-chloroacrylic acid as the starting material, compound 27 (32% yield) can be synthesized as a yellow solid. ¹H-NMR (d-DMSO, 400 MHz, δ ppm): 9.89 (s, 1H), 9.74 (s, 1H), 8.85 (s, 1H), 8.56 (s, 1H), 8.12-8.15 (m, 1H), 7.78-7.82 (m, 1H), 7.43 (t, J=8.8 Hz, 1H), 7.36 (s, 1H), 6.60 (d, J=2 Hz, 1H), 6.19 (d, J=2 Hz, 1H), 4.36 (t, J=4.4 Hz, 2H), 3.80 (t, J=4.4 Hz, 2H), 3.52-3.56 (m, 2H), 1.15 (t, J=7.2 Hz, 3H).

Embodiment 28: Synthesis of N-(4-(3-chloro-4-fluorophenylamino)-7-(2-ethoxyethoxy)quinazolin-6-yl)2-bromoacrylamide (Compound 28)

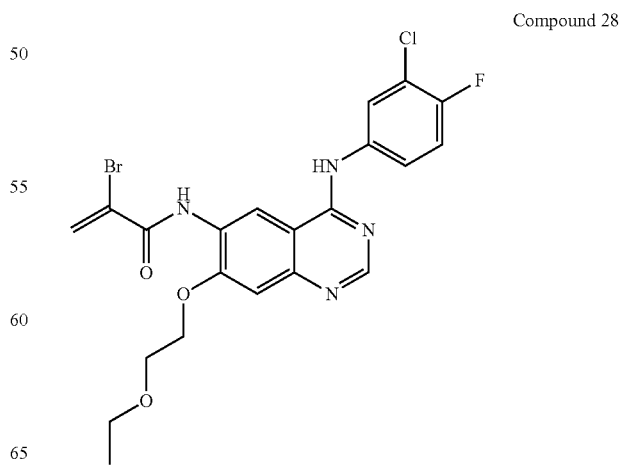

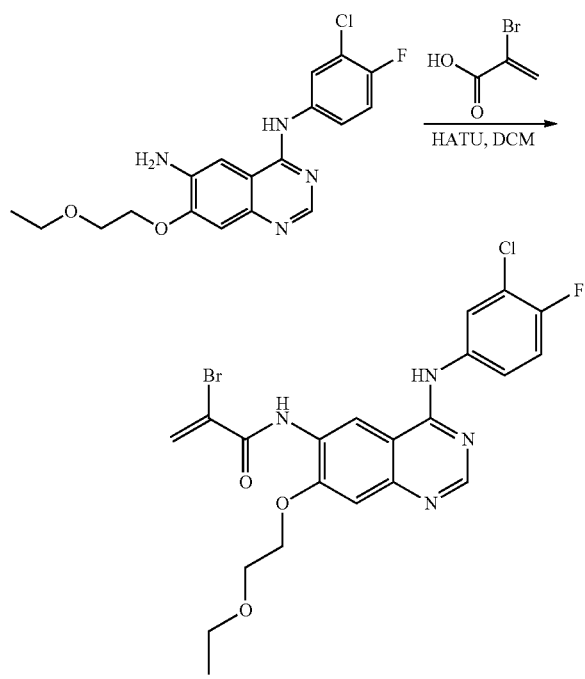

a. Synthesis of (Z)-3-bromoacryloyl chloride

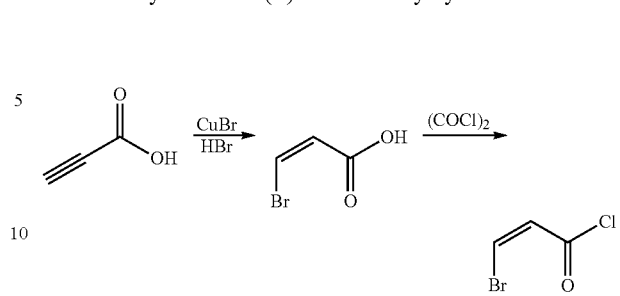

CuBr (0.454 g, 3.2 mmol) was dissolved in 48% hydrobromic acid aqueous solution (9 mL), the solution was cooled to 0° C. under an ice bath, propargyl acid (3.5 g, 50 mmol) was added into the solution dropwise, the reaction mixture was stirred overnight at −10° C., then heated to room temperature. The reaction mixture was extracted with diethyl ether, dried over anhydrous $Na_2SO_4$, filtrated, concentrated, crystallized with diethyl ether to deliver (Z)-3-bromoacrylic acid (6.1 g, 80% yield). $^1$H-NMR (CDCl$_3$, 400 MHz, δ ppm): 9.72 (bs, 1H), 7.19 (d, J=8.4 Hz, 1H), 6.65 (d, J=8.4 Hz, 1H).

(Z)-3-bromoacrylic acid (0.27 g, 1.8 mmol), anhydrous THF (5 mL), and 3 drops of DMF were added into a three-neck flask, oxalyl chloride (0.25 g, 2 mmol) was dripped in under nitrogen gas atmosphere, then reacted for 30 min at room temperature to deliver compound (Z)-3-bromoacryloyl chloride, which was used for the next step directly.

Compound N-(3-chloro-4-fluorophenyl)-7-(2-ethoxyethoxy)-6-amine-4-quinazolinamine (800 mg, 2.1 mmol) was dissolved in 10 mL anhydrous DCM, 2-bromoacrylic acid (385 mg, 2.55 mmol), HATU (970 mg, 2.55 mmol), and 1.1 mL DIPEA were added at room temperature, the reaction mixture was stirred to react at room temperature and monitored by TLC, after 2 h the reaction finished, evaporated to remove the solvent, extracted with ethyl acetate and water (100 mL×3), the organic phase was dried over anhydrous $Na_2SO_4$, evaporated to remove the solvent, purified by column chromatography to deliver the product (352 mg, 33% yield) as a yellow solid. $^1$H-NMR (CD$_3$OD, 400 MHz, δ ppm): 8.96 (s, 1H), 8.49 (s, 1H), 8.01-8.03 (m, 1H), 7.66-7.69 (m, 1H), 7.21-7.27 (m, 2H), 7.10 (d, J=2 Hz, 1H), 6.32 (d, J=2 Hz, 1H), 4.41 (t, J=4.4 Hz, 2H), 3.94 (t, J=4.4 Hz, 2H), 3.63-3.66 (m, 2H), 1.26 (t, J=7.2 Hz, 3H).

b. Synthesis of (Z)—N-(4-(3-chloro-4-fluorophenylamino)-7-(2-ethoxyethoxy)quinazolin-6-yl)-3-bromoacrylamide (Compound 29)

According to a method similar to the preparation of compound 26, taking (Z)-3-bromoacryloyl chloride as the starting material, compound 29 (34% yield) can be synthesized as a yellow solid. ESI-MS (m/z): 509.1 [M+H]$^+$.

Embodiment 29: Synthesis of (Z)—N-(4-(3-chloro-4-fluorophenylamino)-7-(2-ethoxyethoxy)quinazolin-6-yl)-3-bromoacrylamide (Compound 29)

Embodiment 30: Synthesis of (E)-N-(4-(3-chloro-4-fluorophenylamino)-7-(2-ethoxyethoxy)quinazolin-6-yl)-3-bromoacrylamide (Compound 30)

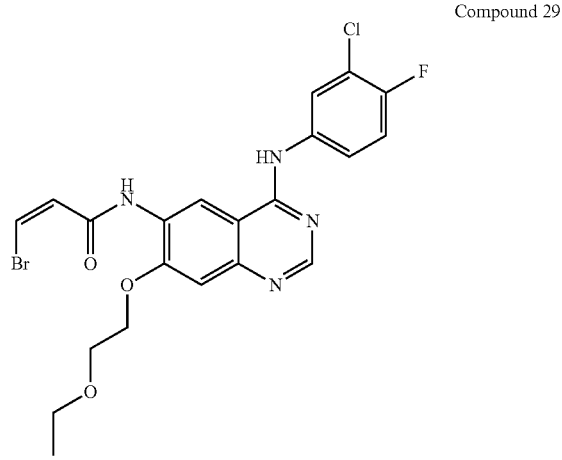

Compound 29

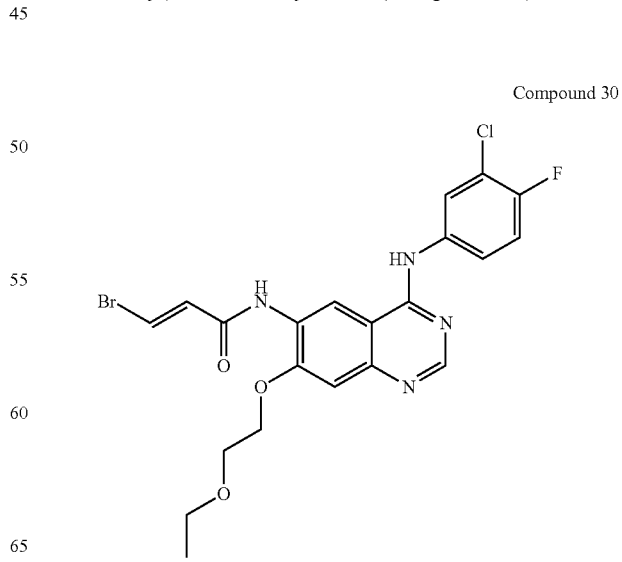

Compound 30 a. Synthesis of (E)-3-bromoacrylic acid

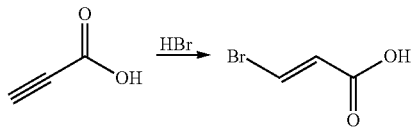

Propargyl acid (1.86 g, 26.5 mmol) was added into 48% hydrobromic acid aqueous solution (10 mL, 88 mmol) dropwise, the reaction mixture was stirred at reflux for 1.5 h, the reaction mixture was cooled with an ice bath, filtrated, dried to deliver (E)-3-bromoacrylic acid (2 g, 50% yield). $^1$H-NMR (CDCl$_3$, 400 MHz, δ ppm): 8.53 (bs, 1H), 7.75 (d, J=13 Hz, 1H), 6.53 (d, J=13 Hz, 1H).

b. Synthesis of (E)-N-(4-(3-chloro-4-fluorophenylamino)-7-(2-ethoxyethoxy)quinazolin-6-yl)-3-bromoacrylamide (Compound 30)

According to a method similar to the preparation of compound 29, taking (E)-3-bromoacrylic acid as the starting material, compound 30 (31% yield) can be synthesized as a yellow solid. $^1$H-NMR (d-DMSO, 400 MHz, δ ppm): 9.84 (s, 1H), 9.74 (s, 1H), 8.88 (s, 1H), 8.54 (s, 1H), 8.13-8.15 (m, 1H), 7.70-7.82 (m, 1H), 7.34-7.47 (m, 2H), 7.24 (s, 1H), 7.01 (d, J=13.6 Hz, 1H), 4.38 (t, J=4.4 Hz, 2H), 3.84 (t, J=4.4 Hz, 2H), 3.54-3.56 (m, 2H), 1.15 (t, J=7.2 Hz, 3H).

Embodiment 31: Synthesis of (E)-N-(4-(3-chloro-4-fluorophenylamino)-7-(2-ethoxyethoxy)quinazolin-6-yl)-3-chloroacrylamide (Compound 31)

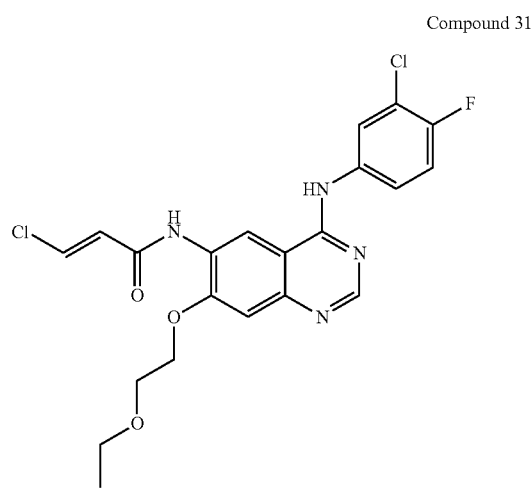 [SMILES: CCOCCOc1cc2ncnc(Nc3ccc(F)c(Cl)c3)c2cc1NC(=O)/C=C/Cl]

Compound 31 a. Synthesis of (E)-3-chloroacrylic acid

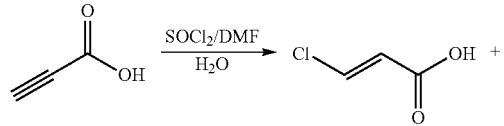

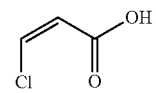

Propargyl acid (140 mg, 2 mmol) was dissolved in anhydrous DMF (1 mL), into which thionyl chloride (286 mg, 2.4 mmol) was added dropwise at a temperature below 30° C. After stirring for 45 min, the reaction mixture was evaporated to remove excessive thionyl chloride, poured into ice-water, extracted with diethyl ether, the organic phase was washed with water, dried over anhydrous Na$_2$SO$_4$, filtrated, concentrated, purified by column chromatography to deliver cis-3-chloroacrylic acid (121 mg, 40% yield) and trans-3-chloroacrylic acid (94 mg, 31% yield). (E)-3-chloroacrylic acid, $^1$H-NMR (CDCl$_3$, 400 MHz, δ ppm): 9.24 (bs, 1H), 7.52 (d, J=13 Hz, 1H), 6.26 (d, J=13 Hz, 1H). (Z)-3-chloroacrylic acid, $^1$H-NMR (CDCl$_3$, 400 MHz, δ ppm): 9.24 (bs, 1H), 7.49 (d, J=8.4 Hz, 1H), 6.23 (d, J=8.4 Hz, 1H).

b. Synthesis of (E)-N-(4-(3-chloro-4-fluorophenylamino)-7-(2-ethoxyethoxy)quinazolin-6-yl)-3-chloroacrylamide (Compound 31)

According to a method similar to the preparation of compound 29, taking (E)-3-chloroacrylic acid as the starting material, compound 31 (30% yield) can be synthesized as a yellow solid. $^1$H-NMR (d-DMSO, 400 MHz, δ ppm): 9.83 (s, 1H), 9.73 (s, 1H), 8.88 (s, 1H), 8.54 (s, 1H), 8.12-8.15 (m, 1H), 7.77-7.81 (m, 1H), 7.40-7.50 (m, 2H), 7.34 (s, 1H), 7.01 (d, J=13.2 Hz, 1H), 4.37 (t, J=4.4 Hz, 2H), 3.84 (t, J=4.4 Hz, 2H), 3.52-3.57 (m, 2H), 1.14 (t, J=7.2 Hz, 3H).

Embodiment 32: Synthesis of (Z)—N-(4-(3-chloro-4-fluorophenylamino)-7-(2-ethoxyethoxy)quinazolin-6-yl)-3-chloroacrylamide (Compound 32)

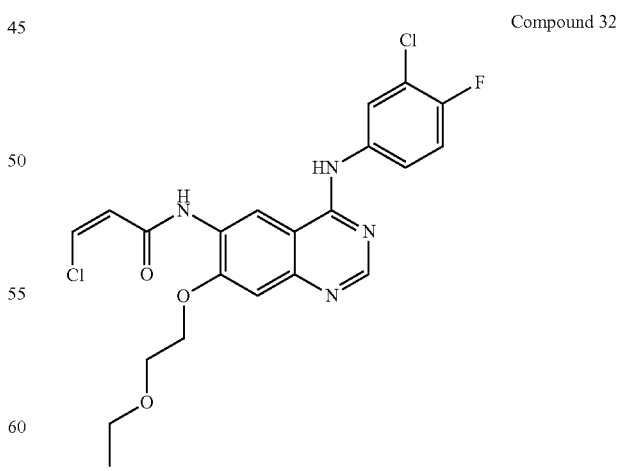

Compound 32

According to a method similar to the preparation of compound 29, taking (Z)-3-chloroacrylic acid as the starting material, compound 32 (32% yield) can be synthesized as a yellow solid. ESI-MS (m/z): 465.1 [M+H]$^+$.

Embodiment 33: Synthesis of (E)-N-(4-(3-chloro-4-fluorophenylamino)-7-(2-ethoxyethoxy)quinazolin-6-yl)-4-(diethylamino)but-2-enamide (Compound 33)

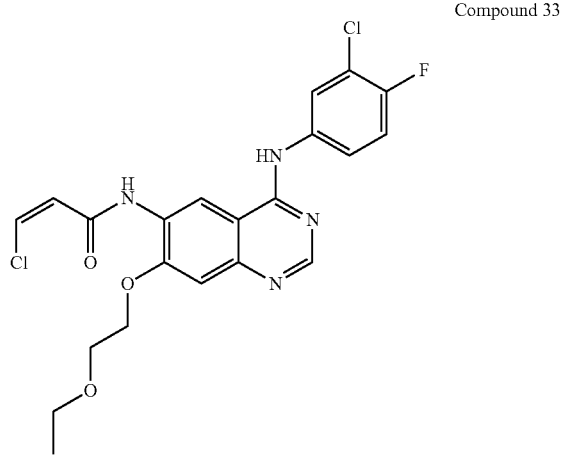 [SMILES: CCOCCOc1cc2ncnc(Nc3ccc(F)c(Cl)c3)c2cc1NC(=O)/C=C\Cl]

Compound 33 a. Synthesis of (E)-4-(diethylamino)but-2-enoyl chloride hydrochloride

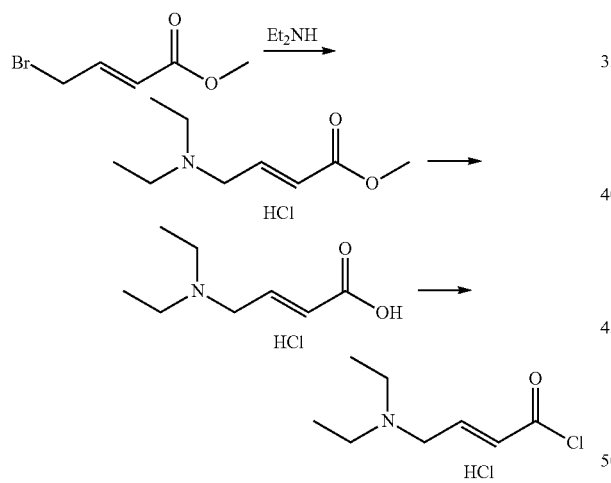

According to a method similar to the preparation of compound 1, taking diethylamine as the starting material, (E)-4-(diethylamino)-2-butenoic acid hydrochloride (80% yield) can be synthesized as a white solid. $^1$H-NMR (D$_2$O, 400 MHz, δ ppm): 6.76-6.84 (m, 1H), 6.22 (d, J=16 Hz, 1H), 3.90 (d, J=8 Hz, 2H), 3.14-3.19 (m, 4H), 1.22 (t, J=8 Hz, 6H).

(E)-4-(Diethylamino)-2-butenoic acid hydrochloride (0.3 g, 1.5 mmol), anhydrous THF (5 mL) and 3 drops of DMF were added into a three-neck flask, oxalyl chloride (0.2 mL, 1.6 mmol) was added dropwise under nitrogen gas atmosphere, then reacted for 30 min at room temperature to deliver compound (E)-4-(diethylamino)but-2-enoyl chloride hydrochloride, which was used for the next step directly.

b. Synthesis of (E)-N-(4-(3-chloro-4-fluorophenylamino)-7-(2-ethoxyethoxy)quinazolin-6-yl)-4-(diethylamino)but-2-enamide (Compound 33)

According to a method similar to the preparation of compound 1, taking 2-ethoxyethanol and diethylamine as the starting materials, compound 33 (58% yield) can be synthesized as a yellow solid. $^1$H-NMR (CD$_3$OD, 400 MHz, δ ppm): 8.98 (s, 1H), 8.51 (s, 1H), 8.01-8.04 (m, 1H), 7.68-7.70 (m, 1H), 7.26-7.28 (m, 2H), 7.02-7.05 (m, 1H), 6.80-6.83 (d, J=16 Hz, 1H), 4.43 (t, J=4.4 Hz, 2H), 4.04-4.06 (d, J=6.8 Hz, 2H), 3.98 (t, J=4.4 Hz, 2H), 3.68-3.73 (m, 2H), 3.26-3.32 (m, 4H), 1.38 (t, J=7.2 Hz, 6H), 1.31 (t, J=6.8 Hz, 3H).

Embodiment 34: Synthesis of (E)-N-(4-(3-chloro-4-fluorophenylamino)-7-(2-ethoxyethoxy)quinazolin-6-yl)-4-(piperidin-1-yl)but-2-enamide (Compound 34)

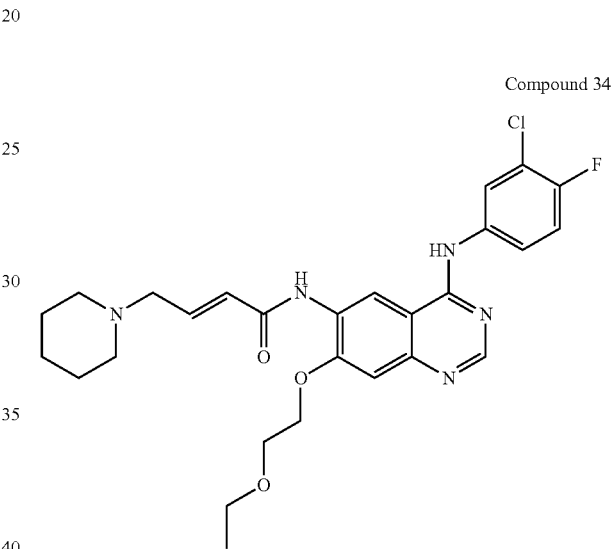

Compound 34 a. Synthesis of (E)-4-(piperidin-1-yl)but-2-enoyl chloride hydrochloride

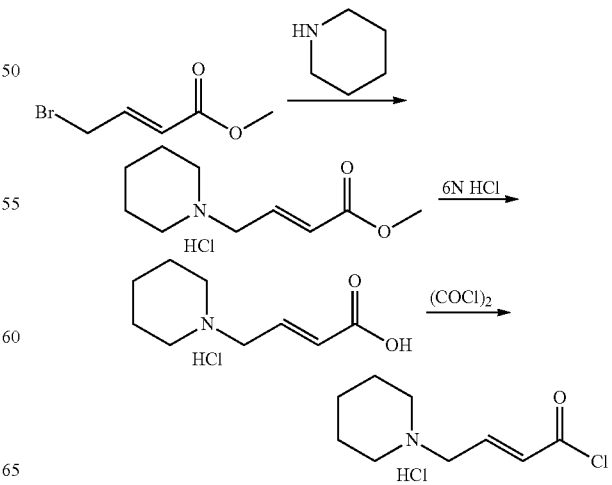

According to a method similar to the preparation of compound 1, taking piperidine as the starting material, (E)-4-(piperidin-1-yl)but-2-enoic acid hydrochloride (46% yield) can be synthesized as a white solid. ¹H-NMR (d-DMSO, 400 MHz, δ ppm): 6.86-6.90 (m, 1H), 6.17 (d, J=16 Hz, 1H), 3.85 (d, J=8 Hz, 2H), 3.31-3.35 (m, 2H), 2.80-2.83 (m, 2H), 1.75-1.79 (m, 4H), 1.67-1.71 (m, 1H), 1.35-1.37 (m, 1H).

(E)-4-(piperidin-1-yl)but-2-enoic acid hydrochloride (0.3 g, 0.0015 mol), anhydrous THF (5 mL) and 3 drops of DMF were added into a three-neck flask, oxalyl chloride (0.2 mL, 0.0016 mmol) was added dropwise under nitrogen gas atmosphere, then reacted for 30 min at room temperature to deliver compound (E)-4-(piperidin-1-yl)but-2-enoyl chloride hydrochloride, which was used for the next step directly.

b. Synthesis of (E)-N-(4-(3-chloro-4-fluorophenylamino)-7-(2-ethoxyethoxy)quinazolin-6-yl)-4-(piperidin-1-yl)but-2-enamide (Compound 34)

According to a method similar to the preparation of compound 1, taking (E)-4-(piperidin-1-yl)but-2-enoyl chloride hydrochloride as the starting material, compound 34 (71% yield) can be synthesized as a yellow solid. ¹H-NMR (CD₃OD, 400 MHz, δ ppm): 8.97 (s, 1H), 8.50 (s, 1H), 8.02-8.05 (m, 1H), 7.68-7.71 (m, 1H), 7.25-7.30 (m, 2H), 7.03-7.07 (m, 1H), 6.60-6.63 (d, J=16 Hz, 1H), 4.42 (t, J=4.4 Hz, 2H), 3.98 (t, J=4.4 Hz, 2H), 3.69-3.71 (m, 2H), 3.53 (d, J=6.4 Hz, 2H), 2.78-2.81 (m, 4H), 1.74-7.77 (m, 4H), 1.59-1.60 (m, 1H), 1.30-1.32 (m, 4H).

Embodiment 35: Synthesis of (E)-N-(4-(3-chloro-4-fluorophenylamino)-7-(2-ethoxyethoxy)quinazolin-6-yl)-4-(pyrrolidin-1-yl)but-2-enamide (Compound 35)

Compound 35

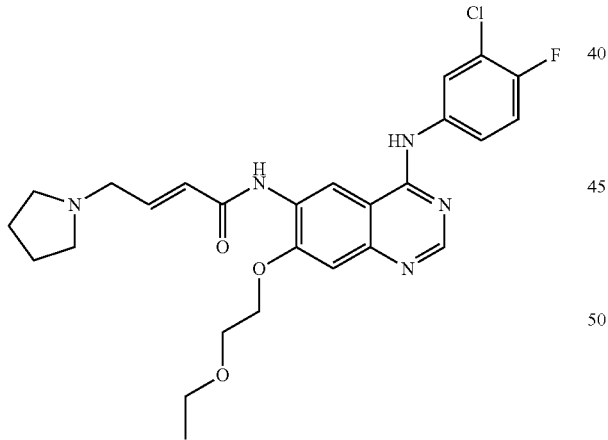

a. Synthesis of (E)-4-(pyrrolidin-1-yl)but-2-enoic acid hydrochloride

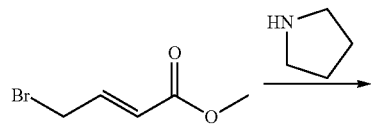

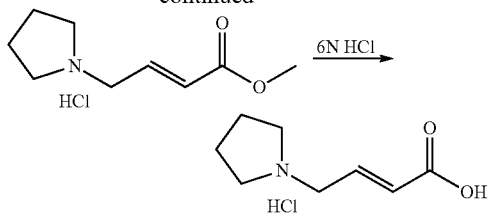

According to a method similar to the preparation of compound 34, (E)-4-(pyrrolidin-1-yl)but-2-enoic acid hydrochloride (38% yield) can be synthesized as a white solid. ¹H-NMR (CD₃OD, 400 MHz, δ ppm): 6.87-6.95 (m, 1H), 6.28 (d, J=16 Hz, 1H), 4.05 (d, J=8 Hz, 2H), 3.64-3.66 (m, 2H), 3.14-3.16 (m, 2H), 2.04-2.19 (m, 4H).

b. Synthesis of (E)-N-(4-(3-chloro-4-fluorophenylamino)-7-(2-ethoxyethoxy)quinazolin-6-yl)-4-(pyrrolidin-1-yl)but-2-enamide (Compound 35)

According to a method similar to the preparation of compound 34, taking (E)-4-(pyrrolidin-1-yl)but-2-enoic acid hydrochloride as the starting material, compound 35 (56% yield) can be synthesized as a yellow solid. ¹H-NMR (CD₃OD, 400 MHz, δ ppm): 8.98 (s, 1H), 8.51 (s, 1H), 8.02-8.04 (m, 1H), 7.68-7.71 (m, 1H), 7.26-7.29 (m, 2H), 7.02-7.06 (m, 1H), 6.75 (d, J=16 Hz, 1H), 4.42-4.44 (m, 2H), 3.71-0.373 (m, 4H), 3.68-3.70 (m, 2H), 3.31-3.34 (m, 4H), 2.08-2.11 (m, 4H), 1.26 (t, J=6.8 Hz, 3H).

Embodiment 36: Synthesis of (E)-N-(4-(3-chloro-4-fluorophenylamino)-7-(2-ethoxyethoxy)quinazolin-6-yl)-4,4,4-trifluorobut-2-enamide (Compound 36)

Compound 36

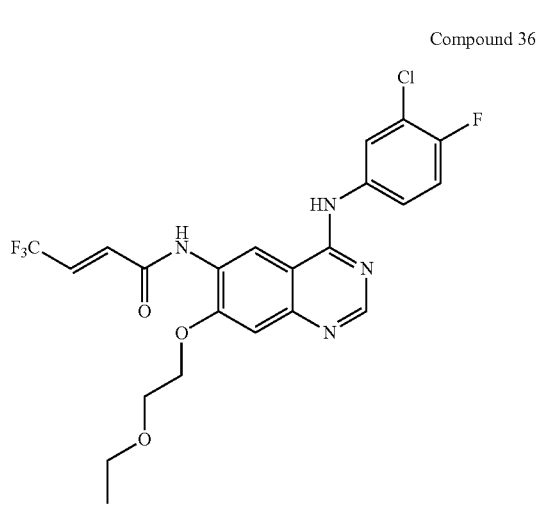 [SMILES: CCOCCOc1cc2ncnc(Nc3ccc(F)c(Cl)c3)c2cc1NC(=O)/C=C/C(F)(F)F]

According to a method similar to the preparation of compound 28, taking 4,4,4-trifluorobutenoic acid as the starting material, compound 36 (56% yield) can be synthesized as a yellow solid. ¹H-NMR (d-DMSO, 400 MHz, δ ppm): 10.12 (s, 1H), 9.87 (s, 1H), 8.93 (s, 1H), 8.55 (s, 1H), 8.12-8.13 (m, 1H), 7.78-7.80 (m, 1H), 7.39-7.45 (m, 2H), 7.36 (s, 1H), 6.97-7.03 (m, 1H), 4.38 (t, J=4.4 Hz, 2H), 3.83 (t, J=4.4 Hz, 2H), 3.53-3.57 (m, 2H), 1.12 (t, J=7.2 Hz, 3H).

Embodiment 37: Synthesis of methyl (E)-4-(4-((3-chloro-4-fluorophenylamino)-7-(2-ethoxyethoxy)quinazolin-6-yl)amino)-4-oxobut-2-enoate (Compound 37)

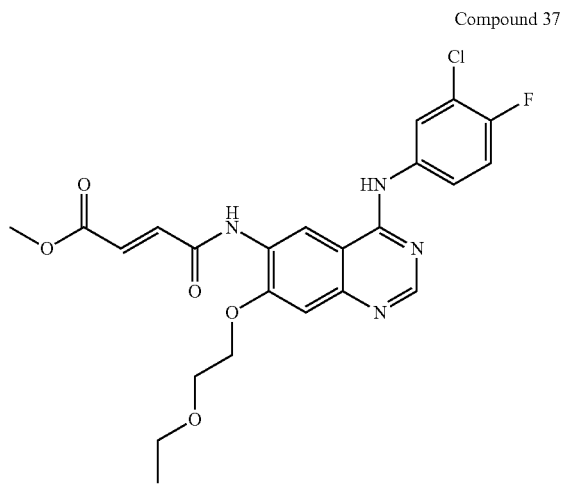 [SMILES: CCOCCOc1cc2ncnc(Nc3ccc(F)c(Cl)c3)c2cc1NC(=O)/C=C/C(=O)OC]

Compound 37

According to a method similar to the preparation of compound 1, taking monomethyl fumarate as the starting material, compound 37 (56% yield) can be synthesized as a yellow solid. $^1$H-NMR (d-DMSO, 400 MHz, δ ppm): 10.12 (s, 1H), 9.86 (s, 1H), 8.96 (s, 1H), 8.55 (s, 1H), 8.12-8.15 (m, 1H), 7.78-7.81 (m, 1H), 7.60 (d, J=15.6, 1H), 7.40-7.45 (m, 1H), 7.35 (s, 1H), 6.79 (d, J=15.6, 1H), 4.38 (t, J=4.4 Hz, 2H), 3.85 (t, J=4.4 Hz, 2H), 3.78 (s, 3H), 3.52-3.57 (m, 2H), 1.13 (t, J=7.2 Hz, 3H).

Embodiment 38: Synthesis of (Z)—N-(4-(3-chloro-4-fluorophenylamino)-7-(2-ethoxyethoxy)quinazolin-6-yl)-3-cyanoacrylamide (Compound 38)

Compound 38

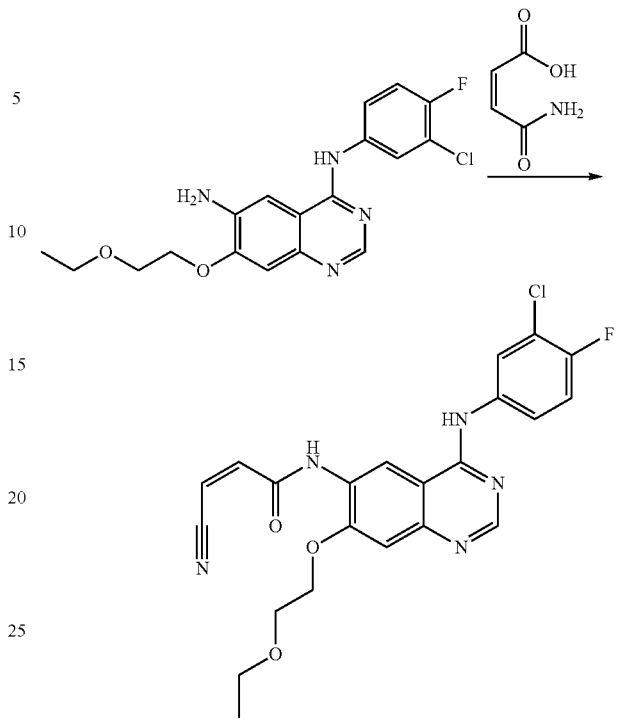

Compound N-(3-chloro-4-fluorophenyl)-7-(2-ethoxy-ethoxy)-6-amino-4-quinazolinamine (800 mg, 2.1 mmol) was dissolved in 10 mL anhydrous DCM, into which aminomaleic acid (294 mg, 2.55 mmol), HATU (970 mg, 2.55 mmol), DIPEA (1.11 mL) were added at room temperature, the reaction mixture was stirred for 2 h at room temperature, evaporated to remove the solvent, extracted with ethyl acetate and water (100 mL×3), the organic phase was dried over anhydrous $Na_2SO_4$, evaporated to remove the solvent, purified by column chromatography to deliver compound 38 (0.54 g, 56% yield) as a yellow solid. $^1$H-NMR (d-DMSO, 400 MHz, δ ppm): 10.1 (s, 1H), 9.95 (s, 1H), 8.93 (s, 1H), 8.54 (s, 1H), 8.09-8.11 (m, 1H), 7.76-7.78 (m, 1H), 7.31-7.44 (m, 3H), 6.42 (d, J=11.2, 1H), 4.37 (t, J=4.4 Hz, 2H), 3.82 (t, J=4.4 Hz, 2H), 3.50-3.53 (m, 2H), 1.11 (t, J=7.2 Hz, 3H). ESI-MS (m/z): 456.1 [M+H]$^+$.

BIOLOGICAL EXAMPLES

The abbreviations described in the following biological examples are as follows: A431: human epithelial carcinoma cell lines; NCI-H1975: human non-small cell lung cancer cell lines; A549: human non-small cell lung cancer; HCC827: human non-small cell lung cancer cell lines; MDA-MB-453: human breast cancer cell lines; PBS: phosphate buffer, PH 7.4; ATP: adenosine triphosphate; TKB: tyrosine kinase reaction buffer; SDS: dodecyl sodium sulfonate; dd$H_2$O: double distilled water; CCK8: 2-(2-methoxy-4-nitrophenyl)-3-(4-nitrophenyl)-5-(2,4-disulfophenyl)-2H-tetrazole monosodium salt; DMEM: Dulbecco,s Modified Eagle's Medium; McCoy's 5A: McCoy's 5A Medium; PRMI-1640: PRMI-1640 Medium; L15: L15 Medium; FBS: fetal bovine serum; HEPEs: hydroxyethyl piperazine ethanesulfonic acid; DMSO: dimethyl sulfoxide;

Biological Embodiment 1

Growth Inhibition Tests of a Series of Compounds in Different Tumor Cells

I. Experimental Materials:
  i. Cell lines: A431 (human epithelial carcinoma cell lines), A549 (human lung cancer cell lines), NCI H1975 (human non-small cell lung cancer cell lines (HCC), HCC 827 (human non-small cell lung cancer cell line), MDA-MB-453 (human breast cancer cell lines)
  ii. CCK8; anti-tumor compounds; DMSO.

II. Reagents and Supplies:
Culture Medium:
  A431 cell lines: 45% DMEM+10% FBS; trypsin (a 0.25% (W/V) solution was prepared with FBS, 0.53 mM EDTA was added);
  A549 cell lines: 45% DMEM+10% FBS; trypsin (a 0.25% (W/V) solution was prepared with FBS, 0.53 mM EDTA was added);
  NCI H1975 cell lines: 45% DMEM+10% FBS; (a 0.25% (W/V) solution was prepared with FBS, 0.53 mM EDTA was added);
  HCC 827 cell line: 90% PRMI-1640+10% FBS; trypsin (a 0.25% (W/V) solution was prepared with FBS, 0.53 mM EDTA was added);
  MDA-MB-453 cell line: 90% L15+10% FBS; trypsin (a 0.25% (W/V) solution was prepared with FBS, 0.53 mM EDTA was added);
  96 holes cell culture plate.

III. Experimental Method:
  i. Cell Culture
  i) Logarithmic growth phase cells were collected and counted, the cells were suspended again with complete medium,
  ii) The cell concentration was adjusted to an appropriate concentration, inoculated to 96 holes, each of which with 100 µL cells suspension.
  iii) The cells were incubated in a 37° C., 100% relative humidity and 5% $CO_2$ incubator, for 24 h.
  ii. Relative Inhibition Rate Test
  i) Logarithmic growth phase cells were collected and counted, the cells were suspended again with complete medium, the cell concentration was adjusted to an appropriate concentration (determined according to the results of cell density optimization test), inoculated to 96 plates, each of which with 100 mL cells suspension. The cells were incubated in a 37° C., 100% relative humidity and 5% $CO_2$ incubator for 24 h.
  ii) The test compounds were diluted to the corresponding concentration stated by culture medium, and the cells were inoculated as 25 µL/hole. The final concentration of the compound was from 10 µM to 0 µM, with a gradient of 4 times, and 10 concentration points totally.
  iii) The cells were incubated in a 37° C., 100% relative humidity, 5% $CO_2$ incubator for 72 h.
  iv) Absorbing the culture medium, the complete medium containing 10% CCK-8 was added and incubated in the incubator of 37° C. for 2-4 h.
  v) After a slight shake, the absorbance at 450 nm was measured by SpectraMax M5 Microplate Reader, taking the absorbance at 650 nm as a reference, the inhibition rate was calculated.

IV. Data Processing and Results
The inhibition rate of drugs on tumor cell growth was calculated by the following formula: the growth inhibition rate of tumor cell %=$[(A_c-A_s)/(A_c-A_b)] \times 100\%$ $A_s$: OA of samples (cell +CCK-8+the test compounds)
$A_c$: OA of negative control (cell +CCK-8+DMSO)
$A_b$: OA of positive control (culture medium +CCK-8+DMSO)

The $IC_{50}$ curve fitting was performed by using the software Graphpad Prism 5 and the calculation formula log (inhibitor) vs. response to calculate the $IC_{50}$ value.

TABLE 1

The results of the activity inhibition tests of the compounds of the present invention in different tumor cell lines

| | Cell lines | | | | |
|---|---|---|---|---|---|
| compound | A431 $IC_{50}$ (nM) | A549 $IC_{50}$ (nM) | NCI-H1975 $IC_{50}$ (nM) | HCC 827 $IC_{50}$ (nM) | MDA-MB-453 $IC_{50}$ (nM) |
| Embodiment 1 | 23.34 | 6076 | 36.09 | 0.2926 | N.D |
| Embodiment 2 | 43.03 | 7561 | 49.92 | 0.2722 | N.D |
| Embodiment 3 | 16.70 | 1956 | 66.50 | 0.3417 | N.D |
| Embodiment 4 | 1.526 | 7521 | 12.20 | 0.3116 | 0.6196 |
| Embodiment 5 | 8.154 | 3137 | 10.63 | 0.555 | N.D |
| Embodiment 6 | 5.865 | 1842 | 41.73 | 0.5499 | N.D |
| Embodiment 10 | 6.009 | 1441 | 45.51 | 0.5871 | 1.428 |
| Embodiment 11 | 79.49 | 2931 | 49.66 | 2.540 | N.D |
| Embodiment 13 | 64.13 | N.D | 106.8 | 2.904 | 2.556 |
| Embodiment 15 | 20.06 | N.D | 7.301 | 3.433 | 1.658 |
| Embodiment 17 | 13.68 | N.D | 6.173 | 0.3426 | 2.526 |
| Embodiment 20 | 6.488 | N.D | 65.6 | 0.538 | 12.7 |
| Embodiment 22 | 6.014 | N.D | 51.81 | 0.153 | 5.672 |
| Embodiment 24 | 3.376 | N.D | 13.72 | 3.952 | 130.5 |
| Embodiment 25 | 11.45 | N.D | 49.31 | 1.467 | 3.427 |
| Embodiment 26 | 54.45 | N.D | 72.49 | 0.538 | 58.2 |
| Embodiment 27 | 368.9 | N.D | 37.11 | 33.22 | 3.716 |
| Embodiment 28 | 572.2 | N.D | 39.44 | 6.397 | 15.05 |
| Embodiment 30 | 296.6 | N.D | 8.216 | 4.867 | 3.997 |
| Embodiment 31 | 289.1 | N.D | 7.435 | 7.817 | 14.87 |
| Embodiment 32 | 24.02 | 4005 | 1.599 | 7.783 | N.D |
| Embodiment 33 | 5.455 | 3527 | 190.4 | 1.310 | N.D |
| Embodiment 36 | 148.2 | N.D | 27.56 | 0.153 | 18.3 |
| Embodiment 37 | 207.4 | N.D | 35.23 | 0.987 | 21.57 |
| Embodiment 38 | 94.82 | N.D | 18.37 | 5.563 | 0.6805 |
| Afatinib | 10.21 | 6781 | 96.07 | 0.4376 | N.D |

Biological Embodiment 2

The following experiments can be used to determine the inhibitory effects of the compounds of the present invention on the activity of EGFR tyrosine kinase and Her-2 enzyme.

The kinase analysis in vitro was performed using the HTRF kinEASE TK kit of Invitrogen Co., the procedure steps were carried out according to instructions of kit, the method then was used to detect the inhibitory effects of test compounds on substrate peptide phosphorylation of the EGFR receptor tyrosine kinase and Her-2 activity enzyme in vitro. Specific steps are as follows:

a) Firstly 2.5% DMSO solutions were prepared using the configured 1× kinase buffer (the high concentration of DMSO will affect the reaction, the final concentration of DMSO was controlled to be 1%), then the test compounds tested were diluted with 2.5% DMSO solutions corresponding to enzymes, while testing on EGFR, the screening concentrations of the compounds were started from 5000 nM with 4 fold gradient dilution, 10 of concentrations, while testing on Her-2, the screening concentrations of compounds were started from 10000 nM with 4 fold gradient dilution, 10 of concentrations. Besides the control hole, all the reaction holes were added with 4 microliters of the diluted solution of the test compounds, the control hole was added with 4 microliters of the 2.5% DMSO solution prepared previously corresponding to EGFR and Her-2 enzyme.

b) 2 microliters of the previously prepared TK-biotin substrate solution of EGFR and Her-2 enzyme corresponding to the substrate concentration were added to all the reaction holes.

c) 2 microliters of previously prepared enzyme solutions with corresponding concentrations were added to all the reaction holes except the negative hole, the volume of the negative hole was complemented with 2 microliters of enzyme corresponding to 1× kinase buffer. The holes were sealed with sealing film for microplate, mixed and incubated at room temperature for 10 min to allow the compounds and enzymes fully combine.

d) 2 microliters of ATP solutions with concentration corresponding to EGFR and Her-2 enzyme were added to all the reaction holes to start the kinase reaction, the enzyme reaction time of EGFR and HER2 are 30 min.

e) The EGFR and Her-25 detection solution were prepared 5 min before the end of the kinase reaction. Streptavidin-XL665 and TK europium cryptate (1:100) detection solution corresponding to the two enzymes were prepared respectively by using detection buffer in the kit.

f) 5 microliters of diluted Streptavidin-XL665 were added to all the reaction holes after the kinase reaction was over, diluted TK antibody europium cryptate detection solutions were then added immediately after fully mixed.

g) The holes was sealed and mixed, reacted for 1 h at room temperature, then the ENVISION (Perkinelmer) instrument was used to detect the fluorescence signal (320 nm stimulation, 665 nm, 615 nm emission). The inhibition rate of each hole is calculated by the full active hole and the background signal hole, replicates holes were averaged, meanwhile the half inhibitory activity ($IC_{50}$) of each test compound were fitted by using a professional drawing analysis software PRISM 5.

TABLE 2

The $IC_{50}$ inhibitory activity test of the compounds against EGFR and Her-2 enzymes

| Compound ID | $IC_{50}$ against EGFR (nM) | $IC_{50}$ against Her-2 (nM) |
|---|---|---|
| Embodiment 1 | 0.7652 | 39.26 |
| Embodiment 2 | 0.9496 | 148.3 |
| Embodiment 3 | 2.733 | 482.1 |
| Embodiment 4 | 0.699 | 42.11 |
| Embodiment 5 | 2.848 | 131.6 |
| Embodiment 6 | 1.545 | 83.84 |
| Embodiment 10 | 0.7715 | 3.634 |
| Embodiment 11 | 153.5 | 261.8 |
| Embodiment 12 | 10.18 | 53.91 |

TABLE 2-continued

The $IC_{50}$ inhibitory activity test of the compounds against EGFR and Her-2 enzymes

| Compound ID | $IC_{50}$ against EGFR (nM) | $IC_{50}$ against Her-2 (nM) |
|---|---|---|
| Embodiment 33 | 1.488 | 10.94 |
| Afatinib | 0.9647 | 73.72 |

Biological Embodiment 3 In Vivo Pharmacodynamics Evaluation

BALB/c nude mice, female, 6 to 7 weeks of age, weight 20 g±2 g, purchased from Shanghai silaike experimental animal Co. Ltd., SPF environment.

The logarithmic growth phase NCI-H1975 cells cultured in vitro were digested with trypsin, washed with PBS for three times, the cell survival rate was detected by trypan blue exclusion to be >90%, the cell concentration was adjusted to $1×10^7$/mL with PBS, which was implanted subcutaneously in back forelimb of the nude mice with 0.2 mL/pcs under aseptic condition. After tumor formation, the tumor were cultured for two passages in vivo, the tumor were stripped out to sterile culture plate when growing to the volume of 300 to 500 mm$^3$, a small amount of PBS was added, the tumor tissue with vigorous growth were cut into about 1.5 mm$^3$ tumor blocks, inoculated in right armpit of the nude mice. The diameter of tumor was measured with vernier caliper, when the tumor grew to 100 to 200 mm$^3$, then the animal were randomly grouping, the drug dosage of compound 2, 5, 9 11, 12, 13 and the positive control was 20 mg/kg, gavage administration, once a day or every other day, continuously administrated for 14 days (d14) and observed for 7 days (d22), the negative control group was administrated with the same amount of solvent (saline solution of 1% DMSO), during the period of administration and recovery, the body weight and tumor size of the nude mice were measured weekly 2 to 3 times. The tumor volume and relative tumor volume were calculated according to the measured data, and the calculation formula of the tumor volume (TV) was TV=1/2×a×b$^2$, of which a and b represent the tumor length and diameter respectively. The relative tumor volume (RTV) was calculated according to the measured results, and the calculation formula was: RTV=$V_t$/$V_0$, wherein $V_0$ represents the tumor volume at the beginning of the experiment, $V_t$ represents the volume of the tumor each measured. The evaluation index of anti-tumor activity was relative tumor growth rate (T/C %), the calculation formula was as follows: T/C (%)=$T_{RTV}$/$C_{RTV}$×100%, $T_{RTV}$ represents the RTV of the treatment group; $C_{RTV}$ represents the RTV of the negative control group; the relative tumor growth inhibition rate (tumor inhibition rate)=(1−T/C)×100%, the results were shown in Table 3.

TABLE 3

Therapeutic effect of the compounds of the present invention on NCI-H1975 nude mice transplanted tumor

| Group | Animal No. (pcs) | Administration mode | Dosage (mg/kg) | RTV | Inhibition rate (%) d22 | T/C (%) |
|---|---|---|---|---|---|---|
| Blank control | 8 | qd | 0 | 7.45 ± 1.26 | — | — |
| Positive control | 8 | qd | 20 | 1.67 ± 0.20 | 67.6** | 22.44 |
| Embodiment 4 | 8 | qod | 80 | 0.43 ± 0.05 | 95.1*** | 5.75 |
| Embodiment 4 | 8 | qod | 20 | 1.39 ± 0.40 | 82.0** | 18.71 |
| Embodiment 4 | 8 | qod | 5 | 2.00 ± 0.29 | 73.2** | 26.91 |
| Embodiment 12 | 8 | qod | 80 | 0.70 ± 0.09 | 90.5*** | 9.34 |

TABLE 3-continued

Therapeutic effect of the compounds of the present invention on NCI-H1975 nude mice transplanted tumor

| Group | Animal No. (pcs) | Administration mode | Dosage (mg/kg) | RTV | Inhibition rate (%) d22 | T/C (%) |
|---|---|---|---|---|---|---|
| Embodiment 12 | 8 | qod | 20 | 1.59 ± 0.33 | 78.7** | 21.41 |
| Embodiment 12 | 8 | qd | 5 | 2.47 ± 0.68 | 66.1** | 33.21 |

Note:
(1) compared with the positive control group, *p < 0.05, p < 0.01, *p < 0.001.
(2) qd: administrated every day; qod: administrated every other day; d22: the time of observed for 7 days after the last administration.
(3) the positive control drug: Afatinib (N-[4-[(3-chloro-4- fluorophenyl)amino]-7-[[(3S)-tetrahydro-3-furyl]oxy]-6-quinazolinyl)-4- (dimethylamino)-but-2-enamide).
(4) the results show that, compound 2 with high, middle and low dosages all have good tumor inhibition effect, observed for 7 days after administration for 14 days, the tumor inhibition rate of which achieved to 95.1%, 82.0%, 73.2% respectively, the tumor inhibition rate of compound 12 with high, middle dosages were 90.5%, 78.7%, all of which were higher than the positive control with 67.6%. The above experimental results in vivo show that the compounds of the present invention have a better tumor inhibition effect on NCI-H1975 constructed tumors.

Although the foregoing text described embodiments of the present invention, it should be understood that those are intended to be purely illustrative, and variation and improvement on the embodiments of the present invention can be made without departing from the spirit and scope of the present invention. Therefore, the protection scope of the present invention is limited by the attached claims.

What is claimed is:

1. A compound represented by general formula I, a stereoisomer thereof and a pharmaceutical acceptable salt or a solvate thereof,

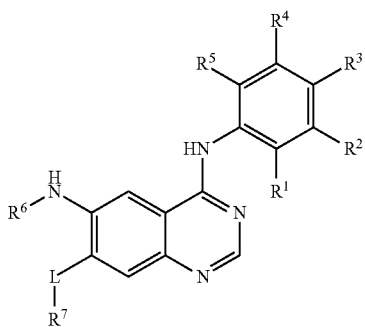

I wherein each of $R^1$, $R^2$, $R^3$, $R^4$ and $R^5$ independently represents a hydrogen, a halogen, a substituted or unsubstituted $C_1$-$C_6$ alkoxy, a $C_2$-$C_6$ alkynyl, a "substituted or unsubstituted $C_1$-$C_6$ alkylamino", the "substituted" in the "substituted or unsubstituted $C_1$-$C_6$ alkoxy" or the "substituted or unsubstituted $C_1$-$C_6$ alkylamino" is being substituted by one or more substituents which may be the same or different, each substituent being independently selected from the group consisting of a halogen, a substituted or unsubstituted $C_5$-$C_{10}$ aryl, a "$C_2$-$C_{10}$ heteroaryl containing 1 to 3 of heteroatoms, and in which the heteroatom is an oxygen, a sulfur or a nitrogen", a $C_1$-$C_6$ alkyloxy,

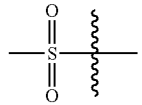 [SMILES: *S(C)(=O)=O]

and a $C_1$-$C_6$ carbonyl; the "substituted" in the "substituted or unsubstituted $C_5$-$C_{10}$ aryl" is being substituted by one or more substituents which may be the same or different, each substituent being independently selected from the group consisting of a fluorine, a chlorine, and a bromine;

$R^6$ represents

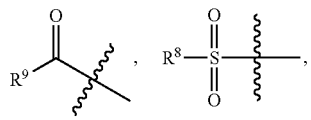

each of $R^8$ and $R^9$ independently represents a "substituted or unsubstituted $C_2$-$C_6$ alkenyl" or a "substituted or unsubstituted $C_2$-$C_6$ alkynyl", the "substituted" in the "substituted or unsubstituted $C_2$-$C_6$ alkenyl" or the "substituted or unsubstituted $C_2$-$C_6$ alkynyl" is being substituted by one or more substituents which may be the same or different, each substituent being independently selected from the group consisting of a halogen, a cyano, a substituted or unsubstituted $C_1$-$C_6$ alkyl and a ester group; the "substituted" in the "substituted or unsubstituted $C_1$-$C_6$ alkyl" is being substituted by one or more substituents which may be the same or different, each substituent being independently selected from the group consisting of an amino, a halogen, a $C_1$-$C_6$ alkylamino and a $C_2$-$C_6$ cycloalkylamino;

L represent a covalent bond, O, S or

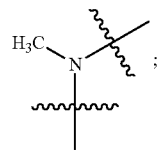

$R^7$ represents

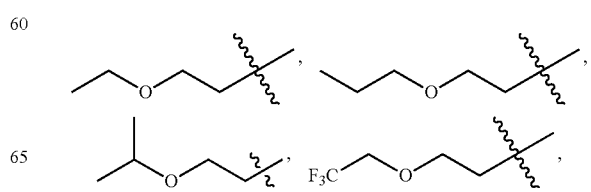

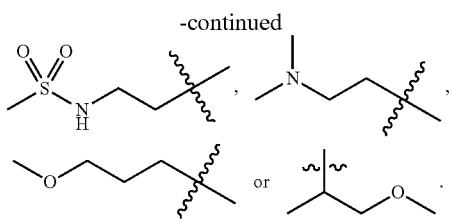

2. The compound represented by general formula I, the stereoisomer thereof and the pharmaceutical acceptable salt or the solvate thereof according to claim 1, wherein,
when the "substituted" in the "substituted or unsubstituted $C_1$-$C_6$ alkoxy" or the "substituted or unsubstituted $C_1$-$C_6$ alkylamino" in $R^1$, $R^2$, $R^3$, $R^4$ or $R^5$ is being substituted by the halogen, the "halogen" is a fluorine, a chlorine, a bromine or an iodine;
when the "substituted" in the "substituted or unsubstituted $C_1$-$C_6$ alkoxy" or the "substituted or unsubstituted $C_1$-$C_6$ alkylamino" in $R^1$, $R^2$, $R^3$, $R^4$ or $R^5$ is being substituted by the "substituted or unsubstituted $C_5$-$C_{10}$ aryl", the "substituted $C_5$-$C_{10}$ aryl" is a "substituted or unsubstituted phenyl";
when the "substituted" in the "substituted or unsubstituted $C_1$-$C_6$ alkoxy" or the "substituted or unsubstituted $C_1$-$C_6$ alkylamino" in $R^1$, $R^2$, $R^3$, $R^4$ or $R^5$ is being substituted by the "$C_2$-$C_{10}$ heteroaryl containing 1 to 3 of heteroatoms, and in which the heteroatom is an oxygen, a sulfur or a nitrogen", the "$C_2$-$C_{10}$ heteroaryl containing 1 to 3 of heteroatoms, and in which the heteroatom is an oxygen, a sulfur or a nitrogen" is a "$C_4$-$C_6$ heteroaryl containing 1 to 2 of heteroatoms, and in which the heteroatom is a nitrogen";
when the "substituted" in the "substituted or unsubstituted $C_1$-$C_6$ alkoxy" or the "substituted or unsubstituted $C_1$-$C_6$ alkylamino" in $R^1$, $R^2$, $R^3$, $R^4$ or $R^5$ is being substituted by the "$C_1$-$C_6$ alkyloxy", the "$C_1$-$C_6$ alkyloxy" is a methoxy, an ethoxy, a propoxy, an iso-propoxy, or a tert-butoxy;
when the "substituted" in the "substituted or unsubstituted $C_1$-$C_6$ alkoxy" or the "substituted or unsubstituted $C_1$-$C_6$ alkylamino" in $R^1$, $R^2$, $R^3$, $R^4$ or $R^5$ is being substituted by the "$C_1$-$C_6$ carbonyl", the "$C_1$-$C_6$ carbonyl" is

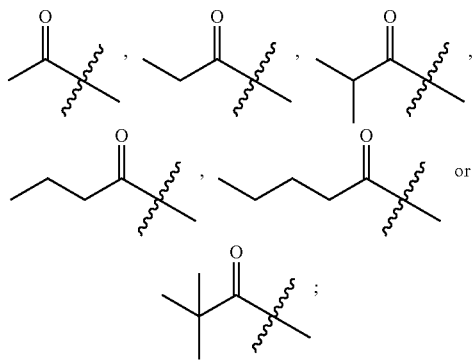

when the "substituted" in the "substituted or unsubstituted $C_2$-$C_6$ alkenyl" or the "substituted or unsubstituted $C_2$-$C_6$ alkynyl" in $R^8$ or $R^9$ is being substituted by the halogen, the halogen is a fluorine, a chlorine, a bromine or an iodine;

when the "substituted" in the "substituted or unsubstituted $C_2$-$C_6$ alkenyl" or the "substituted or unsubstituted $C_2$-$C_6$ alkynyl" in $R^8$ or $R^9$ is being substituted by the "substituted or unsubstituted $C_1$-$C_6$ alkyl", the "substituted" in the "substituted or unsubstituted $C_1$-$C_6$ alkyl" is being substituted by a halogen, the halogen is a fluorine, a chlorine, a bromine or an iodine.

3. The compound represented by general formula I, the stereoisomer thereof and the pharmaceutical acceptable salt or the solvate thereof according to claim 1, wherein,
when the "substituted" in the "substituted or unsubstituted $C_1$-$C_6$ alkoxy" or the "substituted or unsubstituted $C_1$-$C_6$ alkylamino" in $R^1$, $R^2$, $R^3$, $R^4$ or $R^5$ is being substituted by the halogen, the halogen is fluorine or chlorine;
when the "substituted" in the "substituted or unsubstituted $C_1$-$C_6$ alkoxy" or the "substituted or unsubstituted $C_1$-$C_6$ alkylamino" in $R^1$, $R^2$, $R^3$, $R^4$ or $R^5$ is being substituted by the "substituted or unsubstituted phenyl", the "substituted or unsubstituted phenyl" is 2-fluorophenyl;
when the "substituted" in the "substituted or unsubstituted $C_1$-$C_6$ alkoxy" or the "substituted or unsubstituted $C_1$-$C_6$ alkylamino" in $R^1$, $R^2$, $R^3$, $R^4$ or $R^5$ is being substituted by the "$C_4$-$C_6$ heteroaryl containing 1 to 2 of heteroatoms, and in which the heteroatom is a nitrogen", the "$C_4$-$C_6$ heteroaryl containing 1 to 2 of heteroatoms, and in which the heteroatom is a nitrogen" is pyridyl;
when the "substituted" in the "substituted or unsubstituted $C_2$-$C_6$ alkenyl" or the "substituted or unsubstituted $C_2$-$C_6$ alkynyl" in $R^8$ or $R^9$ is being substituted by the halogen, the halogen is fluorine, chlorine or bromine;
when the "substituted" in the "substituted or unsubstituted $C_2$-$C_6$ alkenyl" or the "substituted or unsubstituted $C_2$-$C_6$ alkynyl" in $R^8$ or $R^9$ is being substituted by the "substituted or unsubstituted $C_1$-$C_6$ alkyl", the "substituted or unsubstituted $C_1$-$C_6$ alkyl" is trifluoromethyl or aminomethyl.

4. The compound represented by general formula I, the stereoisomer thereof and the pharmaceutical acceptable salt or the solvate thereof according to claim 1, wherein,
when each of $R^1$, $R^2$, $R^3$, $R^4$ and $R^5$ independently represents the halogen, the "halogen" is a fluorine, a chlorine, a bromine or an iodine;
when each of $R^1$, $R^2$, $R^3$, $R^4$ and $R^5$ independently represents the "substituted or unsubstituted $C_1$-$C_6$ alkoxy", the "substituted or unsubstituted $C_1$-$C_6$ alkoxy" is a "substituted or unsubstituted methoxy", a "substituted or unsubstituted ethoxy", a "substituted or unsubstituted propoxy", a "substituted or unsubstituted iso-propoxy", a "substituted or unsubstituted butoxy", a "substituted or unsubstituted iso-butoxy", a "substituted or unsubstituted tert-butoxy";
when each of $R^1$, $R^2$, $R^3$, $R^4$ and $R^5$ independently represents the $C_2$-$C_6$ alkynyl, the "$C_2$-$C_6$ alkynyl" is

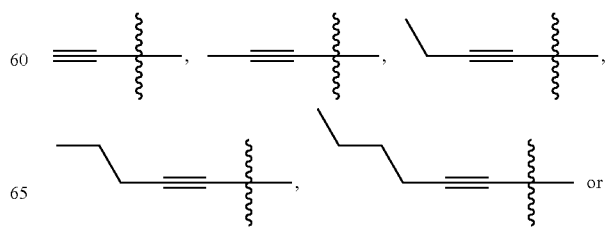

-continued

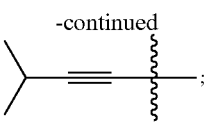

when each of $R^1$, $R^2$, $R^3$, $R^4$ and $R^5$ independently represents the "substituted or unsubstituted $C_1$-$C_6$ alkylamino", the "substituted or unsubstituted $C_1$-$C_6$ alkylamino" is a "substituted or unsubstituted methylamino", a "substituted or unsubstituted ethylamino", a "substituted or unsubstituted propylamino", a "substituted or unsubstituted iso-propylamino", a "substituted or unsubstituted butylamino", a "substituted or unsubstituted iso-butylamino", a "substituted or unsubstituted tert-butylamino";

when $R^6$ represents

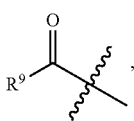

the

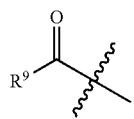

is

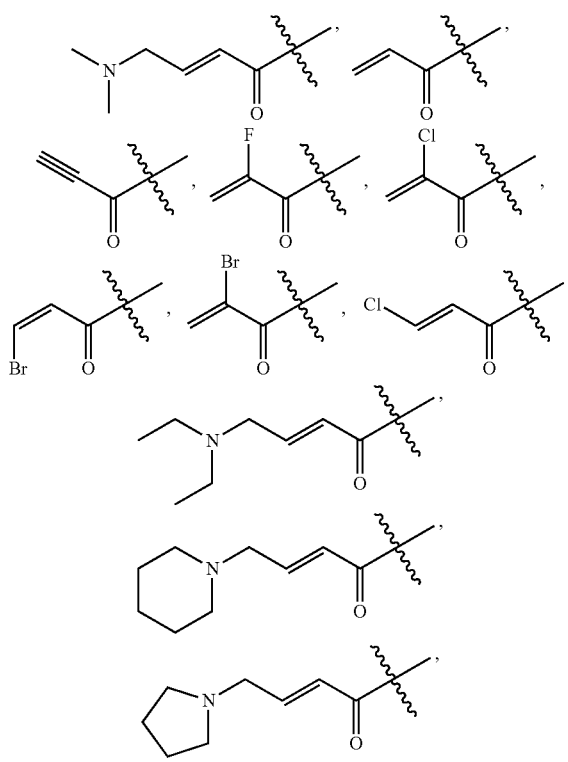

-continued

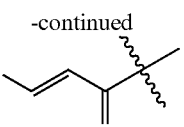

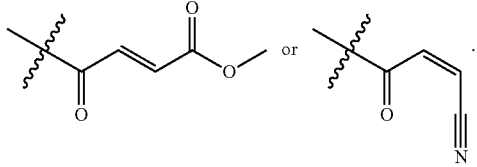

5. The compound represented by general formula I, the stereoisomer thereof and the pharmaceutical acceptable salt or the solvate thereof according to claim 4, wherein,
when each of $R^1$, $R^2$, $R^3$, $R^4$ and $R^5$ independently represents the halogen, the "halogen" is fluorine or chlorine;
when each of $R^1$, $R^2$, $R^3$, $R^4$ and $R^5$ independently represents the "substituted methoxy", the "substituted methoxy" is

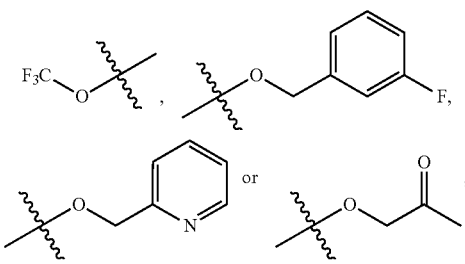

when each of $R^1$, $R^2$, $R^3$, $R^4$ and $R^5$ independently represents the "substituted ethoxy", the "substituted ethoxy" is

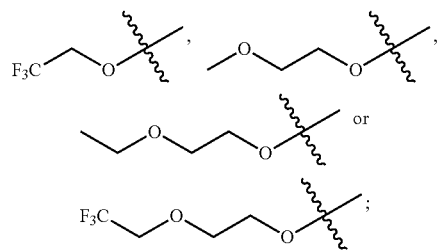

when each of $R^1$, $R^2$, $R^3$, $R^4$ and $R^5$ independently represents the "substituted ethylamino", the "substituted ethylamino" is

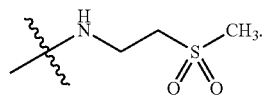 [SMILES: *NCCS(C)(=O)=O]

6. The compound represented by general formula I, the stereoisomer thereof and the pharmaceutical acceptable salt or the solvate thereof according to claim 1, wherein,
in the compound represented by general formula I, $R^1$ represents hydrogen; $R^2$ represents hydrogen, fluorine, chlorine or $C_2$-$C_6$ alkynyl; $R^3$ represents hydrogen, fluorine, chlorine,

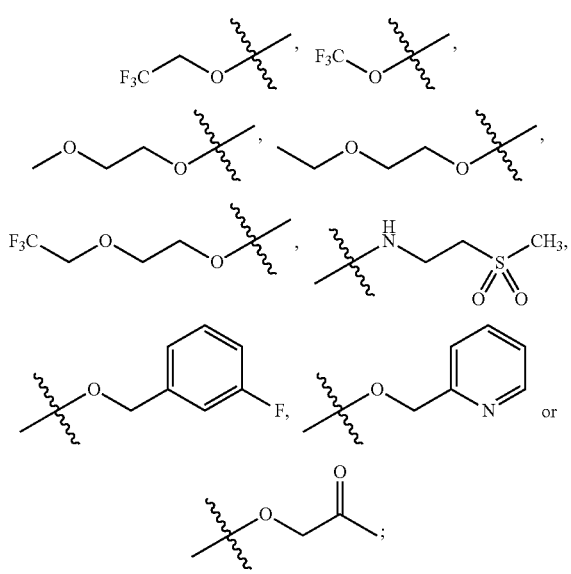
R⁴ represents hydrogen, fluorine or chlorine;
R⁵ represents hydrogen;
R⁶ represents
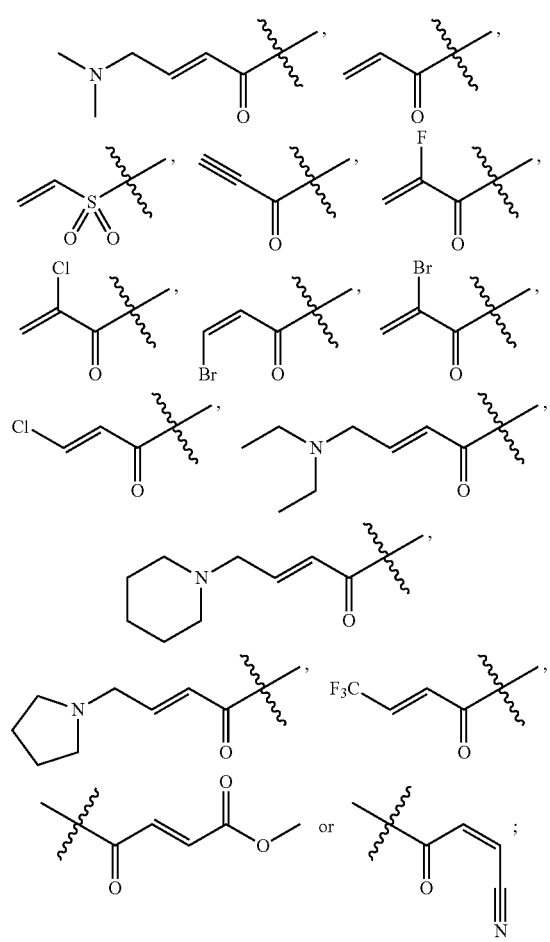
L represents O, S or
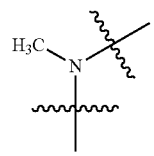
7. The compound represented by general formula I, the stereoisomer thereof and the pharmaceutical acceptable salt or the solvate thereof according to claim 6, wherein,
 the compound represented by general formula I is selected from the group consisting of
I-1
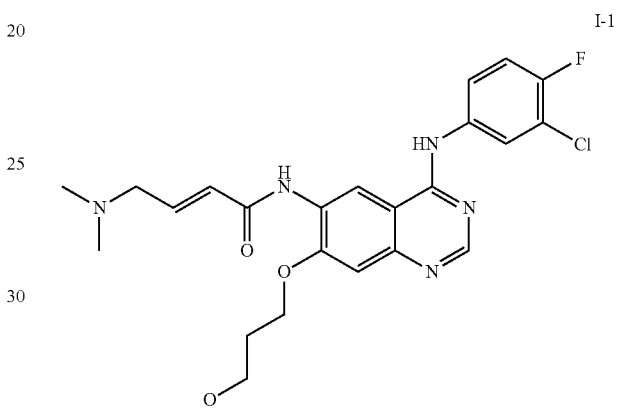
I-2
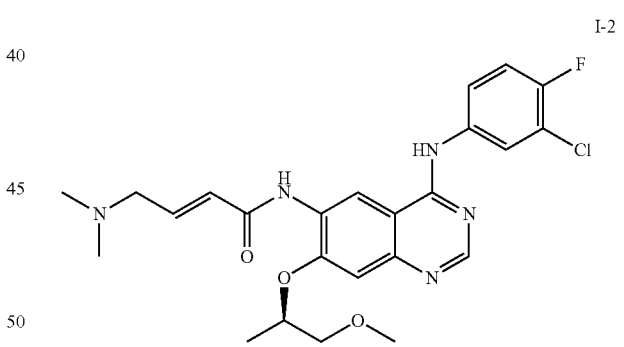
I-3
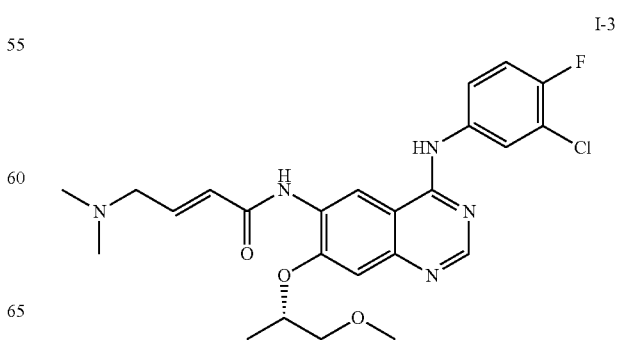

I-4
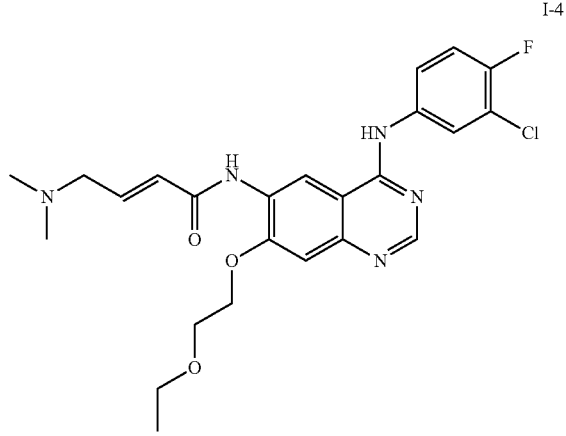
I-5
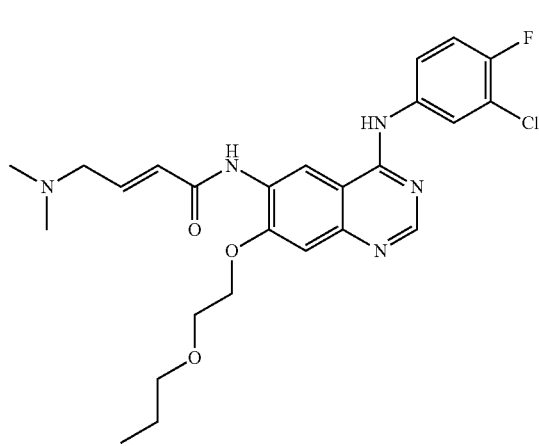
I-6
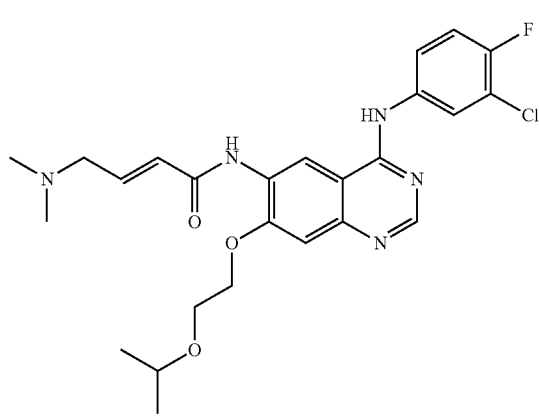
I-7
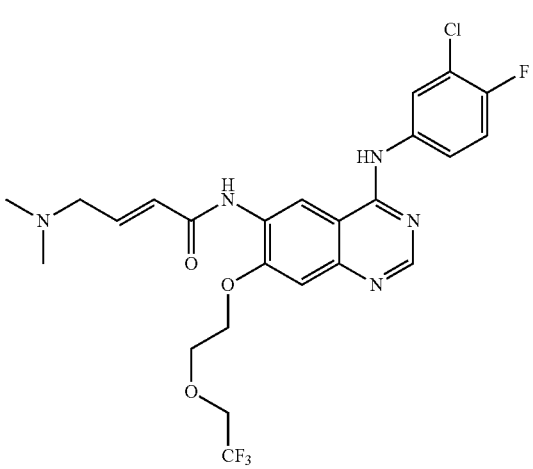
I-8
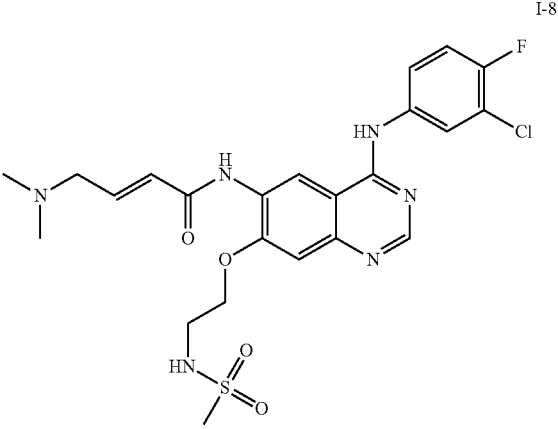
I-9
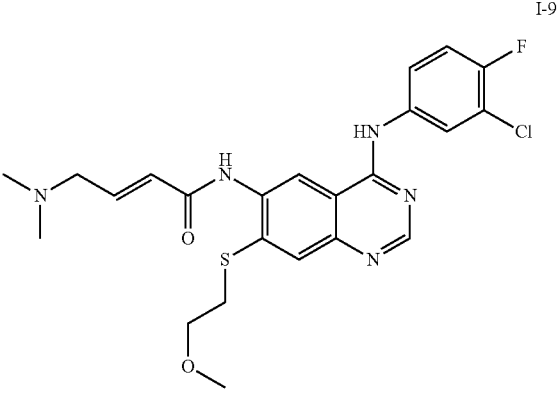

I-10
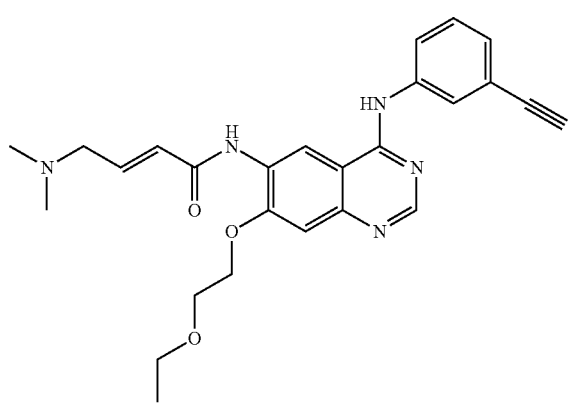
I-13
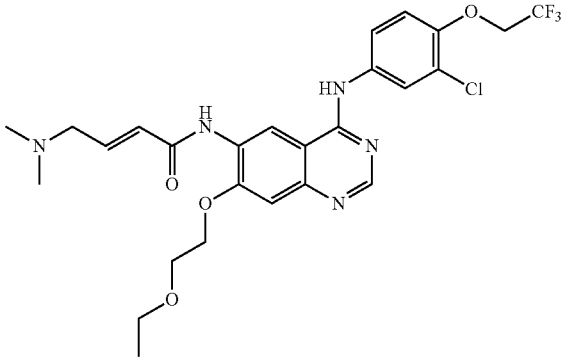
I-11
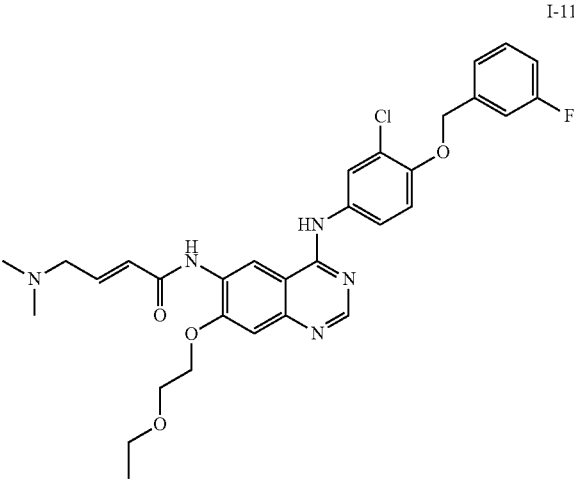
I-14
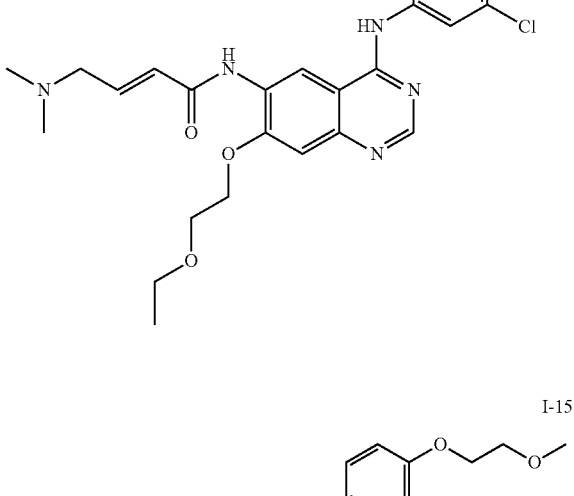
I-12
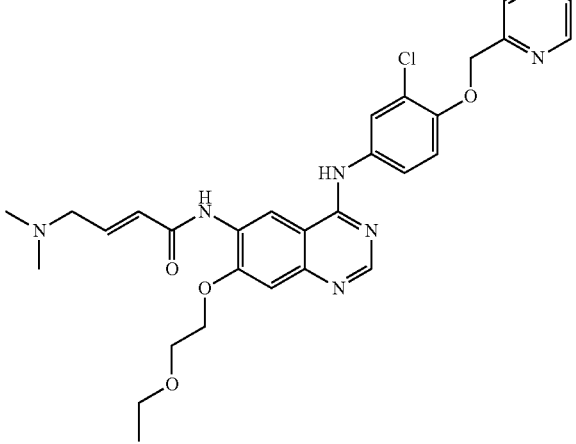
I-15
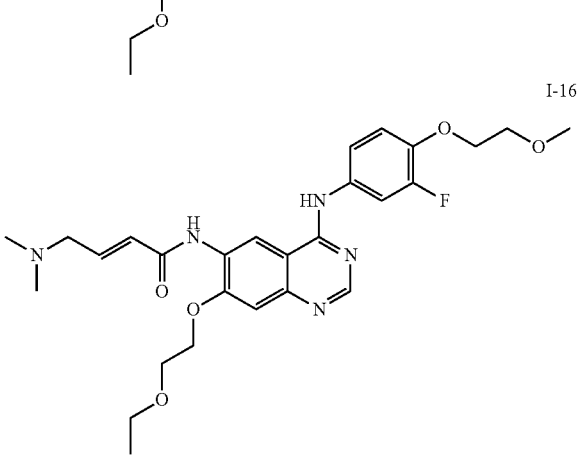
I-16

I-17
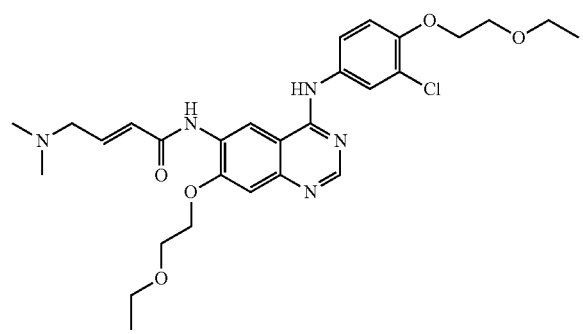
I-18
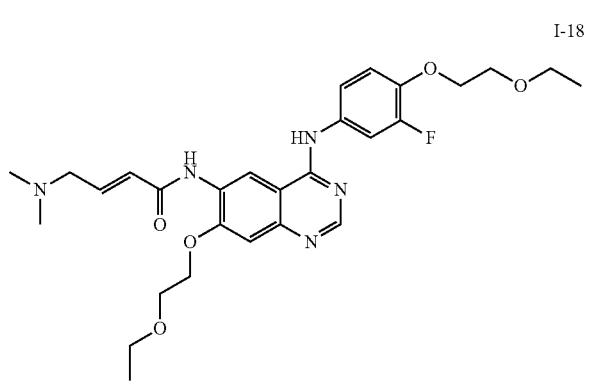
I-19
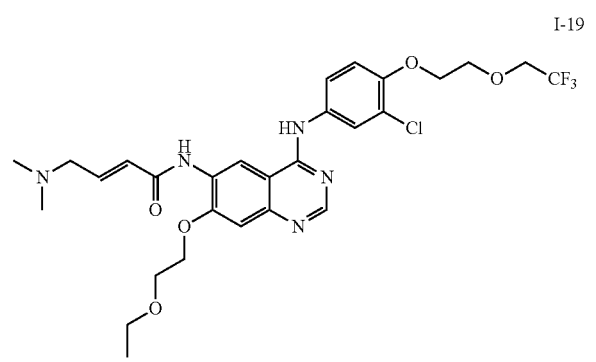
I-20
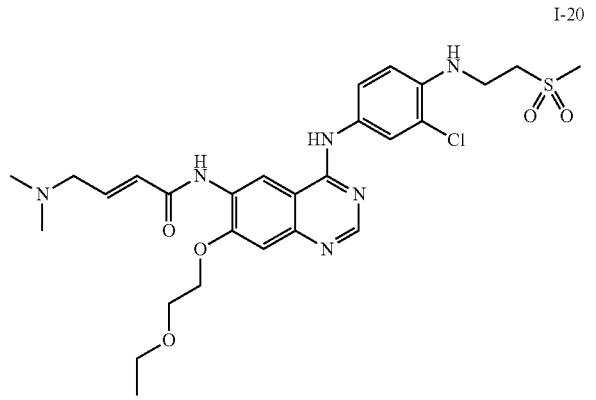
I-21
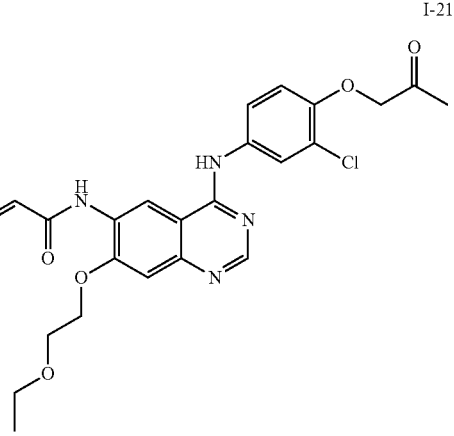
I-22
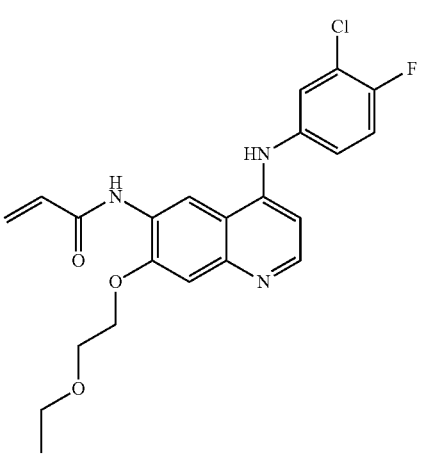
I-23
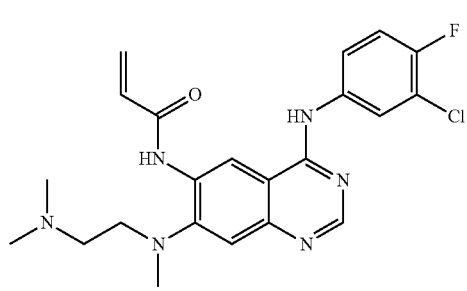
I-24
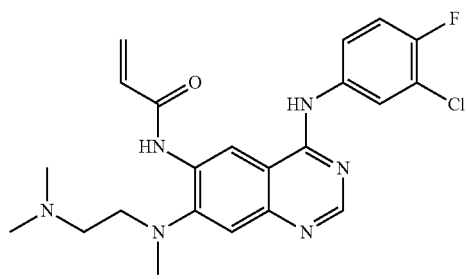

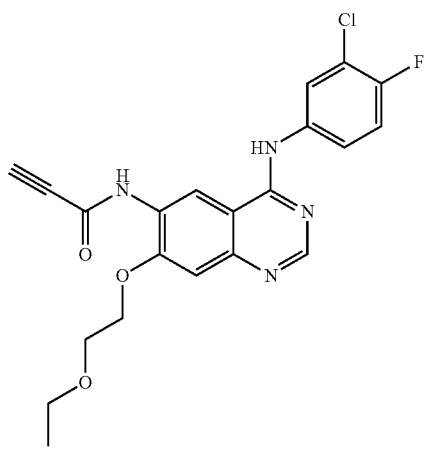 I-25
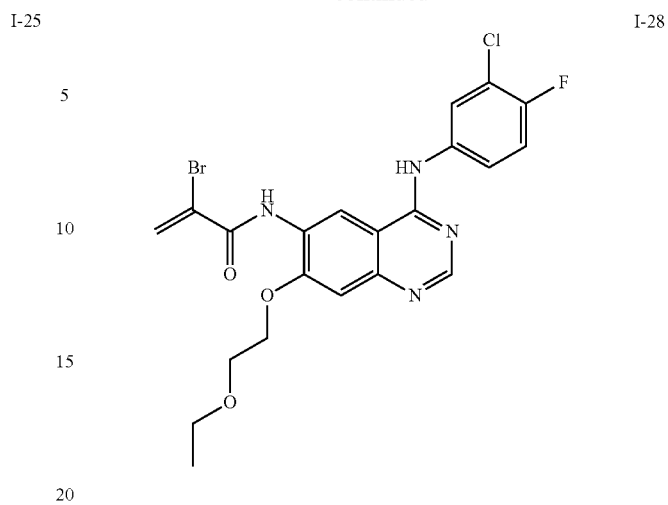 I-28
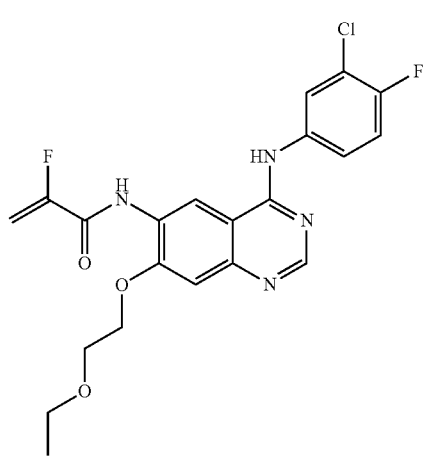 I-26
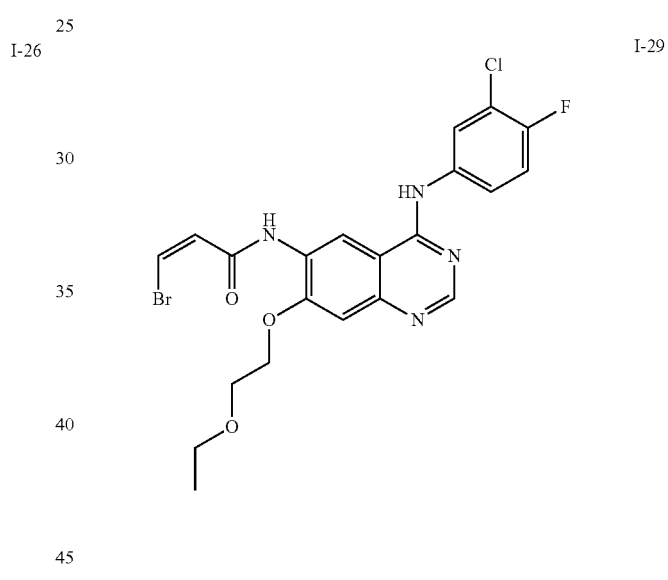 I-29
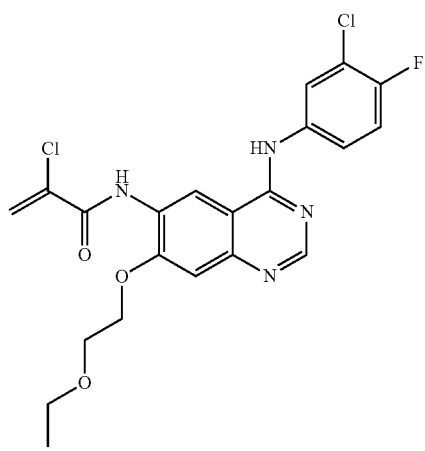 I-27
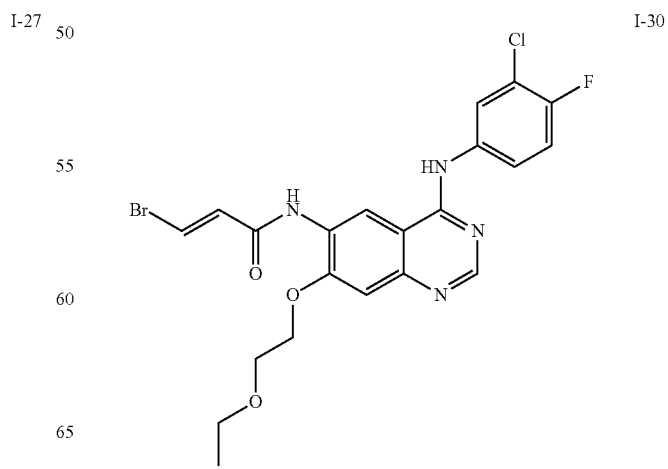 I-30

I-31
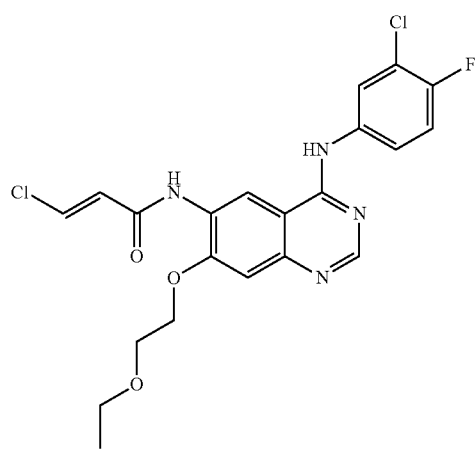
I-34
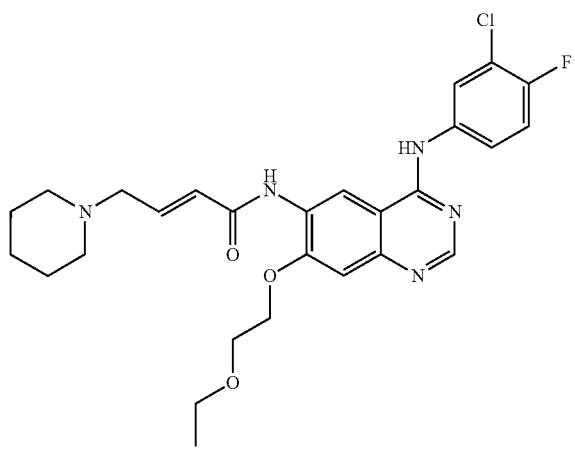
I-32
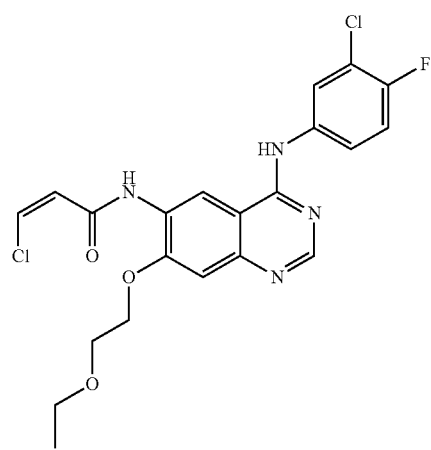
I-35
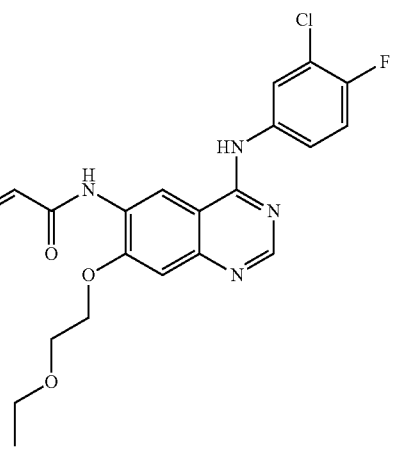
I-33
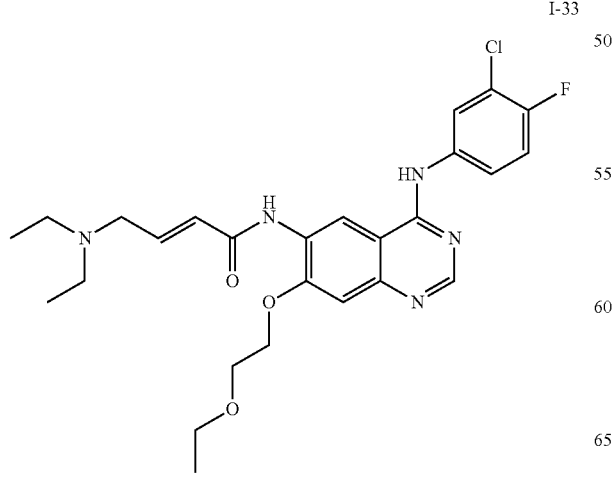
I-36
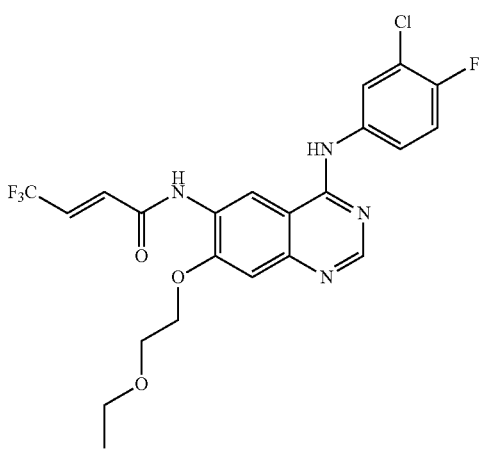

-continued

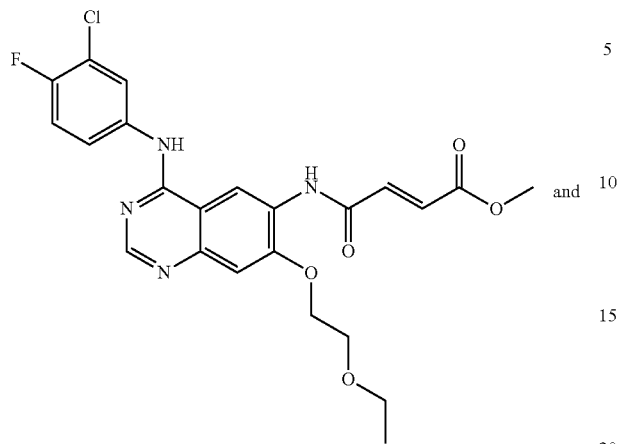

I-37 and

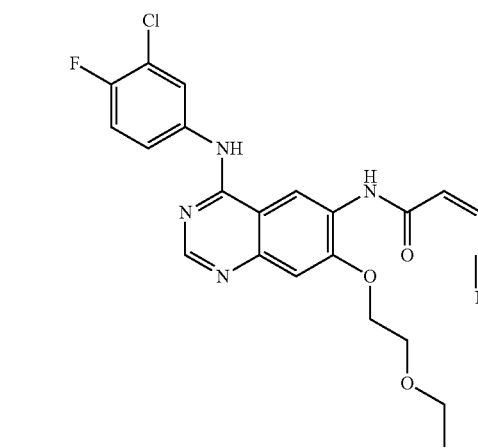

I-38

8. A process for preparing the compound represented by general formula I according to claim 1, which comprises the following procedure: reacting R⁶Cl or R⁶OH with compound IV in a solvent to arrive at the general formula I by a condensation reaction;

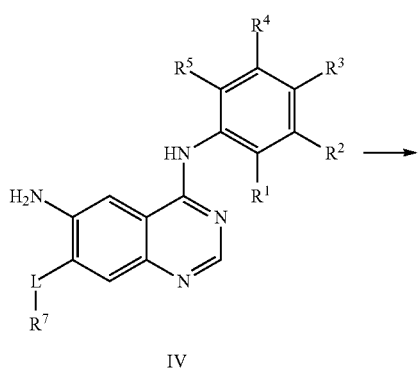

IV

-continued

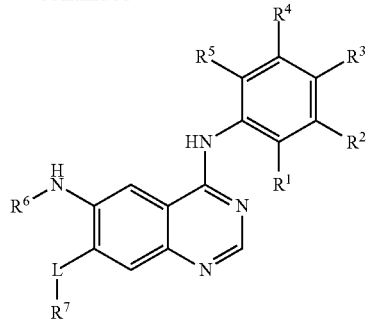

I wherein, $R^1$, $R^2$, $R^3$, $R^4$, $R^5$, $R^6$, $R^7$ and L are defined as claim 1.

9. The method for treating diseases or conditions associated with receptor tyrosine kinases comprising: administrating the compound represented by general formula I, the stereoisomer thereof and the pharmaceutical acceptable salt or the solvate thereof according to claim 1 to the subject, the diseases or conditions associated with receptor tyrosine kinases are selected from the group consisting of skin cancer, lung cancer and breast cancer.

10. A pharmaceutical composition comprising the compound represented by general formula I, the pharmaceutically acceptable salt thereof, the stereoisomer thereof or the solvate thereof according to claim 1 in association with one or more of pharmaceutically acceptable carriers or excipients.

11. A method for treating diseases or conditions associated with receptor tyrosine kinases in a subject in need thereof, comprising: administrating an effective amount of the pharmaceutical composition according to claim 10 to the subject, the diseases or conditions associated with receptor tyrosine kinases are selected from the group consisting of skin cancer, lung cancer and breast cancer.

12. A method for inhibiting EGFR tyrosine kinase and Her-2 enzyme comprising: administrating the compound represented by general formula I, the pharmaceutically acceptable salt thereof, the stereoisomer thereof or the solvate thereof according to claim 1 to a subject in need thereof.

13. A pharmaceutical composition comprising the compound represented by general formula I, the pharmaceutically acceptable salt thereof, the stereoisomer thereof or the solvate thereof according to claim 1 and other therapeutic agents, the other therapeutic agents are selected from the group consisting of nitrogen mustard, aziridine, methyl melamine, sulfonic acid alkyl ester, nitrosourea, triazene, folic acid analogue, pyrimidine analogue, purine analogue, vinca alkaloid, epipodophyllotoxins, antibiotics, topoisomerase inhibitor, anticancer vaccine, acivicin, aclarubicin, acodazole hydrochloride, acronine, adozelesin, aldesleukin, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, mesylate bisnafide, bizelesin, bleomycin sulfate, busulfan, actinomycin-C, calusterone, caracemide, carbetimer, carboplatin, carmustine, carubicin hydrochloride, idarubicin hydrochloride, ifosfamide, interleukin-II, interferon alpha-2a, interferon alpha-2b, irinotecan hydrochloride, letrozole, mercaptopurine, methotrexate, metoprine, mitomycin, mitoxantrone, paclitaxel, procarbazine, pethidine, vincaleukoblastinum, vincristine, angiogenesis inhibitor, camptothecin, dexamethasone, aspirin, acetyl aminophenol, indometacin, ibuprofen, ketoprofen, meloxicam, corticosteroid and adrenocortical steroid.

* * * * *